US008551693B2

(12) United States Patent
Chahine

(10) Patent No.: US 8,551,693 B2
(45) Date of Patent: Oct. 8, 2013

(54) MUTATED VOLTAGE-GATED SODIUM CHANNEL NA$_v$ ALPHA SUBUNIT FOR IDENTIFICATION OF MODULATORS

(75) Inventor: Mohamed Chahine, Quebec (CA)

(73) Assignee: Université Laval, Quebec (CA)

( * ) Notice: Subject to any disclaimer, the term of this patent is extended or adjusted under 35 U.S.C. 154(b) by 30 days.

(21) Appl. No.: 13/140,657

(22) PCT Filed: Dec. 21, 2009

(86) PCT No.: PCT/CA2009/001838
§ 371 (c)(1),
(2), (4) Date: Jun. 17, 2011

(87) PCT Pub. No.: WO2010/071983
PCT Pub. Date: Jul. 1, 2010

(65) Prior Publication Data
US 2012/0040368 A1    Feb. 16, 2012

Related U.S. Application Data

(60) Provisional application No. 61/139,790, filed on Dec. 22, 2008.

(51) Int. Cl.
| C12Q 1/00 | (2006.01) |
| C12Q 1/68 | (2006.01) |
| C12N 15/63 | (2006.01) |
| C12N 15/85 | (2006.01) |
| C07H 21/04 | (2006.01) |
| C07K 14/435 | (2006.01) |

(52) U.S. Cl.
USPC ............... 435/4; 435/6; 435/320.1; 435/325; 530/350; 536/23.1

(58) Field of Classification Search
None
See application file for complete search history.

(56) References Cited

U.S. PATENT DOCUMENTS 5,858,713 A    1/1999   Soderlund et al.

FOREIGN PATENT DOCUMENTS

| WO | WO2007/109324 | 9/2007 |
| WO | PCT/CA2009/001838 | 3/2010 |

OTHER PUBLICATIONS

Armstrong C. et al., Inactivation of the Sodium Channel, J Gen Physiol 1977, 70: 567-590.
Armstrong C. et al., Voltage-gated Ion Channels and Electrical Excitability, Neuron 1998, 20: 371-380.
Baroudi et al., Expression and intracellular localization of an SCN5A double mutant R1232W/TI620M implicated in Brugada Syndrome, Circulation Research 2002, 90:e11-e15.
Biswas et al. Calcium-mediated dual-mode regulation of cardiac sodium channel gating, Circulation Research 2009, 104:870-878.
Catterall W., Molecular Properties of Voltage-Sensitive Sodium Channels, Annu Rev Biochem 1986, 55: 953-985.
Chahine et al., Voltage-gated Sodium Channels in Neurological Disorders, CNS & Neurological Disorders—Drug Targets, 2008, 7:144-158.
Chiamvimonvat et al., Depth Asymmetries of the Pore-Lining Segments of the Na+ Channel Revealed by Cysteine Mutagenesis, Neuron 1996, 16: 1037-1047.
Evanko et al., Elimination of environmental sensitivity in a cameleon FRET-based calcium sensor via replacement of the acceptor with venus, Cell Calcium 2005 37: 341-348.
Favre et al., On the structural basis for ionic selectivity among Na+, K+ and CA2 in the voltage-gated sodium channel, Biophysical Journal, 1996 (71):3110-3125.
Fozzard et al., Structure and function of voltage-dependent sodium channels : comparison of brain II and cardiac isoforms, Physiol Rev 1996, 76: 887-926.
Gellens et al., Primary structure and functional expression of the human cardiac tetrodotoxin-insensitive voltage-dependent sodium channel, Proc. Natl. Acad. Sci. USA 89: 554-558.
George Al Jr., Inherited disorders of voltage-gated sodium channels, J Clin Invest 2005, 115: 1990-1999.
Guy et al., Molecular model of the action potential sodium channel, Proc Natl Acad Sci USA 1986, 83: 508-512.
Guy et al., Pursuing the structure and function of voltage-gated channels, Trends Neurosci 1990, 13: 201-206.
Heinemann et al., Calcium channel characteristics conferred on the sodium channel by single mutations, Nature 1992, 356:441-443.
Ikura et al., Solution structure of a calmodulin-target peptide complex by multidimensional NMR, Science 1992, 256:632-638.
Kontis K. et al., Sodium channel activation gating is affected by substitutions of voltage sensor positive charges in all four domains, J Gen Physiol 1997, 110: 391-401.
McPhee J. et al., A mutation segment IVS6 disrupts fast inactivation of sodium channels, Proc Natl Acad Sci USA 1994, 91: 12346-12350.
McPhee J. et al., A critical role for transmembrane segment IVS6 of the sodium channel a subunit in fast inactivation, J Biol Chem 1995, 270: 12025-12034.
Miyakawaki et al., Fluorescent indicators for CA2+ based on green fluorescent proteins and calmodulin, Nature 1997, 388:882-887.
Nagai T. et al., A variant of yellow fluorescent protein with fast and efficient maturation for cell-biological application, Nat. Biotechnol. 2002, 20: 87-90.
Pérez-García MT et al., Mechanisms of sodium/calcium selectivity in sodium channels probed by cysteine mutagenesis and sulfhydryl modification, Biophys J 1997, 72: 989-996.

(Continued)

Primary Examiner — Ruixiang Li
(74) Attorney, Agent, or Firm — Goudreau Gage Dubuc; S. Serge Shahinian; Alain Dumont

(57) ABSTRACT

Reagents, methods and kits for screening for compounds that modulate the activity of voltage-gated sodium channels (NaV), such as human NaV1.5/SC-N5A/hH1 are described. The reagents, methods and kits are based on mutated NaV alpha subunit polyptides of SEQ ID NO:5 with mutations at positions 372, 898, 1419 and 1711 (the DEKA motif) and at positions 11485, 1486 and 1487 (the IFM motif) resulting in increased permeability for a group IIA divalent cation (Ca$^{++}$) and decreased inactivation rate. The mutant polypeptide is used in a method and kit for determining whether a test compound modulates the channel activity, preferably using a chimeric polypeptide (chameleon polypeptide) comprising calmodulin, a calmodulin binding protein (M13), and two fluorescent agents.

11 Claims, 11 Drawing Sheets

(56) References Cited

OTHER PUBLICATIONS

Pérez-García MT et al., Structure of the sodium channel pore revealed by serial cysteine mutagenesis, Proc Natl Acad Sci USA 1996, 93: 300-304.

Ragsdale DS et al., Common molecular determinants of local anesthetic, antiarrhytmic, and anticonvulsant block of voltage-gated Na+ channels, Proc Natl Acad Sci USA 1996, 93: 9270-9275.

Remme CA et al., Cardiac sodium channel overlap syndromes: different faces of SCN5A mutations, Trends Cardiovasc Med. 2008, 18(3): 78-87.

Rutter et al., Real-time imaging of gene expression in single living cells, 1998, Chemistry & Biology 5: R285-R290.

Smith M. et al., Interaction between the sodium channel inactivation linker domain III S4-S5, Biophys J 1997, 73: 1885-1895.

Stühmer W et al., Structural parts involved in activation and inactivation of the sodium channel, Nature 1989, 339: 597-603.

Terlau H et al., Mapping the site of block by tetrodoxin and saxitoxin of sodium channel II, FEBS Lett 1991, 293: 93-96.

Terstappen, Ion channel screening technologies today, 2005, Drug Discov Today: Technologies 2(2): 133-40.

Velicelebi et al., Fluorescence Techniques for Measuring Ion Channel Activity, 1999, Meth. Enzymol. 294: 20-47.

West et al., A cluster of hydrophobic amino acid residues required for fast Na+-channel inactivation, Proc. Natl. Acad. Sci USA, 1992, 89: 10910-10914.

Yamagishi T et al., Topology of the P segments in the sodium channel pore revealed by cysteine mutagenesis, Biophys J 1997, 73: 195-204.

Yang N et al., Probing the outer vestibule of a sodium channel voltage sensor, Biophys J 1997, 73: 2260-2268.

Zhang JH et al., A simple statistical parameter for use in evaluation and validation of high throughput screening assays, J Biomol Screen 1999, 4(2): 67-73.

CFP channel          Venus channel

Human Nav1.5<sup>mut</sup>

```
   1 manfllprgt ssfrrftres laaiekrmae kqargstllq esreqlpeee aprpqldlqa
  61 skklpdlyen ppqeliqepl edldpfystq ktfivlnkqk tifrfsatna lyvlspfhpi
 121 rraavkilvh slfnmlimct iltncvfmaq hdpppwtkyv eytftaiytf eslvkilarg
 181 fclhafttlr dpwnwldfsv iimayftefv dlgnvsalrt trvlralkti svisglkriv
 241 galiqsvkkl advnvltvfc lsvfaliglq lfmgnlrhkc vrnftalngt ngsveadqlv
 301 wesldlylsd penyllkngt sdvllcgnss dagtcpegyr clkagenpdh gytsfdsfaw
 361 aflalfrlmt qdcwerlyqq tlrsagkiym iffmlviflg sfylvnlila vvamayeeqn
 421 qatiaeteek ekrfqeamem lkkshealti rgvdtvsrss lemsplapvr sherrskrrk
 481 rmssqteecq edrlcksdse dqpramnhls ltrqlsrtsm kprssrqsif tfrrrdlqse
 541 adfaddenst agesesnhts llvpwplrrt saqgqpspgt sapghalhgk knstvdcngv
 601 vsllgagdpe atspgshllr pvmlehpcdt ttpseepggp qmltsqapcv dgfeepgarq
 661 ralsavsvlt salcclccsr hkcppcwnrl acryliwccc plwmsikqgv klvvmdpftd
 721 ltitmcivln tlfmalehyn mtsefeemlq vqnlvftqif taemtfkiia ldpyyyfqqq
 781 wnifdsiivi lslnelglsr msnlsvlrsf rllrvfklak swptlntlik iignsvgalg
 841 nltlvlaiiv fifavvgmql fgknyselrd scsglprwh mmdthafli ifrilcgewi
 901 etmwdcmevs gqslcllvfl lvmvignlvv lnlflallls sfsadnltap dedremnnlq
 961 lalariqrql rfvkrttwdf ccgllrqrpq kpaalaaqgq lpsciatpys ppppetekvp
1021 ptrketrfee geqpgqgtpg dpepvcvpia vaesdtcdqe edeenslqte eesskqqesq
1081 pvsggpcapp dsrtwsqvsa tasscacasa scadwrcqwk acpqapgcgc tpcdscscgs
1141 tadmtntael leqipdlqqd vkdpedcfte ccvrrcpcca vdttqapqkv wwrlrktcyh
1201 ivehswfetf iifnillssg alafediyle erktikvlle yadkmftyvf vlemllkwva
1261 ygfkkyflna wcwldfllvd vslvslvanl lgfaemgpik slrtlralrp lralsrfegm
1321 rvvvnalvga ipsimnvllv clifwlifsi mgvnlfagkf grcinqtegd lplnytivnn
1381 ksqceslnlt gelywtkvkv nfdnvgagyl allqvatfeg wmdimyaavd srgyeeqpqw
1441 eynlymyiyf vfiifgsff tlnlfigvii dnfnqqkkkl ggqdigmtee qkkyynamkk
1501 lgskkpqkpi prplnkyqgf ifdivnkqaf dvtimfliel nmvtmmvetd dqspekinil
1561 akinllfvai ftgecivkla alrhyyftns wnifdfvvvi lsivgtvlsd iiqkyffspt
1621 lfrvirlari grilrlirga kgirtllfal mmslpalfni glllflvmfi ysifgmanfa
1681 yvkweagidd mfnfqtfans mlclfqitts agwdgllspi lntgppycdp tlpnsngsrg
1741 dcgspavgil ffttyiiisf livvnmyiai ilenfsvate esteplsedd fdmfyeiwek
1801 fdpeatqfie ysvlsdfada lseplriakp ncislinmdl pmvscdrihc mdilfafkr
1861 vlgesgemda lkiqmeektm aanpskisye pitttlrrkh eevsamviqr afrrhllqrs
1921 lkhasflfrq qagsglseed aperegliay vmsenfsrpl gppssssiss tsfppsydsv
1981 tratsdnlqv rqsdyshsed ladfppspdr dresiv
```

Fig. 7A

Human Nav1.5 alpha, isoform a (GenBank accession No. NP_932173)

```
   1 manfllpigt ssfirftres laalekimae kqargstllq esreglpeee apipqldlqa
  61 skklpdlygn ppqeligepl edldpfystq ktfivlnkgk tifrfsatna lyvlspfhpi
 121 rraavkilvh slfnmlimct iltncvfmaq hdpppwtkyv eytftaiytf eslvkilarg
 181 fclhaftflr dpwnwldfsv iimayttefv dlgnvsalrt frvlralkti svisglktiv
 241 galiqsvkkl advmvltvfc lsvfaliglq lfmgnlrhkc vrnftalngt ngsveadglv
 301 wesldlylsd penyllkngt sdvllcgnss dagtcpegyr clkagenpdh gytsfdsfaw
 361 aflalfrlmt qdcwerlyqq tlrsagkiym iffmlvifig sfylvnlila vvamayeeqn
 421 qatiaeteek ekrfqeamem lkkehealti rgvdtvsrss lemsplapvn sherrskrrk
 481 mssqteecg edrlpksdse dqpramnhls ltrqlsrtsm kprssrqsif tfrrrdlqse
 541 adfaddenst ageseshhts llvpwplrrt saqgqpspgt sapghalhgk knstvdcngv
 601 vsllgagdpe atspgshllr pvmlehppdt ttpseepggp qmltsqapcv dgfeepgarq
 661 ralsavsvlt saleeleesr hkcppcwnrl aqryliwecc plwmsikqgv klvvmdpftd
 721 ltimcivln tlfmalehyn mtsefeemlq vgnlvftgif taemtfkiia ldpyyyfqqg
 781 wnifdsiivi lslmelglsr msnlsvlrsf rllrvfklak swptlntlik iignsvgalg
 841 nltlvlaiiv fifavvgmql fgknyselrd sdsgllprwh mmdffhafli ifrilcgewi
 901 etmwdcmevs gqslcllvfl lvmvignlvv lniflallis sfsadnltap dedremnhlq
 961 lalariqrgl rfvkrttwdf ccgllrqrpq kpaalaaqgq lpsciatpys ppppetekvp
1021 ptrketrfee geqpgqgtpg dpepvcvpia vaesdtddqe edeenslgte eesskqqesq
1081 pvsggpeapp dsrtwsqvsa tasseaeasa sqadwrqqwk aepqapgcge tpedscsegs
1141 tadmtntacl lcqipdlgqd vkdpcdcfte gcvrrcpcca vdttqapgkv wwrlrktcyh
1201 ivehswfetf iifmillssg alafediyle erktikvlle yadkmftyvf vlemllkwva
1261 ygfkkyftna wcwldflivd vslvslvant lgfaemgpik slrtlralrp lralsrfegm
1321 rvvvnalvga ipsimnvllv clifwlifsi mgvnlfagkf grcinqtegd lplnytivnn
1381 ksqceslnlt gelywtkvkv nfdnvgagyl allqvatfkg wmdimyaavd srgyeeqpqw
1441 eynlymyiyf vifiifgsff tlnlfigvii dnfnqqkkkl ggqdifmtee qkkyynamkk
1501 lgskkpqkpi prplnkyqgf ifdivtkqaf dvtimflicl nmvtmnvetd dqspekinil
1561 akinllfvai ftgecivkla alrhyyftns wnifdfvvvi lsivgtvlsd iiqkyffspt
1621 lfrvirlari grilrlirga kgirtllfal mmslpalfni glllflvmfi ysifgmanfa
1681 yvkweagidd mfnfqtfans mlclfqitts agwdgllspi lntgppycdp tlpnsngsrg
1741 dcqspavqil ffttyiiisf livvnmyiai ilenfsvate estepisedd fdmfyeiwek
1801 fdpeatqfie ysvlsdfada lseplriakp nqislinmdl pmvsgdrihc mdilfafktr
1861 vlgesgemda lkiqmeekim aanpskisye pitttlrrkh eevsanviqr afrrhllqrs
1921 lkhasflfrq qagsglseed aperegliay vmsenfsrpl gppsssiss tsfppsydsv
1981 tratsdnlqv rgsdyshsed ladfppspdr dresiv
```

Fig. 7B

Human Na$_v$1.5 alpha, isoform b (GenBank accession No. NP_000326)

```
   1  manfllprgt  ssfrrftres  laaiekrmae  kqargsttlq  esreglpeee  aprpqldlqa
  61  skklpdlygn  ppqeligepl  edldpfystq  ktfivlnkgk  tifrfsatna  lyvlspfhpi
 121  rraavkilvh  slfnmlimct  iltncvfmaq  hdpppwtkyv  eytftaiytf  eslvkilarg
 181  fclhaftflr  dpwnwldfsv  iimayttefv  dlgnvsalrt  frviralkti  svisglktiv
 241  galiqsvkkl  advmvltvfc  lsvfaliglq  lfmgnlrhkc  vrnftalngt  ngsveadglv
 301  wesldlylsd  penyllkngt  sdvllcgnss  dagtcpegyr  clkagenpdh  gytsfdsfaw
 361  aflalfrlmt  qdcwerlyqq  tlrsagkiym  iffmlviflg  sfylvnlila  vvamayeeqn
 421  qatiaeteek  ekrfqeamem  lkkehealti  rgvdtvsrss  lemsplapvn  sherrskrrk
 481  rmssqteecq  edrlpksdse  dqpramnhls  ltrqlsrtsm  kprssrqsif  tfrrrdlqse
 541  adfaddenst  ageseshhts  llvpwplrrt  saqgqpspgt  sapghalhgk  knstvdcngv
 601  vsllgagdpe  atspgshllr  pvmlehppdt  ttpseepggp  qmltsqapcv  dgfeepgarq
 661  ralsavsvlt  saleeleesr  hkcppcwnrl  aqryliwecc  plwmsikqgv  klvvmdpftd
 721  ltitmcivln  tlfmalchyn  mtsefccmlq  vgnlvftgif  tacntfkiia  ldpyyyfqqg
 781  wnifdsiivi  lslmelglsr  msnlsvlrsf  rllrvfklak  swptlntlik  iignsvgalg
 841  nltlvlaiiv  fifavvgmql  fgknyselrd  sdsgllprwh  mmdffhafli  ifrilcgewi
 901  etmwdcmevs  gqslcllvfl  lvmvignlvv  lnlflallls  sfsadnltap  dedremnnlq
 961  lalariqrgl  rfvkrttwdf  ccgllrqrpq  kpaalaaqgq  lpsciatpys  ppppetekvp
1021  ptrketrfee  geqpgqgtpg  dpepvcvpia  vaesdtddqe  edeenslgte  eesskqesqp
1081  vsggpeappd  srtwsqvsat  asseaeasas  qadwrqqwka  epqapgcget  pedscsegst
1141  admtntaell  eqipdlgqdv  kdpedcfteg  cvrrcpccav  dttqapgkvw  wrlrktcyhi
1201  vehswfetfi  ifmillssga  lafediylee  rktikvlley  adknftyvfv  lemllkwvay
1261  gfkkyftnaw  cwldflivdv  slvslvantl  gfaemgpiks  lrtiralrpl  ralsrfegmr
1321  vvvnalvgai  psimnvllvc  lifwlifsim  gvnlfagkfg  rcinqtegdl  plnytivnnk
1381  sqccslnltg  clywtkvkvn  fdnvgagyla  llqvatfkgw  mdinyaavds  rgyccqpqwc
1441  ynlymyiyfv  ifiiifgsfft  lnlfigviid  nfnqqkkklg  gqdifmteeq  kkyynamkkl
1501  gskkpqkpip  rplnkyqgfi  fdivtkqafd  vtimflicln  mvtnmvetdd  qspekinila
1561  kinllfvaif  tgecivklaa  lrhyyftnsw  nifdfvvvil  sivgtvlsdi  iqkyffsptl
1621  frvirlarig  rilrlirqak  girtllfalm  mslpalfnig  lllflvmfiy  sifgmanfay
1681  vkweagiddm  fnfqtfansm  lclfqittsa  gwdgllspil  ntgppycdpt  lpnsngsrgd
1741  cgspavgilf  fttyiiisfl  ivvnmyiaii  lenfsvatee  steplseddf  dmfyeiwekf
1801  dpeatqfiey  svlsdfadal  seplriakpn  qislinmdlp  mvsgdrihcm  dilfaftkrv
1861  lgesgemdal  kiqmeekfma  anpskisyep  itttlrrkhe  evsamviqra  frrhllqrsl
1921  khasflfrqq  agsglseeda  peregliayv  msenfsrplg  ppssssisst  sfppsydsvt
1981  ratsdnlqvr  gsdyshsedl  adfppspdrd  resiv
```

Fig. 7C

Human Nav1.5 alpha, isoform c (GenBank accession No. NP_001092874)

```
   1 manfllprgt ssfrrftres laaiekrmae kqargsttlq esreglpeee aprpqldlqa
  61 skklpdlygn ppqeligepl edlcpfystq ktfivlnkgk tifrfsatna lyvlspfhpi
 121 rraavkilvh slfnmlimct iltncvfmaq hdpppwtkyv eytftaiytf eslvkilarg
 181 fclhaftflr dpwnwldfsv iimayvseni klgnlsalrt frvlralkti svipglktiv
 241 galiqsvkkl advmvltvfc lsvfaliglq lfmgnlrhkc vrnftalngt ngsveadglv
 301 wesldlylsd penyllkngt sdvllcgnss dagtcpegyr clkagenpdh gytsfdsfaw
 361 aflalfrlmt qdcwerlyqq tlrsagkiym iffmlviflg sfylvnlila vvamayeeqn
 421 qatiaeteek ekrfqeamem lkkehealti rgvdtvsrss lemsplapvn sherrskrrk
 481 rmssgteecg edrlpksdse dgpramnhls ltrglsrtsm kprssrgsif tfrrrdlgse
 541 adfaddenst ageseshhts llvpwplrrt saqgqpspgt sapghalhgk knstvdcngv
 601 vsllgagdpe atspgshllr pvmlehppdt ttpseepggp qmltsqapcv dgfeepgarq
 661 ralsavsvlt saleeleesr hkcppcwnrl aqryliwecc plwmsikqgv klvvndpftd
 721 ltitmcivln tlfmalehyn mtsefeemlq vgnlvftgif taemtfkiia ldpyyyfqqg
 781 wnifdsiivi lslmelglsr msnlsvlrsf rllrvfklak swptlntlik iignsvgalg
 841 nltlvlaiiv fifavvqmql fgknyselrd sdsqllprwh mmdffhafli ifrilcgewi
 901 etmwdcmevs gqslcllvfl lvmvignlvv lnlflallls sfsadnltap dedremnnlq
 961 lalariqrgl rfvkrttwdf cdgllrqrpq kpaalaaqgq lpsciatpys ppppetekvp
1021 ptrketrfee geqpgcgtpg dpepvcvpia vaesdtddqe edeenslgte eesskqqesq
1081 pvsggpeapp dsrtwsqvsa tasseaeasa sqadwrqqwk aepcapgcge tpedscsegs
1141 tadmtntael leqipdlgqd vkdpedcfte gcvrrcpcca vdttqapgkv wwrlrktcyh
1201 ivehswfetf iifmillssg alafediyle erktikvlle yadkmftyvf vlemllkwva
1261 ygfkkyftna wcwldflivd vslvslvant lgfaemgpik slrtlralrp lralsrfegm
1321 rvvvnalvga ipsimnvllv clifwlifsi mgvnlfagkf grcinqtegd lplnytivnn
1381 ksqceslnlt gelywtkvkv nfdnvgagyl allcvatfkg wmdimyaavd srgyeeqpqw
1441 eynlymyivf vifiifqsff tlnlfiqvii dnfnqqkkkl gqqdifmtee qkkyynamkk
1501 lgskkpqkpi prplnkyqgf ifdivtkqaf dvtinflicl nmvtnmvetd dqspekinil
1561 akinllfvai ftceciivkla alrhyyftns wnifdfvvvi lsivqtvlsd iiqkyffspt
1621 lfrvirlari qrilrlirqa kgirtllfal mmslpalfni clllflvmfi ysifqmanfa
1681 yvkweaqidd mfnfqtfans mlclfqitts agwdqllspi lntqppycdp tlpnsngsrq
1741 dcgspavqil ffttyiiisf livvnmyiai ilenfsvate esteplsedd fdmfyeiwek
1801 fdpeatqfie ysvlsdfada lseplriakp nqislinmdl pmvsgdrihc mdilfaftkr
1861 vlgesgemda lkiqmeekfm aanpskisye pitttlrrkh eevsamviqr afrrhllqrs
1921 lkhasflfrq qagsglseed aperegliay vmsenfsrpl gppssssiss tsfppsydsv
1981 tratscnlqv rgsdyshsed ladfppspdr dresiv
```

Fig. 7D

Human Nav1.5 alpha, isoform d (GenBank accession No. NP_001092875)

```
   1 manfllprgt ssfrrftres laaiekrmae kqargsttlq esreglpeee aprpqldlqa
  61 skklpdlygn ppqeligepl edldpfystq ktfivlnkgk tifrfsatna lyvlspfhpi
 121 rraavkilvh sltnmlimct iltncvfmaq hdpppwtkyv eytttaiyti eslvkilarg
 181 fclhaftflr dpwnwldfsv iimayvseni klgnlsalrt frvlralkti svipglktiv
 241 galiqsvkkl advmvltvfc lsvfaliglq lfmgnlrhkc vrnftalngt ngsveadglv
 301 wesldlylsd penyllkngt sdvllcgnss dagtcpegyr clkagenpdh gytsfdsfaw
 361 aflalfrlmt gdcwerlyqq tlrsagkiym iffmlviflg sfylvnlila vvamayeeqn
 421 qatiaeteek ekrfqeamem lkkehealti rgvdtvsrss lemsplapvn sherrskrrk
 481 rmssgteecg edrlpksdse dgpramnhls ltrglsrtsm kprssrgsif tfrrrdlgse
 541 adfaddenst ageseshhts llvpwplrrt saqgqpspgt sapghalhgk knstvdcngv
 601 vsllgagdpe atspgshllr pvmlchppdt ttpsccpgqp qmltsqapcv dgfccpgarq
 661 ralsavsvlt saleeleesr hkcppcwnrl aqryliwecc plwmsikqgv klvvmdpftd
 721 ltitmcivln tlfmalehyn mtsefeemlq vgnlvftgif taemtfkiia ldpyyyfqqg
 781 wnifdsiivi lslmelglsr manlsvlrsf rllrvfklak swptlntlik iignsvgalg
 841 nltlvlaiiv fifavvgmql fgknyselrd sdsgllprwh mmdffhafli ifrilcgewi
 901 etmwdcmevs gqslcllvfl lvmvignlvv lnlflallls stsadnltap dedremnnlq
 961 lalariqrgl rfvkrttwdf ccgllrqrpq kpaalaaqgq lpsciatpys ppppetekvp
1021 ptrketrfee geqpgcgtpg dpepvcvpia vaesdtddqe edeenslgte eesskqqesq
1081 pvsggpeapp dsrtwsqvsa tasseaeasa sqadwrqqwk aepcapgcge tpedscsegs
1141 tadmtntael leqipdlqqd vkdpedcfte qcvrrcpcca vdttqaoqkv wwrlrktcyh
1201 ivehswfetf iifmillssq alafediyle erktikvlle yadkmftyvf vlemllkwva
1261 ygfkkyftna wcwldflivd vslvslvant slrtlralrp slrtlralrp lralsrfegm
1321 rvvvnalvga ipsimnvllv clifwlifsi mgvnlfagkf grcinqtegd lplnytivnn
1381 ksqceslnlt gelywtkvkv nfdnvgagyl allqvyeecp qweynlymyi yfvifiifgs
1441 fftlnlfigv iidnfnqqkk klgggdifmt eeqkkyynam kklgskkpqk piprplnkyq
1501 gfifdivtkq afdvtimfli clnmvtmmve tddqspckin ilakinllfv aiftgccivk
1561 laalrhyyft nswnifdfvv vilsivgtvl sdiiqkyffs ptlfrvirla rigrilrlir
1621 gakgirtllf almmslpalf niglllflvm fiysifgman fayvkweagi ddmfnfqtfa
1681 nsmlclfqit tsagwdglsa pilntgppyc dptlpnsngs rgdcgspavg ilffttyiii
1741 sflivvnmyi aillenfsva teesteplse ddfdmfyeiw ekfdpeatqf ieysvlsdfa
1801 dalseplria kpnqislinm dlpmvsgdri hcmdilfaft krvlgesgem dalkiqmeek
1861 fmaanpskis yepitttlrr kheevsamvi qrafrrhllq rslkhasflf rqqagsqlse
1921 edapereqli ayvmsenfsr plqppssssi sstsfppsyd svtratsdnl qvrqsdyshs
1981 edladfppsp drdresiv
```

Fig. 7E

MUTATED VOLTAGE-GATED SODIUM CHANNEL NA$_v$ ALPHA SUBUNIT FOR IDENTIFICATION OF MODULATORS

CROSS REFERENCE TO RELATED APPLICATIONS

This application is a National Entry Application of PCT application no. PCT/CA2009/001838 filed on Dec. 21, 2009 and published in English under PCT Article 21(2), which claims benefit of U.S. Provisional Patent Application Ser. No. 61/139,790 filed on Dec. 22, 2008. All documents above are incorporated herein by reference in their entirety.

REFERENCE TO SEQUENCE LISTING

Pursuant to 37 C.F.R. 1.821(c), a sequence listing is submitted herewith as an ASCII compliant text file named "Sequence listing_ST25", created on Dec. 16, 2009 and having a size of 248 kilobytes. The content of the aforementioned file is hereby incorporated by reference in its entirety.

TECHNICAL FIELD

The present invention generally relates to sodium channels. More specifically, the present invention relates to the identification of modulators of voltage-gated sodium channels (Na$_v$), such as human Na$_v$1.5.

BACKGROUND ART

Voltage-gated sodium channels (VGSC or Na$_v$) produce the rapid upstroke of the action potential and are important elements for maintaining electrical excitability and assuring the coordination of excitation-contraction coupling in striated muscle and neuronal excitability. As shown in FIG. 1, they are composed of one α-subunit (260 kDa in the example shown), which forms the core of the channel and which is responsible for the voltage-dependent gating and ion permeation (Catterall W A, *Annu Rev Biochem* 1986, 55: 953-985; Fozzard H A and Hanck D A, *Physiol Rev* 1996, 76: 887-926; Armstrong C M and Hille B, *Neuron* 1998, 20: 371-380). The α-subunit is composed of four homologous domains (DI-DIV), each with six α-helical transmembrane-spanning segments (S1-S6). The S1-S4 domains form the voltage sensor domains (Stuhmer W et al., *Nature* 1989, 339: 597-603; Yang N et al., *Biophys J* 1997, 73: 2260-2268; Kontis K J et al., *J Gen Physiol* 1997, 110: 391-401). The short linkers connecting the S5 and S6 segments form the external mouth of the pore and the selective filter (Pérez-Garcia M T et al., *Biophys J* 1997, 72: 989-996; Yamagishi T et al., *Biophys J* 1997, 73: 195-204; Chiamvimonvat N et al., *Neuron* 1996, 16: 1037-1047; Pérez-Garcia M T et al., *Proc Natl Acad Sci USA* 1996, 93: 300-304). The cytoplasmic linker between the third (DIII) and fourth (DIV) homologous domains acts as a "hinged lid" that occludes the internal end of the permeation pathway during inactivation (Stühmer W et al., 1989, supra; Armstrong C M and Bezanilla F, *J Gen Physiol* 1977, 70: 567-590; West J W et al., *Proc Natl Acad Sci USA* 1992, 89: 10910-10914). Residues of the S6 segments from each of the four homologous domains (DIS6-DIVS6) line the internal vestibule and contribute to the binding site for local anaesthetics (LA) and antiarrhythmic drugs (Ragsdale D S et al., *Proc Natl Acad Sci USA* 1996, 93: 9270-9275). The cytoplasmic ends of the S6 segments and the short linkers from each of the four homologous domains that connect the S4-S5 segments contribute to the binding site for the native inactivation gate (Smith M R and Goldin A L, *Biophys J* 1997, 73: 1885-1895; McPhee J C et al., *Proc Natl Acad Sci USA* 1994, 91: 12346-12350; McPhee J C et al., *J Biol Chem* 1995, 270: 12025-12034).

Structure-function studies indicated that the S5-S6 linkers constitute the pore-forming regions known as P-loops of the channel (Pérez-Garcia M T et al., 1996, supra; Heinemann S H et al., *Nature* 1992, 356: 441-443; Terlau H et al., *FEBS Lett* 1991, 293: 93-96). Each P loop is composed of two short segments called SS1 and SS2, for short segment 1 and short segment 2 respectively, they span part of the plasma membrane (Terlau H et al., 1991, supra; Guy H R and Conti F, *Trends Neurosci* 1990, 13: 201-206; Guy H R and Seetharamulu P, *Proc Natl Aced Sci USA* 1986, 83: 508-512).

Sodium (Na) channel blockers have been developed and used for therapeutic purposes for several decades. One of the earliest compounds used for therapeutic purposes, that was later shown to block Na channels is cocaine. Cocaine, an aminoester, was the first local anesthetic drug useful in clinical surgery but it had undesirable side effects. It was however soon realized that the anesthetic properties of cocaine were preserved in chemically similar structures that had less undesirable side effects. This quickly led to the development of an entire class of cocaine-related compounds comprising other aminoesters like benzocaine and procaine, as well as aminoamides, like bupivacaine and lidocaine. Most of these drugs were/are typically not administered orally, but topically or intrathecally, thereby preventing adverse side effects, like convulsions and cardiovascular collapse, still associated with these drugs when applied systemically. The mechanisms by which these compounds interact with Na channels have been the subject of many scientific studies. Lidocaine in particular, still widely used in the clinic today, has been studied extensively. Lidocaine has shown efficacy in numerous pain conditions including diabetic neuropathy and postherpetic neuralgia.

Besides the "caine" class of analgesic compounds, certain clinically used anticonvulsants, antidepressants, and antiarrythmics have inhibitory activity on Na channels, which at least partially, underlie their clinical efficacy. Among such compounds are phenytoin, carbamazepine, and aminotryptyline. All these drugs block Na channels by binding to the DI-IV S6 transmembrane helices.

More recently, a number of mutations have been found to cause abnormal Na channel functions leading to human diseases or Na channelopathies such as periodic paralysis, myotonia, long QT syndrome and other cardiac conductance disturbances, pain, and epilepsy George A L Jr., *J Clin Invest* 2005, 115: 1990-1999).

Conventional methods for assaying sodium channel activity include radiolabeled toxin-binding assays, radioactive ion influx assays, electrophysiological patch-clamp assays, and membrane potential dyes (Reviewed by Terstappen, 2005, *Drug Discov Today: Technologies* 2(2): 133-40). All these assays have major disadvantages that limit their use. For example: i) the radioactive ion influx method requires long incubation time and multiple wash steps, necessitating non-homogeneous assay format. Moreover, it requires the use of chemical modifier of channel inactivation, introducing the risk of false positive or false negative results, and finally, it produces a large quantity of costly radioactive waste; ii) The patch clamp technique, largely considered the "gold standard", has inherent limitations, including low throughput and specialized equipment incompatible with standard laboratory robotics. Although higher throughput can be achieved with higher throughput patch-clamp such as IonWorks™ or PatchXpress™ (both from Molecular Devices Inc.), these assays are still relatively expensive and not well adapted for fast kinetics of VGSC.

Currently, in the industry, another approach that is used for drug-screening assays with VGSC is based on membrane potential-sensitive fluorescent dyes, such as bis-(1,3-dibutyl-barbituric acid)-trimethine oxonol ($DiBAC_4(3)$), because there are no efficient sodium dyes available. However, three major problems are associated with this technology: (i) Dyes such as $DiBAC_4(3)$ are sensible to any membrane potential changes and as a result it is not possible to employ extracellular potassium to open sodium channels and measure the sodium influx. It is necessary to use toxins, such as veratridine which the mechanism of action is not yet elucidated, to activate the sodium channel and monitor the ion influx. In a high-throughput screening context, this can generate many false positive or false negative results because the direct binding of veratridine to channels clearly changes their native conformation, and probably alters the interaction with the compounds to be tested; (ii) the use of fluorescent dyes involves time-consuming wash steps as well as the loss of cells and signal; (iii) membrane potential-sensitive fluorescent dyes are expensive, and are not suitable for endogenous expression due to their low response time and low sensitivity (Reviewed by Terstappen, 2005, supra).

There is thus a need for the development of novel reagents and methods for the identification of sodium channel modulators.

The present description refers to a number of documents, the content of which is herein incorporated by reference in their entirety.

SUMMARY OF THE INVENTION

In a first aspect, the present invention provides a mutated voltage gated sodium channel ($Na_v$) alpha subunit polypeptide comprising a first mutation that increases the permeability of the channel for a group IIA divalent cation and a second mutation that decreases the inactivation rate of the channel.

In an embodiment, the above-mentioned first mutation is a mutation in a domain connecting a S5 and a S6 α-helical transmembrane-spanning segment. In a further embodiment, the above-mentioned first mutation is:
(i) a mutation at a residue corresponding to residue 372 in the amino acid sequence of isoform A of human $Na_v1.5$ alpha subunit;
(ii) a mutation at a residue corresponding to residue 898 in the amino acid sequence of isoform A of human $Na_v1.5$ alpha subunit;
(iii) a mutation at a residue corresponding to residue 1419 in the amino acid sequence of isoform A of human $Na_v1.5$ alpha subunit;
(iv) a mutation at a residue corresponding to residue 1711 in the amino acid sequence of isoform A of human $Na_v1.5$ alpha subunit; or
(v) any combination of (i) to (iv).

In a further embodiment, the above-mentioned first mutation is a mutation at a residue corresponding to residue 1419 in the amino acid sequence of $Na_v1.5$ alpha subunit. In a further embodiment, the above-mentioned mutation at a residue corresponding to residue 1419 in the amino acid sequence of isoform A of human $Na_v1.5$ alpha subunit is a substitution to an alanine residue.

In an embodiment, the above-mentioned second mutation is a mutation in an intracellular region connecting the S6 α-helical transmembrane-spanning segment of Domain III and the S1 α-helical transmembrane-spanning segment of Domain IV.

In an embodiment, the above-mentioned second mutation is:
(i) a mutation at a residue corresponding to residue 1485 in the amino acid sequence of isoform A of human $Na_v1.5$ alpha subunit;
(ii) a mutation at a residue corresponding to residue 1486 in the amino acid sequence of isoform A of human $Na_v1.5$ alpha subunit;
(iii) a mutation at a residue corresponding to residue 1487 in the amino acid sequence of isoform A of human $Na_v1.5$ alpha subunit; or
(iv) any combination of (i) to (iii).

In a further embodiment, the above-mentioned second mutation is a mutation at a residue corresponding to residue 1486 in the amino acid sequence of $Na_v1.5$ alpha subunit. In a further embodiment, the above-mentioned mutation at a residue corresponding to residue 1486 in the amino acid sequence of isoform A of human $Na_v1.5$ alpha subunit is a substitution to a glutamine residue.

In an embodiment, the above-mentioned first mutation is at a residue corresponding to residue 1419 in the amino acid sequence of isoform A of human Nav1.5 alpha subunit, and the above-mentioned second mutation is at a residue corresponding to residue 1486 in the amino acid sequence of isoform A of human Nav1.5 alpha subunit.

In an embodiment, the above-mentioned mutated $Na_v$ alpha subunit polypeptide is a mutated human $Na_v1.5$ alpha subunit polypeptide. In a further embodiment, the above-mentioned mutated $Na_v$ alpha subunit polypeptide comprises the amino acid sequence of SEQ ID NO: 5.

In an embodiment, the above-mentioned group IIA divalent cation is calcium ($Ca^{2+}$).

In another aspect, the present invention provides an isolated nucleic acid encoding the above-mentioned mutated $Na_v$ alpha subunit polypeptide. In an embodiment, the above-mentioned nucleic acid comprises the nucleotide sequence of SEQ ID NO: 1, 2, 3 or 4.

In another aspect, the present invention provides a vector comprising the above-mentioned nucleic acid.

In another aspect, the present invention provides a cell comprising the above-mentioned nucleic acid or vector.

In another aspect, the present invention provides a method for determining whether a test compound modulates the activity of a voltage gated sodium channel, said method comprising
(a) providing a cell expressing the above-mentioned mutated $Na_v$ alpha subunit polypeptide; and
(b) determining the intracellular level of a group IIA divalent cation in said cell in the presence or absence of said test compound, wherein a difference in the intracellular level of said group IIA divalent cation in the presence relative to the absence of said test compound is indicative that said test compound modulates the activity of a voltage gated sodium channel.

In an embodiment, the above-mentioned method further comprises providing a source of said group IIA divalent cation in the extracellular medium. In another embodiment, the above-mentioned group IIA divalent cation is calcium ($Ca^{2+}$).

In an embodiment, the intracellular calcium level is determined by determining the conformational change of a calcium-binding polypeptide.

In an embodiment, the above-mentioned cell further expresses a first and second chimeric polypeptide, wherein
(i) said first chimeric polypeptide comprises:
(a) a first domain comprising a first fluorescent agent having an emission spectra;
(b) a second domain linked to said first domain and comprising a calcium-binding polypeptide;
(ii) said second chimeric polypeptide comprises:
(a) a first domain comprising a polypeptide which binds in a calcium-dependent manner to said calcium-binding polypeptide; and
(b) a second domain linked to said first domain of said second chimeric polypeptide and comprising a second fluorescent agent having an absorption spectra which overlaps with the emission spectra of said first fluorescent agent;
wherein the intracellular calcium level is determined by measuring the intensity of the fluorescence emitted by said second fluorescent agent.

In another embodiment, the above-mentioned cell further expresses a first and second chimeric polypeptide, wherein
(i) said first chimeric polypeptide comprises:
(a) a first domain comprising a first fluorescent agent having an absorption spectra;
(b) a second domain linked to said first domain and comprising a calcium-binding polypeptide;
(ii) said second chimeric polypeptide comprises:
(a) a first domain comprising a polypeptide which binds in a calcium-dependent manner to said calcium-binding polypeptide; and
(b) a second domain linked to said first domain of said second chimeric polypeptide and comprising a second fluorescent agent having an emission spectra which overlaps with the absorption spectra of said first fluorescent agent; or
wherein the intracellular calcium level is determined by measuring the intensity of the fluorescence emitted by said first fluorescent agent.

In an embodiment, the above-mentioned calcium-binding polypeptide is Calmodulin (CaM) or a calcium-binding fragment thereof.

In an embodiment, the above-mentioned polypeptide binding in a calcium-dependent manner to said calcium-binding polypeptide is myosin light chain kinase or a calmodulin-binding domain thereof. In a further embodiment, the above-mentioned calmodulin-binding domain of a myosin light chain kinase comprises a domain corresponding to residues 577 to 602 of rabbit skeletal muscle myosin light chain kinase (M13). In a further embodiment, the above-mentioned calmodulin-binding domain of a myosin light chain kinase comprises the amino acid sequence of SEQ ID NO: 14.

In an embodiment, the above-mentioned first fluorescent agent is a cyan fluorescent protein (CFP) and said second fluorescent agent is a yellow fluorescent polypeptide (YFP). In another embodiment, the above-mentioned first fluorescent agent is a yellow fluorescent polypeptide (YFP) and said second fluorescent agent is a cyan fluorescent protein (CFP).

In an embodiment, the above-mentioned second domain of said first chimeric polypeptide is linked to said first domain of said second chimeric polypeptide.

In an embodiment, the above-mentioned first and second chimeric polypeptides are recombinantly expressed as a single chimeric polypeptide. In a further embodiment, the above-mentioned single chimeric polypeptide comprises an amino acid sequence of a Cameleon polypeptide.

In an embodiment, the above-mentioned cell further comprises a second nucleic acid encoding the above-mentioned first and second chimeric polypeptides.

In another aspect, the present invention provides a kit comprising the above-mentioned cell and a container.

In another aspect, the present invention provides a kit comprising the above-mentioned vector and a container.

In another aspect, the present invention provides a kit comprising the above-mentioned vector, wherein said vector further comprises the above-mentioned second nucleic acid, and a container.

In another aspect, the present invention provides a kit comprising the above-mentioned vector, a second vector comprising the above-mentioned second nucleic acid, and a container.

In an embodiment, the above-mentioned kit further comprises instructions setting forth the above-mentioned method.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 3 shows representative confocal microscopy experiments involving the HEK293 Cameleon cell line.

FIG. 4 shows validation of the $Na_v1.5^{Mut}$/Cameleon stable cell lines.

Figure 6A:
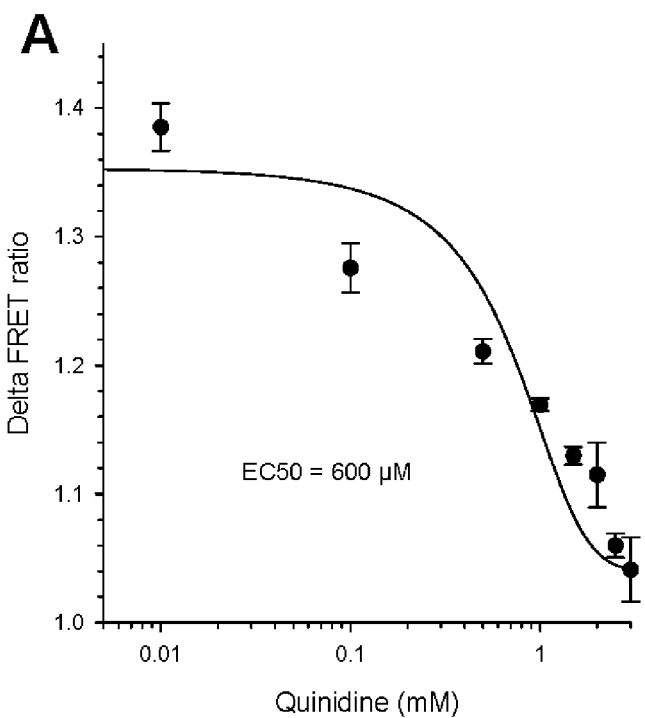
Figure 6B:
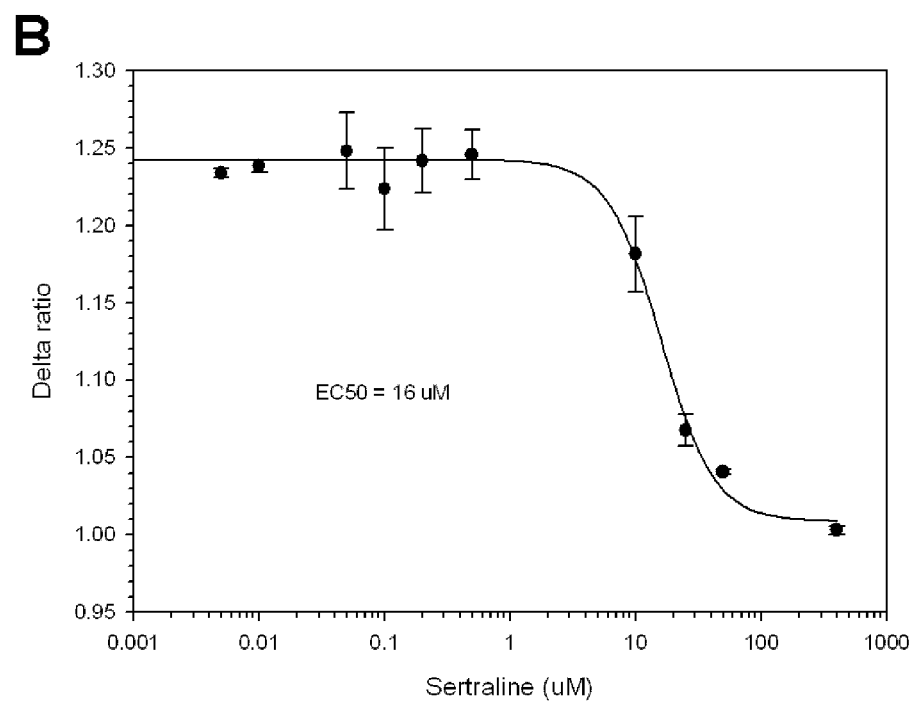
Figure 6C:
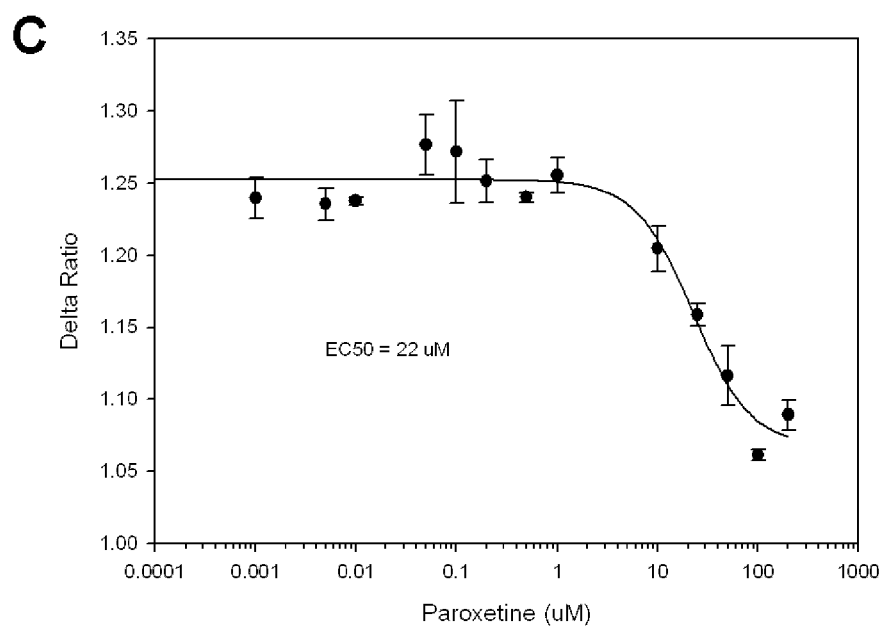

FIG. 6 shows dose-response measurements of FRET signal in the presence of a sodium channel blockers. VC/Na$_v$1.5 #12 cells were incubated with different concentrations of quinidine (FIG. 6A), sertralin (FIG. 6B) or paroxetine (FIG. 6C), and a first fluorescence reading was performed, ($F_{Venus}/F_{CFP})_0$. 25 mM $Ca^{2+}$ was added to activate the channel and a second fluorescence reading was performed, ($F_{Venus}/F_{CFP})_{ca2+}$. These results were obtained in fluorescence microplate assay with an excitation at 425 nm and emissions at 480 nm (for $F_{CFP}$) and 525 nm (for $F_{Venus}$) The results are represented as the Delta FRET ratio, which is ($F_{Venus}/F_{CFP})_{Ca2+}/(F_{Venus}/F_{CFP})_0$, as a function of sodium channel blocker concentration. Error bars represent the standard deviation of experiments performed in triplicate;

FIG. 7A shows the amino acid sequence of a mutated human Nav1.5 polypeptide (Na$_v$1.5$^{mut}$; SEQ ID NO: 5). The residues corresponding to the "DEKA" and "IFM" motifs are in bold and underlined, and the mutations relative to native human Nav1.5 are highlighted in grey (K to C at position 1419 and F to Q at position 1486); and FIGS. 7B-7E shows the amino acid sequences of various human Na$_v$1.5 alpha subunit polypeptides: Na$_v$1.5 isoform a (FIG. 7B; SEQ ID NO: 7), Na$_v$1.5 isoform b (FIG. 7C; SEQ ID NO: 9), Na$_v$1.5 isoform c (FIG. 7D; SEQ ID NO: 11), and Na$_v$1.5 isoform d (FIG. 7E; SEQ ID NO: 13). The residues corresponding to the "DEKA" and "IFM" motifs are in bold and underlined.

DISCLOSURE OF INVENTION

In the studies described herein, it is shown that cells expressing (i) a mutated Na$_v$1.5 channel having (a) an increased permeability for group IIA divalent cations (e.g., $Mg^{2+}$, $Ca^{2+}$, $Sr^{2+}$, $Ba^{2+}$) and (b) a decreased inactivation rate, and (ii) a reporter system sensitive to modulations in divalent cation concentrations, may be used to screen for compounds that modulate Na$_v$ channel activity.

Accordingly, in a first aspect, the present invention provides a mutated voltage gated sodium channel (Na$_v$) alpha subunit polypeptide comprising a first mutation that increases the permeability of the channel for a group IIA divalent cation and a second mutation that decreases the inactivation rate of the channel.

Figure 1:
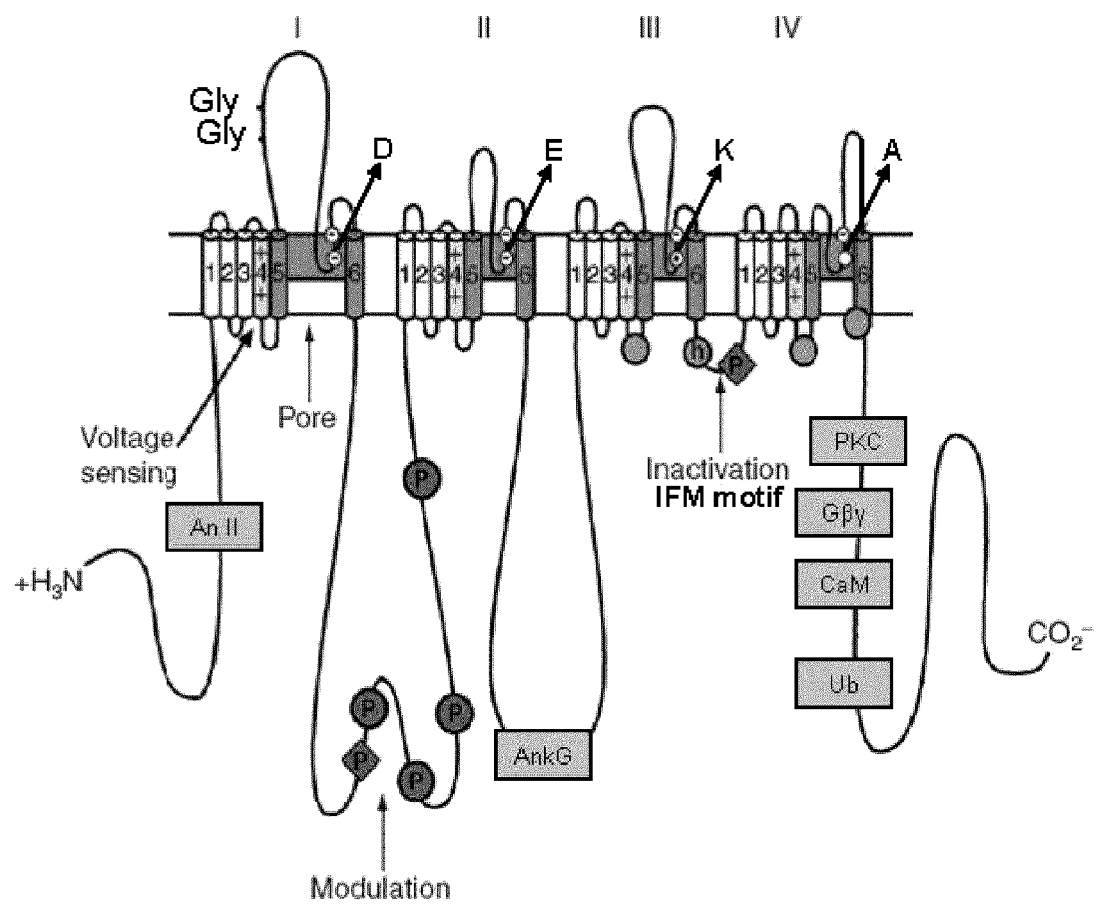
FIG. 1 shows the schematic representation of the general structure of the alpha (α) subunit of voltage-gated sodium channels. The a subunit folds into four domains (I to IV), each containing six α-helical transmembrane segments (1-6). Segments 5 and 6 are the pore-lining segments and the S4 helices, which contain positively charged amino acid residues in every third position, constitute the voltage sensors. "Gly" indicates putative N-linked glycosylation sites. The circles in the intracellular loops of domains III and IV indicate the inactivation gate "IFM" motif (h, inactivation gate). The "P" represent phosphorylation sites, with the circles representing sites for protein kinase A and the diamonds representing sites for protein kinase C. The location of the residues forming the aspartate-glutamate-lysine-alanine ("DEKA") ring are highlighted. An II=Annexin II; AnkG=Ankyrin G; CaM=Calmodulin; Gβγ=G-protein β-γ complex; Ub=Ubiquitin.

In an embodiment, the above-mentioned first mutation is a mutation in a domain connecting a S5 and a S6 α-helical transmembrane-spanning segment (see FIG. 1).

In an embodiment, the above-mentioned first mutation is:
  (i) a mutation at a residue corresponding to residue 372 in the amino acid sequence of isoform A of human Na$_v$1.5 alpha subunit;
  (ii) a mutation at a residue corresponding to residue 898 in the amino acid sequence of isoform A of human Na$_v$1.5 alpha subunit;
  (iii) a mutation at a residue corresponding to residue 1419 in the amino acid sequence of isoform A of human Na$_v$1.5 alpha subunit;
  (iv) a mutation at a residue corresponding to residue 1711 in the amino acid sequence of isoform A of human Na$_v$1.5 alpha subunit; or
  (v) any combination of (i) to (iv).

In an embodiment, the above-mentioned mutation at a residue corresponding to residue 1419 in the amino acid sequence of isoform A of human Na$_v$1.5 alpha subunit is a substitution to an alanine residue.

In an embodiment, the above-mentioned second mutation is a mutation in an intracellular region connecting the S6 α-helical transmembrane-spanning segment of Domain III and the S1 α-helical transmembrane-spanning segment of domain IV (see FIG. 1).

In an embodiment, the above-mentioned second mutation is:
  (i) a mutation at a residue corresponding to residue 1485 in the amino acid sequence of isoform A of human Na$_v$1.5 alpha subunit;
  (ii) a mutation at a residue corresponding to residue 1486 in the amino acid sequence of isoform A of human Na$_v$1.5 alpha subunit;
  (iii) a mutation at a residue corresponding to residue 1487 in the amino acid sequence of isoform A of human Na$_v$1.5 alpha subunit; or
  (iv) any combination of (i) to (iii).

Correspondence of amino acid positions described herein is frequently expressed in terms of the positions of the amino acids of isoform A of the human Na$_v$1.5 alpha subunit polypeptide set forth in FIG. 7A (also called hH1, Gellens et al., Proc. Natl. Acad. Sci. USA 89: 554-558). For example, the positions correspond to one or more of the amino acids aspartic acid (D), glutamic acid (E), lysine (K) and alanine (A) ("DEKA" motif) set forth at positions 372, 898, 1419 and 1711, respectively, in the amino acid sequence depicted in FIG. 7A, or to one or more of the amino acids isoleucine (I), phenylalanine (F), and methionine (M) ("IFM" motif) set forth at positions 1485, 1486 and 1487, respectively, in the amino acid sequence depicted in FIG. 7A. A "mutated" or "modified" Na$_v$ alpha subunit polypeptide as used herein refers to a polypeptide having voltage-gated ion channel activity (e.g., a truncated form of a Na$_v$ alpha subunit polypeptide, a fusion polypeptide having voltage-gated ion channel activity, a chimeric polypeptide having ion channel activity, etc.), the polypeptide having (i) a different amino acid from the native protein at at least one of the amino acid positions described more fully in the specification, in relation to a wild-type or native Na$_v$ polypeptide, (ii) an increased permeability for a group IIA divalent cation (e.g., $Mg^{2+}$, $Ca^{2+}$, $Sr^{2+}$, $Ba^{2+}$) relative to a native Na$_v$ polypeptide and (iii) a decreased inactivation rate relative to a native Na$_v$ polypeptide.

"Mutated" or "mutation" as used herein, for example in reference to a polypeptide or nucleic acid, refers to an altered version or alteration therein, relative to the native, naturally occurring (typically referred to as "wild-type") version of the polypeptide or nucleic acid. Mutations include for example substitution(s), insertion(s) and/or deletions of residue(s) (amino acid or nucleotide, as applicable) in a polypeptide or nucleic acid sequence.

Voltage-dependent sodium channels have been identified in a variety of animals, including flies, leeches, squid and jellyfish, as well as mammalian and non-mammalian vertebrates. These various channels share significant homology, particularly in the transmembrane and extracellular domains. For example, the mammalian sodium channel isoforms that have been identified and functionally expressed are all greater than 50% identical in amino acid sequence in the transmembrane and extracellular domains. More particularly, the "DEKA" and "IFM" motifs noted above are highly conserved among the various Na$_v$ channels. It will be understood that amino acid numbering can thus be shifted in situations where the residues corresponding to DEKA and IFM residues in isoform A of the human $Na_v1.5$ alpha subunit polypeptide are within a polypeptide having more or fewer amino acids N-terminal to the region(s) where these residues reside, relative to isoform A of the human $Na_v1.5$ alpha subunit polypeptide, thereby resulting in different amino acid numbering relative to the positions of isoform A of the human $Na_v1.5$ alpha subunit polypeptide. The corresponding positions may be easily identified, for example by aligning the amino acid sequence of a given $Na_v$ alpha subunit polypeptide with that of isoform A of the human $Na_v1.5$ alpha subunit polypeptide (e.g., using a software for sequence alignment such as Clustal W). For example, the positions corresponding to positions 372, 898, 1419 and 1711 of isoform A of the human $Na_v1.5$ alpha subunit polypeptide in other isoforms of human $Na_v1.5$ alpha subunit channels (FIG. 7C-7E) are depicted in Table I below, and the positions corresponding to positions 1485, 1486 and 1487 of isoform A of the human $Na_v1.5$ alpha subunit polypeptide in other isoforms of human $Na_v1.5$ alpha subunit channels are depicted in Table II below.

TABLE I

Positions corresponding to positions 372, 898, 1419 and 1711 of isoform A of the human $Na_v1.5$ alpha subunit polypeptide in other isoforms of human $Na_v1.5$ alpha subunit channels

| Sodium Channel | Position corresponding to position 372 of isoform A of human $Na_v1.5$ alpha subunit polypeptide | Position corresponding to position 898 of isoform A of human $Na_v1.5$ alpha subunit polypeptide | Position corresponding to position 1419 of isoform A of human $Na_v1.5$ alpha subunit polypeptide | Position corresponding to position 1711 of isoform A of human $Na_v1.5$ alpha subunit polypeptide |
|---|---|---|---|---|
| Human $Na_v1.5$, isoform b | 372 | 898 | 1418 | 1710 |
| Human $Na_v1.5$, isoform c | 372 | 898 | 1419 | 1711 |
| Human $Na_v1.5$, isoform d | 372 | 898 | 1399 | 1693 |

TABLE II

Positions corresponding to positions 1485, 1486 and 1487 of isoform A of the human $Na_v1.5$ alpha subunit polypeptide in other isoforms of human $Na_v1.5$ alpha subunit channels

| Sodium Channel | Position corresponding to position 1485 of isoform A of human $Na_v$ 1.5 alpha subunit polypeptide | Position corresponding to position 1486 of isoform A of human $Na_v$ 1.5 alpha subunit polypeptide | Position corresponding to position 1487 of isoform A of human $Na_v$ 1.5 alpha subunit polypeptide |
|---|---|---|---|
| Human $Na_v1.5$, isoform b | 1484 | 1485 | 1486 |
| Human $Na_v1.5$, isoform c | 1485 | 1486 | 1487 |
| Human $Na_v1.5$, isoform d | 1467 | 1468 | 1469 |

In another aspect, the present invention provides a nucleic acid encoding the above-mentioned mutated $Na_v$ alpha subunit polypeptide.

The invention further provides a variant or fragment of the above-noted polypeptide, the variant or fragment comprising the above-noted mutations at positions corresponding to positions 372, 898, 1419, 1485, 1486, 1487 and 1711 of isoform A of the human Nav1.5 alpha subunit polypeptide noted above, the variant or fragment further having an increased permeability for a group IIA divalent cation (e.g., $Mg^{2+}$, $Ca^{2+}$, $Sr^{2+}$, $Ba^{2+}$) and a decreased inactivation rate (relative to a corresponding variant or fragment of a $Na_v$ polypeptide lacking the above-noted mutations). In an embodiment, the above-mentioned variant is a splice variant. Known splice variants of $Na_v$ alpha subunit nucleic acids are described in Chahine et al. (*CNS & Neurological Disorders—Drug Targets,* 2008, 7:144-158).

In another aspect, the present invention provides a nucleic acid encoding the above-mentioned mutated $Na_v$ alpha subunit polypeptide, or variant or fragment thereof.

The nucleic acid of the present invention includes those sequences that, because of the degeneracy of the genetic code, encode the amino acid sequence of any of the $Na_v$ alpha subunit mutant polypeptides described herein. In an embodiment, the above-mentioned nucleic acid comprises the nucleotide sequence of SEQ ID NO: 1, 2, 3 or 4.

Mutagenesis can be performed utilizing any one of several techniques known to those of skill in the art (see for example, Jeff Braman, in In Vitro Mutagenesis Protocols, $2^{nd}$ edition (2002), Humana Press, 304 pages). Moreover, kits for site-directed mutagenesis are commercially available, such as Quikchange™ Site-Directed Mutagenesis Kit from Stratagene, GeneTailor™ Site-Directed Mutagenesis System from Invitrogen, Altered Sites™ in vitro Mutagenesis System from Promega.

Various genes and nucleic acid sequences of the invention may be recombinant sequences. Further, polypeptides or proteins of the invention may also be recombinant. The term "recombinant" means that something has been recombined, so that when made in reference to a nucleic acid the term refers to a molecule that is comprised of nucleic acid sequences that are joined together or produced by means of molecular biological techniques. The term "recombinant" when made in reference to a protein or a polypeptide refers to a protein or polypeptide molecule, which is expressed using a recombinant nucleic acid construct created by means of molecular biological techniques. The term "recombinant" when made in reference to genetic composition refers to a gamete or progeny or cell or genome with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

In accordance with the present invention, an isolated polynucleotide, or an isolated nucleic acid molecule, is a nucleic acid molecule that has been removed from its natural milieu (i.e., that has been subjected to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecules can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

"Homology" and "homologous" refer to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid or polypeptide sequence is "homologous" to another sequence if the two sequences are substantially identical and the functional activity of the sequences is conserved (as used herein, the term 'homologous' does not infer evolutionary relatedness). Two nucleic acid or polypeptide sequences are considered "substantially identical" if, when optimally aligned (with gaps permitted), they share at least about 50% sequence similarity or identity and/or if the sequences share defined functional motifs. In alternative embodiments, sequence similarity in optimally aligned substantially identical sequences may be at least 60%, 70%, 75%, 80%, 85%, 90% or 95% with any of the polypeptide or nucleic acid sequences of the invention. As used herein, a given percentage of homology between sequences denotes the degree of sequence identity in optimally aligned sequences. An "unrelated" or "non-homologous" sequence shares less than 40% identity, though preferably less than about 25% identity, with any of the polypeptide or nucleic acid sequences of the invention. "Substantially complementary" nucleic acids are nucleic acids in which the complement of one molecule is substantially identical to the other molecule.

Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48: 443, the search for similarity method of Pearson and Lipman, 1988, Proc. Natl. Acad. Sci. USA 85: 2444, and the computerised implementations of these algorithms (such as GAP, BEST-FIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, J. Mol. Biol. 215: 403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

In embodiments, the invention further provides polypeptides that are purified, isolated or substantially pure. A compound is "substantially pure" when it is separated from the components that naturally accompany it. Typically, a compound is substantially pure when it is at least 60%, more generally 75% or over 90%, by weight, of the total material in a sample. Thus, for example, a polypeptide that is chemically synthesized or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by extraction from a natural source; by expression of a recombinant nucleic acid molecule encoding a polypeptide; or by chemical synthesis. Purity can be measured using any appropriate method such as column chromatography, gel electrophoresis, HPLC, etc.

In another aspect, the present invention provides a vector (e.g., a recombinant vector) comprising the above-mentioned nucleic acid.

The recombinant expression vector of the present invention can be constructed by standard techniques known to one of ordinary skill in the art and found, for example, in Sambrook et al. (1989) in Molecular Cloning: A Laboratory Manual; and Sambrook and Russell (2001) Molecular Cloning: A Laboratory Manual ($3^{rd}$ edition; Cold Spring Harbor Laboratory). A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation. In addition, the vectors of the present invention may comprise a sequence of nucleotides for one or more restriction endonuclease sites. Coding sequences such as for reporter genes are well known to persons skilled in the art. In an embodiment, the vector further comprises one or more gene(s) of interest.

A recombinant expression vector comprising a nucleic acid sequence of the present invention may be introduced into a cell, e.g., a host cell, which may include a living cell capable of expressing the protein coding region from the defined recombinant expression vector. Accordingly, the invention also provides host cells, such as isolated host cells, containing the nucleic acid or recombinant expression vector of the invention. The terms "cells", "host cell" and "recombinant host cell" are used interchangeably herein. Such terms refer not only to the particular subject cell, but also to the progeny or potential progeny of such a cell. Because certain modifications may occur in succeeding generations due to either mutation or environmental influences, such progeny may not, in fact, be identical to the parent cell, but are still included within the scope of the term as used herein.

Vectors can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), Sambrook and Russell (supra) and other laboratory manuals. Methods for introducing nucleic acids into mammalian cells in vivo are also known, and may be used to deliver the vector DNA of the invention to a subject for gene therapy.

Suitable host cells and methods for recombinant expression of proteins are well known in the art. For example, eukaryotic host cells such as mammalian cells may be used (e.g., rodent cells such as mouse, rat and hamster cell lines, human cell/cell lines). In an embodiment, the above-mentioned cell does not naturally (or endogenously) express a voltage-gated sodium channel. In another embodiment, the above-mentioned cell is a human embryonic kidney cell (e.g., HEK293 cells).

In another aspect, the present invention provides a method for determining whether a test compound modulates the activity of a voltage gated sodium channel, said method comprising (a) providing a cell expressing the above-mentioned mutated $Na_v$ alpha subunit polypeptide; and (b) determining the intracellular level of a group IIA divalent cation (e.g., $Mg^{2+}$, $Ca^{2+}$, $Sr^{2+}$, $Ba^{2+}$) in said cell in the presence or absence of said test compound, wherein a difference in the intracellular level of said group IIA divalent cation in the presence relative to the absence of said test compound is indicative that said test compound modulates the activity of a voltage gated sodium channel.

In an embodiment, the above-mentioned method comprises providing a source of said group IIA divalent cation in the extracellular medium. Such source of divalent cation may be a solution comprising a chemical compound (e.g., a salt) comprising the divalent cation of interest. For example, a source of calcium ($Ca^{2+}$) may be a solution comprising a suitable amount of calcium chloride ($CaCl_2$). In an embodiment, the above-mentioned group IIA divalent cation is calcium ($Ca^{2+}$).

Methods and reagents for measuring intracellular ions levels are well known in the art. For example, methods and reagents for detecting intracellular magnesium ($Mg^{2+}$) levels are described in U.S. Patent publications Nos. 20090286275, 20090155837 and 20080293088. Similarly, methods and reagents for measuring intracellular $Ca^{2+}$ levels are well known in the art.

For example, fluorescent indicator compounds suitable for measuring intracellular calcium levels include various calcium indicator dyes (e.g., fluo-3, fura-2, fluo-4, fluo-5, calcium green-1, Oregon green, 488 BAPTA, SNARF-1, and indo-1; see Velicelebi et al., 1999, *Meth. Enzymol.* 294: 20-47).

Calcium indicator dyes are substances which show a change in a fluorescent characteristic upon binding calcium, e.g., greatly increased intensity of fluorescence and/or a change in fluorescent spectra (i.e., a change in emission or excitation maxima). Fluo-3, fura-2, and indo-1 are commonly used calcium indicator dyes that were designed as structural analogs of the highly selective calcium chelators ethylene glycol-bis(.beta.-aminoethyl ether) N,N,N',N'-tetraacetic acid (EGTA) and 1,2-bis(2-aminophenoxy) ethane-N,N,N', N'-tetraacetic acid (BAPTA). The fluorescence intensity from fluo-3 increases by more than 100-fold upon binding of calcium. While the unbound dye exhibits very little fluorescence, calcium-bound fluo-3 shows strong fluorescence emission at 526 nm. Fura-2 is an example of a dye that exhibits a change in its fluorescence spectrum upon calcium binding. In the unbound state, fura-2 has an excitation maximum of 362 nm. This excitation maximum shifts to 335 nm upon calcium binding, although there is no change in emission maximum. Binding of calcium to fura-2 can be monitored by excitation at the two excitation maxima and determining the ratio of the amount of fluorescence emission following excitation at 362 nm compared to the amount of fluorescence emission following excitation at 335 nm. A smaller ratio (i.e., less emission following excitation at 362 nm) indicates that more fura-2 is bound to calcium, and thus a higher internal calcium concentration in the cell.

The use of calcium indicator dyes entails loading cells with the dye, a process which can be accomplished by exposing cells to the membrane-permeable acetoxymethyl esters of the dyes. Once inside the plasma membrane of the cells, intracellular esterases cleave the esters, exposing negative charges in the free dyes. This prevents the free dyes from crossing the plasma membrane and thus leaves the free dyes trapped in the cells. Measurements of fluorescence from the dyes are then made, the cells are treated in such a way that the internal calcium concentration is changed (e.g., by exposing cells to an activator or inhibitor of a voltage-gated ion channel), and fluorescence measurements are again taken.

Fluorescence from the indicator dyes can be measured with a luminometer or a fluorescence imager. One preferred detection instrument is the Fluorometric Imaging Plate Reader (FLIPR) (Molecular Devices, Sunnyvale, Calif.). The FLIPR is well suited to high throughput screening using the methods of the present invention as it incorporates integrated liquid handling capable of simultaneously pipetting to 96 or 384 wells of a microtiter plate and rapid kinetic detection using a argon laser coupled to a charge-coupled device imaging camera.

One skilled in the art would be able to optimize experimental parameters (cell number, dye concentration, dye loading time, temperature of incubations, cell washing conditions, and instrument settings, etc.) by routine experimentation depending on the particular relevant experimental variables (e.g., type of cell used, identity of dye used). Several examples of experimental protocols that can be used are described in Velicelebi et al., 1999, supra.

In particular embodiments, the change in fluorescent characteristic is an increase in intensity of a fluorescence emission maximum. In other embodiments, the change in fluorescent characteristic is a shift in the wavelength of an absorption maximum. It is understood in the art that absorption of radiation results in the excitation of fluorescent molecule, and the terms "absorption" and "excitation", for example in respect of spectra, wavelengths, and maxima, are used interchangeably herein.

In an embodiment, the cells naturally express the mutated voltage-gated ion channel of interest. In another embodiment, the cells have been transfected (or transformed) with an expression vector that encode the voltage-gated ion channel of interest so that the cells recombinantly express the voltage-gated ion channel of interest. Transfection is meant to include any method known in the art for introducing nucleic acids such as expression vectors into the cells. For example, transfection includes calcium phosphate or calcium chloride mediated transfection, lipofection, infection with a retroviral construct, and electroporation.

Another way to measure ion flow indirectly is to monitor changes in transcription that result from the activity of voltage-gated ion channels by the use of transcription based assays. Transcription-based assays involve the use of a reporter gene whose transcription is driven by an inducible promoter whose activity is regulated by a particular intracellular event such as, e.g., changes in intracellular calcium levels, that are caused by the activity of a voltage-gated ion channel. Transcription-based assays are reviewed in Rutter et al., 1998, *Chemistry & Biology* 5: R285-R290. Transcription-based assays of the present invention rely on the expression of reporter genes whose transcription is activated or repressed as a result of intracellular events that are caused by the interaction of a activator or inhibitor with a voltage-gated ion channel.

In an embodiment, the intracellular calcium level is determined by determining the conformational change of a calcium-binding polypeptide.

As used herein, the term "calcium-binding polypeptide" refers to a polypeptide that binds one or more calcium ions and which undergoes a conformational change upon calcium binding. Examples of calcium-binding polypeptides include, for example, Calmodulin (CaM) as well as proteins known as Calmodulin-like proteins such as aequorin, Calcium-binding protein (CABP), Calcineurin B subunit isoform 1, Calmodulin-related protein NB-1 (CLP), Calcium vector protein (CAVP), Guanylyl cyclase activating protein 3 (GCAP 3), Calcium and integrin-binding protein 1 (Calmyrin; KIP; CIB), Myosin-2 light chain, Myosin essential light chain striated adductor muscle (E-LC), Myosin regulatory light chain striated adductor muscle (R-LC), Myosin regulatory light chain cdc4, Neurocalcin delta, Neuronal calcium sensor 1 (Frequenin), Sarcoplasmic calcium-binding protein (SCP), Troponin C, and any calcium-binding fragment of the above-mentioned proteins. Therefore, any assay (e.g., fluorescent-based, enzymatic-based) which permits to measure the level/extent of conformational change of a calcium-binding polypeptide may be used in the method of the present invention.

For example, the intracellular calcium level may be measured using the aequorin system. The aequorin system makes use of the protein apoaequorin, which binds to the lipophilic chromophore coelenterazine forming a combination of apoaequorin and coelenterazine that is known as aequorin. Apoaequorin has three calcium binding sites and, upon calcium binding, the apoaequorin portion of aequorin changes its conformation. This change in conformation causes coelenterazine to be oxidized into coelenteramide, $CO_2$, and a photon of blue light (466 nm). This photon can be detected with suitable instrumentation. Reagents to analyze intracellular calcium levels based on the aequorin system are commercially available. For example, recombinant aequorin (AquaLite®, Cat. No. A-6785) as well as coelenterazine and derivatives thereof (e.g., Cat. Nos. C-2944, C-14261, C-14261, C-6779 and C-6780) may be purchased at Invitrogen/Molecular Probes.

In an embodiment, the above-mentioned calcium-binding polypeptide is calmodulin (CaM) or a calcium-binding fragment thereof. Calmodulin is an intracellular calcium receptor found ubiquitously in eukaryotes. It is capable of regulating biological activities of many cellular proteins and transmembrane ion transporters mainly in a $Ca^{2+}$-dependent manner. When the intracellular calcium level rises to a certain level, four $Ca^{2+}$ ions bind to calmodulin, and the $Ca^{2+}$-calmodulin complex binds the target proteins (e.g., skeletal muscle myosin light chain kinase, smooth muscle myosin light chain kinase, calmodulin-dependent kinase II), initiating various signalling cascades. Therefore, intracellular calcium levels may be measured, for example, by assessing the level of binding of a target protein to CaM, or by assessing the activation of a signalling cascade which depends on the CaM activation. For example, the binding of calcium ions to CaM allows CaM to bind to cyclic nucleotide phosphodiesterases and to adenyl cyclase with subsequent activation, thereby increasing cyclic AMP and cyclic GMP levels. Therefore, an increase in intracellular calcium levels may be measured indirectly by determining cyclic AMP and/or cyclic GMP levels in a cell.

As noted above, calcium-binding polypeptides bind one or more calcium ions and generally undergo conformational change upon calcium binding. This conformational allows, in turn, the interaction with other proteins in a calcium-dependent manner. As such, a modulation in intracellular $Ca^{2+}$ levels may be measured by determining the extent of binding between a calcium-binding polypeptide and a ligand or protein that binds to the calcium-binding polypeptide in a calcium-dependent manner (i.e., upon calcium-induced conformational change in the calcium-binding polypeptide). Therefore, any combination of a calcium-binding polypeptide with a ligand/polypeptide that binds to the calcium-binding polypeptide in a calcium-dependent manner may be used in the method of the present invention.

In an embodiment, the above-mentioned calcium-binding polypeptide is calmodulin (CaM) or a calcium-binding fragment thereof, and the intracellular calcium levels is determined by assessing the binding of a calcium-dependent calmodulin-binding protein to CaM (or to a calcium-binding fragment thereof). Examples of calcium-dependent calmodulin-binding proteins include, for example, peripheral plasma membrane protein CASK, Elongation factor 2 kinase, Calcium/calmodulin-dependent protein kinase type I, Calcium/calmodulin-dependent protein kinase type IV catalytic chain, Calcium/calmodulin-dependent protein kinase type II alpha chain, Myosin light chain kinase/smooth muscle and non-muscle isozymes, Phosphorylase B kinase alpha regulatory chain/skeletal muscle isoform, Calcineurin B subunit isoform 1, $Ca^{2+}$/calmodulin-dependent protein kinase phosphatise, Serine/threonine protein phosphatase 2B catalytic subunit alpha isoform, Cysteinyl leukotriene receptor 2, Adenylate cyclase type I, brain Nitric-oxide synthase, Inositol-trisphosphate 3-kinase A, Caldesmon, Dystrophin, Myristoylated alanine-rich C-kinase substrate, Alpha-1-syntrophin, erythrocyte Spectrin alpha chain and brain Spectrin alpha chain.

In an embodiment, the above-mentioned calcium-dependent calmodulin binding protein is myosin light chain kinase or a calmodulin-binding domain thereof. In a further embodiment, the above-mentioned calmodulin-binding domain of a myosin light chain kinase comprises a domain corresponding to residues 577 to 602 of rabbit skeletal muscle myosin light chain kinase (generally referred to as M13, KRRWKKNFIAVSAANRFKKISSSGAL, SEQ ID NO: 14). In a further embodiment, the above-mentioned calmodulin-binding domain of a myosin light chain kinase comprises the amino acid sequence of SEQ ID NO: 14.

In another embodiment, the above-mentioned cell expressing a mutated $Na_v$ alpha subunit polypeptide further expresses a first and second marker polypeptide, wherein
 (i) said first marker polypeptide comprises:
  (a) a first domain comprising a first agent having an energy emission spectrum;
  (b) a second domain linked to said first domain and comprising a calcium-binding polypeptide;
 (ii) said second marker polypeptide comprises:
  (a) a first domain comprising a polypeptide binding in a calcium-dependent manner to said calcium-binding polypeptide; and
  (b) a second domain linked to said first domain of said second marker polypeptide and comprising a second agent having an absorption spectrum which overlaps with the emission spectrum of said first agent;
wherein the intracellular calcium level is determined by measuring the intensity of the emission emitted by said second agent.

In another embodiment, the above-mentioned cell expressing a mutated $Na_v$ alpha subunit polypeptide further expresses a first and second fluorescent polypeptide, wherein
 (i) said first fluorescent polypeptide comprises:
  (a) a first domain comprising a first fluorescent agent having an emission spectrum;
  (b) a second domain linked to said first domain and comprising a calcium-binding polypeptide;
 (ii) said second fluorescent polypeptide comprises:
  (a) a first domain comprising a polypeptide binding in a calcium-dependent manner to said calcium-binding polypeptide; and
  (b) a second domain linked to said first domain of said second polypeptide and comprising a second fluorescent agent having an absorption spectrum which overlaps with the emission spectrum of said first fluorescent agent;
wherein the intracellular calcium level is determined by measuring the intensity of the fluorescence emitted by said second fluorescent agent.

As noted above, any combination of a calcium-binding polypeptide (second domain of the first chimeric polypeptide) with a polypeptide that binds to the calcium-binding polypeptide in a calcium-dependent manner (first domain of the second chimeric polypeptide) may be used in the method of the present invention.

In an embodiment, the calcium-binding polypeptide is calmodulin or a calcium binding fragment thereof, and the first domain of the second chimeric polypeptide comprises a calcium-dependent calmodulin-binding polypeptide, such as those described above.

The first and second fluorescent agents are selected according to their characteristic absorption and emission spectra. The excitation energy of the first fluorescent agent (the donor) is transferred to the second fluorescent agent (the acceptor) by dipolar interactions, without donor fluorescence emission. This is generally referred to as Fluorescence Resonance Energy Transfer (FRET). The donor emission and acceptor absorption spectra should overlap for FRET to occur, and therefore any combination of fluorescent agents having overlapping emission/absorption spectra may be used in the method of the present invention. Combinations of fluorescent agents that are suitable for FRET-based experiments are well-known in the art. In embodiments, the configuration of the above-noted first and second polypeptides may be modified such that the above-noted agent having an emission spectrum and agent having an absorption spectrum are reversed, i.e., such that the first (fluorescent) polypeptide comprises a first domain comprising a first (fluorescent) agent having an absorption spectrum, and the second (fluorescent) polypeptide comprises a second domain comprising a second (fluorescent) agent having an emission spectrum which overlaps with the absorption spectrum of the first (fluorescent) agent. "Overlap" as used in the context of fluorescent spectra refers to the ability of the emitted light from a fluorophore to be of a wavelength capable of excitation of another fluorophore.

In an embodiment, the above-mentioned fluorescent agent is a polypeptide comprising a fluorescent protein, such as the Green Fluorescent Protein (GFP) as well as all derivatives thereof such as Blue Fluorescent Protein (BFP), Red Fluorescent Protein (RFP), Yellow Fluorescent Protein (YFP), Cyan Fluorescent Protein (CFP). Fluorescent polypeptide pairs that are suitable for FRET-based experiments include, for example, CFP and YFP (or a modified YFP called Venus) as well as BFP and GFP.

In an embodiment, the above-mentioned first fluorescent agent is a cyan fluorescent protein (CFP) and said second fluorescent agent is a yellow fluorescent polypeptide (YFP).

In an embodiment, the above-mentioned first fluorescent agent is a yellow fluorescent polypeptide (YFP) and said second fluorescent agent is a cyan fluorescent protein (CFP).

In an embodiment, the above-mentioned CFP comprises the following mutations relative to wild-type GFP: F64L/S65T/Y66W/N146I/M153T/V163A/N164H. In an embodiment, the above-mentioned YFP comprises the following mutations relative to wild-type GFP: S65G/S72A/T203Y. In an embodiment, the above-mentioned YFP comprises the following mutations relative to wild-type GFP: S65G/V68L/Q69K/S72A/T203Y (see, for example, Miyawaki et al., *Proc Natl Aced Sci USA*. 1999, 96: 2135-2140).

In cases where the fluorescent agent is a polypeptide comprising a fluorescent protein, the first and/or second fluorescent polypeptide(s) may be recombinantly expressed as a chimeric polypeptide. For example, a cell may comprise a nucleic acid encoding a fluorescent protein may be linked to a nucleic acid encoding a calcium-binding polypeptide (or a polypeptide binding in a calcium-dependent manner to a calcium-binding polypeptide), for expression of a chimeric polypeptide comprising the fluorescent protein and the calcium-binding polypeptide (or the polypeptide binding in a calcium-dependent manner to a calcium-binding polypeptide) covalently linked to each other.

In another embodiment, the above-mentioned first and second fluorescent polypeptides are recombinantly expressed as a chimeric polypeptide. For example, the second domain of the first fluorescent polypeptide may be linked to the first domain of the second fluorescent polypeptide, and thus the four domains are linked to each other and expressed as a single chimeric polypeptide. An example of such a chimeric system is the Cameleon calcium sensor system.

The Cameleon molecule comprises four domains. The Cameleon is a fusion product between two fluorescent proteins (having differing excitation and emission characteristics), calmodulin (CaM), and the calmodulin-binding domain of rabbit myosin light chain kinase (M13). Calmodulin is capable of binding with free calcium ions and the M13 chain can bind with calmodulin after it has bound the calcium ions. The nucleic acids encoding these four proteins are joined linearly, and the fusion nucleic acid may be expressed in a variety of cells. Fluorescent proteins are located at both ends of the chimera and thus stand away from each other in the absence of calcium ion. But in the presence of calcium ions, the activated CaM linker wraps around the M13 protein. The tertiary structure of the Cameleon chimera is then altered to bring the two fluorescent protein moieties closer to each other and thus increases the efficiency of energy transfer (e.g., FRET).

The binding of calcium by the calmodulin moiety of Cameleon produces a conformational change of the entire molecule, which positions the two fluorescent proteins into close spatial proximity. In this conformation, dipolar energy transfer by the excited first fluorescent protein (e.g., CFP) protein stimulates the second fluorescent protein (e.g., YFP, or a modified YFP called Venus (Nagai T. et al., *Nat. Biotechnol.* 2002, 20: 87-90)) to produce secondary fluorescence having a wavelength that is different than the wavelength of the fluorescence emitted by the first fluorescent protein. In such a system, intracellular calcium ion concentration can be determined by fluorescence ratio imaging as the ratio of the changes in two types of fluorescence (i.e., the fluorescence emitted by the first fluorescent protein versus that emitted by the second fluorescent protein). An increase in the fluorescence emitted by the second fluorescent protein versus that emitted by the first fluorescent protein is indicative that FRET occurs, and thus that the level of intracellular calcium is increased.

The above-mentioned methods may be employed either with a single test compound or a plurality or library (e.g., a combinatorial library) of test compounds. In the latter case, synergistic effects provided by combinations of compounds may also be identified and characterized. The above-mentioned compounds may be used for prevention and/or treatment of diseases associated with abnormal activity of a voltage-gated sodium channel (or in which modulation of voltage-gated sodium channel activity would be beneficial), or may be used as lead compounds for the development and testing of additional compounds having improved specificity, efficacy and/or pharmacological (e.g., pharmacokinetic) properties. In an embodiment the compound may be a prodrug which is altered into its active form at the appropriate site of action, (e.g., a cell, tissue or organ in which abnormal activity of a voltage-gated sodium channel is observed, such as a central nervous system (CNS) cell, tissue or organ). In certain embodiments, one or a plurality of the steps of the screening/testing methods of the invention may be automated. Such methods may be performed in an array format.

There are several diseases/conditions associated with abnormal activity of a voltage-gated sodium channel (general referred to as channelopathies). For example, mutations in the gene encoding $Na_v1.5$ cause various diseases/conditions such as inherited long QT syndrome type 3, Brugada syndrome, conduction disease, sinus node dysfunction, and atrial standstill, which lead to an increased risk of ventricular arrhythmias (Remme C A et al., *Trends Cardiovasc Med.* 2008, 18(3): 78-87).

As such, the screening methods of the present invention may be useful for identifying compounds that may be used for the prevention and/or treatment of one or more of the above-mentioned diseases/conditions, or any other disease/condition associated with aberrant voltage-gated sodium channel function. Accordingly, in another aspect, the present invention provides a compound identified by the above-mentioned method, as well as the use of such compounds for the prevention and/or treatment of disease/condition associated with aberrant voltage-gated sodium channel function.

In an embodiment, the above-mentioned chimeric polypeptide comprises the amino acid sequence of a Cameleon polypeptide.

In another aspect, the present invention provides a cell comprising (a) the above-mentioned mutated $Na_v$ alpha subunit polypeptide and (b) the above-mentioned first and second polypeptides.

In another aspect, the present invention provides a kit comprising the above-mentioned cell and a container. In another aspect, the present invention provides a kit comprising the above-mentioned vector and a container. Such kit may further comprise, for example, instructions for determining whether a test compound modulates the activity of a voltage gated sodium channel, control samples, reagents useful for performing the methods (e.g., buffers, enzymes, transfection reagents, detection reagents), host cells, etc.

MODE(S) FOR CARRYING OUT THE INVENTION

The present invention is illustrated in further details by the following non-limiting examples.

Example 1

Materials and Methods

Site-Directed Mutagenesis.

Site-directed mutations to wild-type human $Na_v1.5$ was made using the QuickChange™ Site-directed Mutagenesis Kit according to the manufacturer instructions (Stratagene Inc., La Jolla, Calif.). Base substitutions were confirmed by automatic DNA sequencing at the CHUL Research Centre DNA sequencing facility (Québec, Québec).

Transient Expression of Na Channels in HEK293 Cells.

A standard calcium phosphate precipitation procedure was used to transfect the cDNA of the wild-type and mutant $Na_v1.5$ channel (cloned into the pCDNA3neo vector) into HEK293 cells. For transfection, $Na_v1.5$ DNA (10 µg) was mixed with 10 µg of EBO plasmid encoding for the CD8 antigen and 0.5 ml of 250 mM $CaCl_2$. This mixture was then slowly added to 0.5 ml of 2× HeBS solution comprising (in mM): 275 NaCl, 40 Hepes, 12 dextrose, 10 KCl, 1.4 $Na_2HPO_4$, pH 7.5. This mixture was incubated 20 minutes at room temperature then slowly added to a 100 mm culture dish of 50% confluent HEK293 cells bathed in 10 ml of DMEM (Gibco) enriched with 10% fetal bovine serum and 1% penicillin-streptomycin. After 12 hours of incubation the cells were washed and replated on 35 mm culture dishes. Currents were recovered within 12-24 hours of plating.

Establishment of Reporter Cell Lines.

The reporter cell lines described herein are derived from the HEK293 cell line, which, in turn, is derived from human embryonic kidney. HEK293 cells are of human origin, display high cell division efficiency and do not express significant endogenous sodium channels. To generate a $Na_v1.5^{Mut}$/Cameleon reporter cell line, the first step was to establish a HEK293 cell line which expresses the Cameleon calcium biosensor alone. HEK293 cells were transfected with a vector (pIREShyg3, Clonetech, Cat. No. 631620) encoding the Cameleon construct (as described in Evanko and Haydon, *Cell Calcium* (2005) 37: 341-348). This cell line that express the Cameleon alone was then stably transfected with the pcDNA4neo-$Na_v1.5^{Mut}$ expression vector (see FIG. 7A for the sequence of $Na_v1.5^{Mut}$). After two weeks of selection with hygromycin to eliminate the cells that do not express the vector, the resulting cell colonies were transferred to a 96, 48, 24, 12 and 6 wells culture plates for amplification. The resulting cell lines were then assessed in patch-clamp for their capacity to produce robust current amplitude.

Whole-Cell Patch Clamp Recording.

Whole-cell Na current recordings were obtained using an Axopatch™ 200A patch clamp amplifier equipped with a DigiData™ 1200 interface (Axon Instruments). Voltage pulses were generated and data collected using pClamp™ (Axon Instruments). Patch pipettes were fashioned from Corning™ 8161 borosilicate glass (Dow Corning), have resistances of 0.5-2 MΩ), and are sylgard coated to reduce capacitance transients. Whole-cell recordings are leak corrected using P/4 subtraction. Typical extracellular solution contains (in mM): 140 NaCl, 2 KCl, 1.5 $CaCl_2$, 1 $MgCl_2$ and 10 HEPES pH 7.4 with NaOH. Internal solution contains (in mM): 105 CsF, 35 NaCl, 5 EGTA and 10 HEPES pH 7.4 with CsOH. Cells expressing the target cDNA were identified using beads coated with an antibody against CD8 (Dynabeads, Dynal Corp.).

Development of Cameleon Assay.

Cameleon is a fluorescent biosynthetic $Ca^{2+}$ indicator constructed by inserting a $Ca^{2+}$ sensor (Calmodulin and M13, a calmodulin-binding protein) between two mutated forms of green fluorescent protein (GFP): the energy acceptor Venus, a derivative of yellow fluorescent protein (YFP), and the energy donor, cyan fluorescent protein (CFP) (Evanko D S and Haydon P G, *Cell calcium* 2005, 37: 341-348). Cameleon fluorescence is affected by differences in the concentration of $Ca^{2+}$ that alter the amount of fluorescence resonance energy transfer (FRET) between CFP and Venus. This process is influenced by $Ca^{2+}$-induced change in the conformation of calmoduline-M13, which, consequently, alters the relative angular displacement between the two mutant GFPs, bringing them closer together, for example, following an increase in $[Ca^{2+}]$. The increase in FRET is directly correlated to $[Ca^{2+}]$ increase. The fluorescence intensity was measured using a Packard Fusion™ Universal Microplate Analyzer. 75,000 cells per well were analyzed in a bath solution containing 140 mM NaCl, 2 mM KCl, 1.5 mM $CaCl_2$, 1 mM $MgCl_2$, 10 mM glucose, and 10 mM Na-HEPES. For calcium measurements, the bath solution contained: 140 mM NaCl, 2 mM KCl, 25 mM $CaCl_2$, 10 mM glucose and 10 mM Na-HEPES. The pH of the bath solutions was adjusted to pH 7.4 using 1N NaOH.

Example 2

Effect of the Mutations on Calcium Permeability

Figure 2:
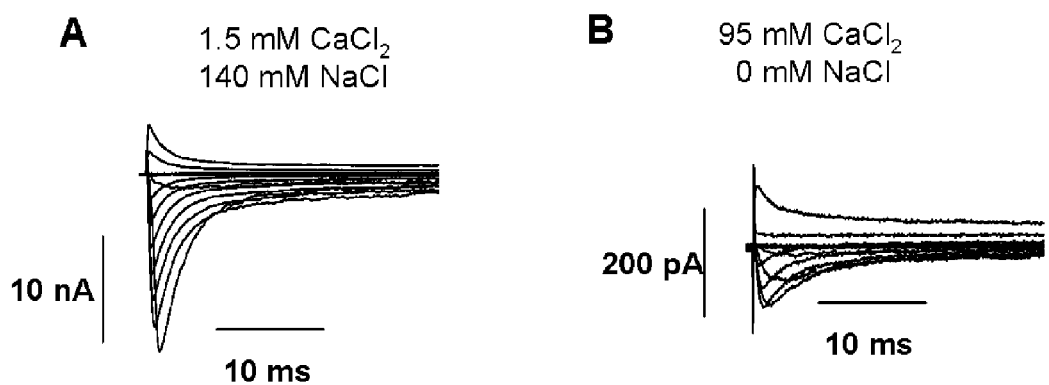
FIG. 2 shows representative trace currents of HEK293 cells transiently transfected with $Na_v1.5^{Mut}$ sodium channel. The currents were recorded in presence of 140 mM NaCl and 1.5 mM $CaCl_2$ in the extracellular solution (FIG. 2A), or with 95 mM $CaCl_2$ and 0 mM NaCl in the extracellular solution (FIG. 2B). Cells were held at −120 mV and depolarized from −80 to +40 mV in 10 mV increments.

The results presented at FIG. 2 clearly show that the mutated $Na_v1.5$ sodium channel is still permeable to $Na^+$ ions (FIG. 2A), but is also permeable to $Ca^{2+}$ ions (FIG. 2B), which is the effect of the mutation in the "DEKA" motif. FIG. 2 also shows that there is a persistent current in both situations (FIG. 2A and B), which is likely due to a decreased/slower channel deactivation caused by the mutation in the "IFM" motif.

Example 3

HEK293 Cells Stably Expressing the Cameleon Biosensor

Figure 3A:
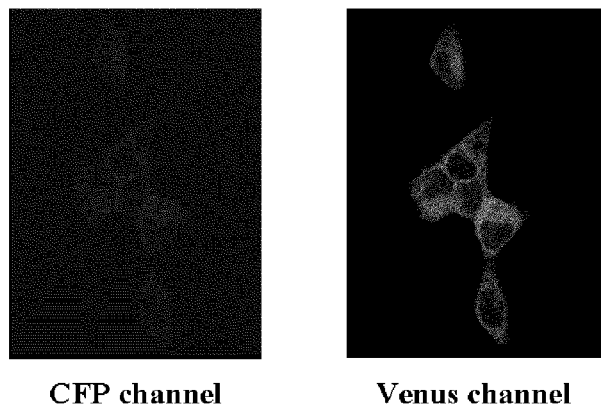
FIG. 3A: Individual Venus (right panel) and CFP (left panel) fluorescence image taken with a 40× objective.
Figure 3B:
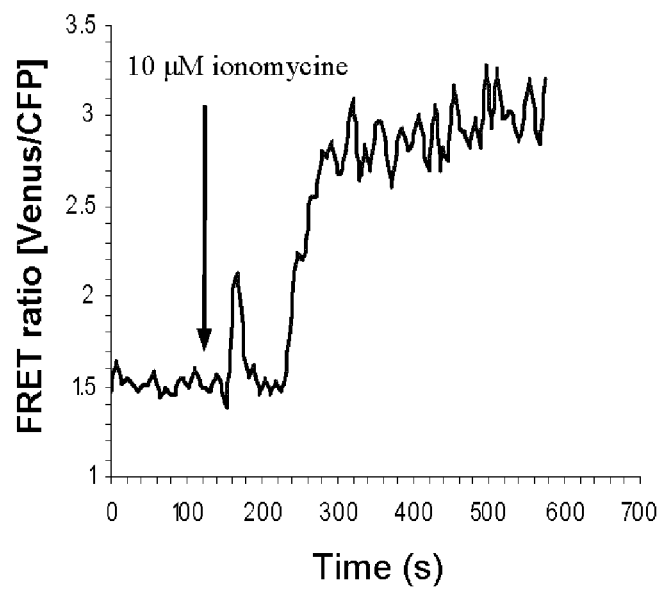
FIG. 3B: Plot of FRET ratio (Venus/CFP) versus time following addition of 10 μM ionomycin.

A HEK293 cell line stably expressing the Cameleon biosensor alone was treated with ionomycin (10 µM), a calcium ionophore, to raise the intracellular level of $Ca^{2+}$, and the FRET ratio was analysed by confocal microscopy. As shown in FIG. 3B, the Cameleon biosensor can be stably expressed in HEK293 cell and permits to detect intracellular $Ca^{2+}$ fluctuations, as indicated by the increase in the Venus/CFP ratio (i.e. increase in FRET) following addition of ionomycin.

Example 4

HEK293 Cells Stably Expressing the Mutated $Na_v1.5$ Polypeptide and the Cameleon Biosensor ($VC/Na_v1.5$)

Figure 4A:
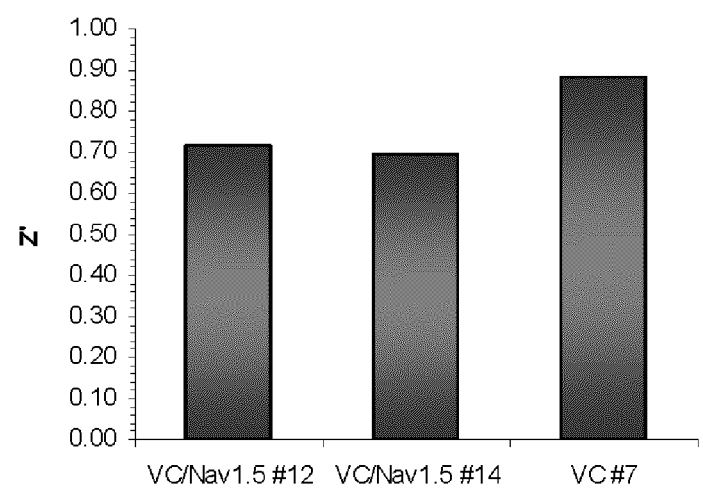
FIG. 4A shows a Z' evaluation of two $Na_v1.5^{Mut}$/Cameleon cell lines, VC/$Na_v1.5$ #12 (Z'=0.72) and #14 (Z'=0.69), and a control Cameleon cell line, VC #7 (Z'32 0.88).
Figure 4B:
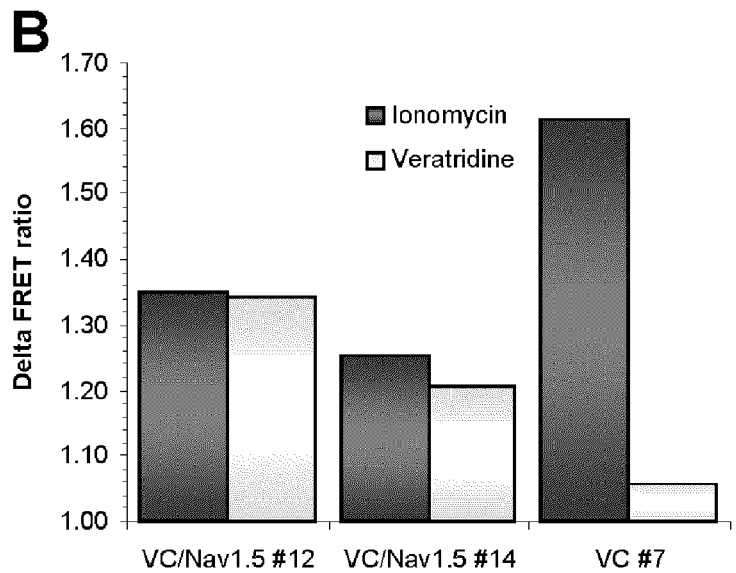
FIG. 4B shows a treatment of the $Na_v1.5^{Mut}$/Cameleon and Cameleon cell lines with ionomycin (grey bars) or veratridine (white bars)

The Z'-factor (a measure of the quality or power of a high-throughput screening (HTS) assay) was analyzed in a fluorescence-microplate-based assay. Z'-factor values of 0.72 and 0.69 were obtained for the $VC/Na_v1.5$ #12 and #14 cell lines, respectively (FIG. 4A). For a HTS assay, a Z'-factor between 0.5 and 1 is considered "excellent" (Zhang JH et al., *J Biomol Screen* 1999, 4(2): 67-73). The effect of veratridine, a sodium channel agonist, was also assessed and the results showed that VC/Na$_v$1.5 #12 and #14 cell lines respond to veratridine as well as ionomycin treatment, whereas VC #7, the cell line that does not express a sodium channel, respond only to ionomycin (FIG. 4B). These results indicate that the Na$_v$1.5$^{Mut}$/Cameleon cells express a functional sodium channel that is permeable to calcium ions, and that the Cameleon biosensor is able to detect the modulation of Ca$^{2+}$ caused by activation of the Na$_v$1.5$^{Mut}$ channel.

Figure 5:
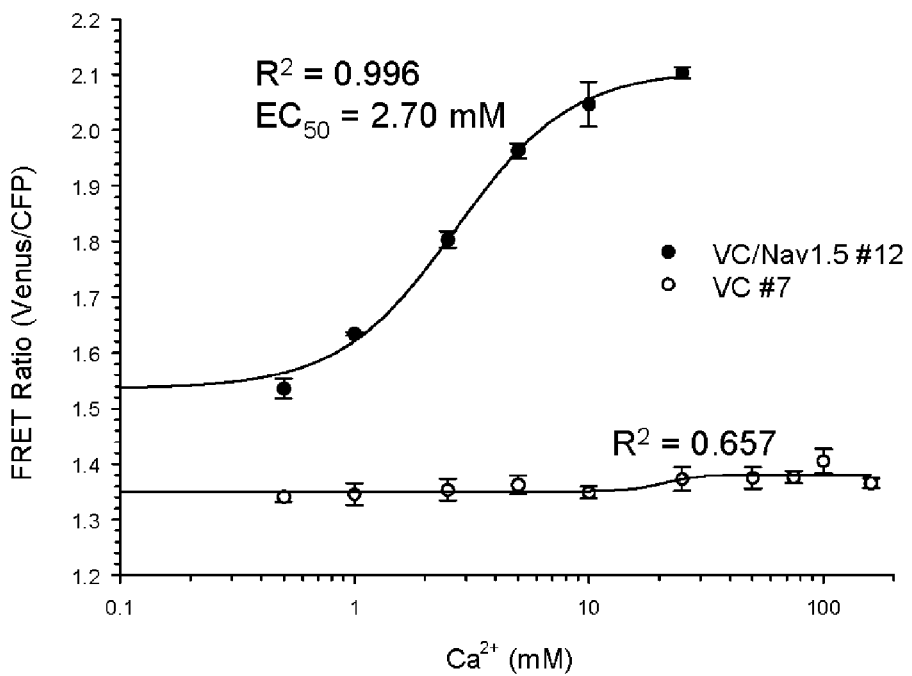
FIG. 5 shows dose-response measurements of FRET signals in response to calcium. VC/$Na_v1.5$ #12 (filled dots) and control VC #7 (empty dots) cell lines were exposed to different extracellular calcium concentrations ([$Ca^{2+}$]). The Cameleon was able to detect different [$Ca^{2+}$] and VC/$Na_v1.5$ #12 showed a strong dose-response relationship ($R^2=0.996$). These results were obtained in fluorescence microplate assay with an excitation at 425 nm and emission at 480 nm (CFP) and 525 nm (Venus). The FRET ratio represents the ratio of the signal detected at 525 nm (Venus) over that detected at 480 nm (CFP). Error bars represent the standard deviation of experiments performed in triplicate.

FIG. 5 shows that Na$_v$1.5$^{Mut}$/Cameleon cell lines respond to different concentrations of extracellular calcium. The intensity of the FRET ratio signals detected correlates with calcium concentrations, as shown by the correlation coefficient of 0.996 in the Na$_v$1.5$^{Mut}$/Cameleon cell line, indicative of a strong standard dose-response relationship. Such a strong dose-response relationship was not observed with the control Cameleon cell line ($R^2$=0.657).

Dose-response experiments in the presence of known sodium channel blockers (quinidine, sertralin and paroxetine) were performed. As shown in FIG. 6, addition of increasing doses of quinidine (FIG. 6A), sertralin (FIG. 6B) or paroxetine (FIG. 6C) results in a decrease in the Delta FRET ratio signal as compared to control cells (cells receiving buffer only), with a Z' value greater than 0.65 over the 96-well plate. These results demonstrate that drug-induced inhibition of sodium channels may be detected using a cell expressing a mutated Ca$^{2+}$ permeable sodium channel and a Cameleon biosensor.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A mutated voltage gated sodium channel ($Na_v$) alpha subunit polypeptide comprising the amino acid sequence of SEQ ID NO: 5.

2. An isolated nucleic acid encoding the mutated $Na_v$ alpha subunit polypeptide of claim 1.

3. A vector comprising the nucleic acid of claim 2.

4. A cell comprising the nucleic acid of claim 2.

5. A method for determining whether a test compound modulates the activity of a voltage gated sodium channel ($Na_v$), said method comprising
   (a) providing a cell expressing the mutated $Na_v$ alpha subunit polypeptide of claim 1; and
   (b) determining the intracellular level of a group IIA divalent cation in said cell in the presence or absence of said test compound,
wherein a difference in the intracellular level of said group IIA divalent cation in the presence relative to the absence of said test compound is indicative that said test compound modulates the activity of a voltage gated sodium channel.

6. The method of claim 5, wherein said group IIA divalent cation is calcium ($Ca^{2+}$).

7. The method of claim 6, wherein the intracellular calcium level is determined by determining the conformational change of a calcium-binding polypeptide, wherein said calcium-binding polypeptide is calmodulin (CaM) or a calcium-binding fragment thereof.

8. The method of claim 5, wherein said cell further expresses a first and second chimeric polypeptide, wherein
   (i) said first chimeric polypeptide comprises:
      (a) a first domain comprising a first fluorescent agent having an emission spectra;
      (b) a second domain linked to said first domain and comprising a calcium-binding polypeptide;
   (ii) said second chimeric polypeptide comprises:
      (a) a first domain comprising a polypeptide which binds in a calcium-dependent manner to said calcium-binding polypeptide; and
      (b) a second domain linked to said first domain of said second chimeric polypeptide and comprising a second fluorescent agent having an absorption spectra which overlaps with the emission spectra of said first fluorescent agent;
wherein the intracellular calcium level is determined by measuring the intensity of the fluorescence emitted by said second fluorescent agent.

9. The method of claim 5, wherein said cell further expresses a first and second chimeric polypeptide, wherein
   (i) said first chimeric polypeptide comprises:
      (a) a first domain comprising a first fluorescent agent having an absorption spectra;
      (b) a second domain linked to said first domain and comprising a calcium-binding polypeptide;
   (ii) said second chimeric polypeptide comprises:
      (a) a first domain comprising a polypeptide which binds in a calcium-dependent manner to said calcium-binding polypeptide; and
      (b) a second domain linked to said first domain of said second chimeric polypeptide and comprising a second fluorescent agent having an emission spectra which overlaps with the absorption spectra of said first fluorescent agent;
wherein the intracellular calcium level is determined by measuring the intensity of the fluorescence emitted by said first fluorescent agent.

10. The method of claim 7, wherein said conformational change allows binding with a polypeptide which binds in a calcium-dependent manner to said calcium-binding polypeptide, wherein said polypeptide binding in a calcium-dependent manner to said calcium-binding polypeptide is myosin light chain kinase or a calmodulin-binding domain thereof.

11. The method of claim 8, wherein said first and second chimeric polypeptides are recombinantly expressed as a single chimeric polypeptide.

* * * * *

SEQUENCE LISTING

```
<160> NUMBER OF SEQ ID NOS: 14

<210> SEQ ID NO 1
<211> LENGTH: 6051
<212> TYPE: DNA
<213> ORGANISM: Homo sapiens

<400> SEQUENCE: 1
atggcaaact tcctattacc tcggggcacc agcagcttcc gcaggttcac acgggagtcc      60
ctggcagcca tcgagaagcg catggcagag aagcaagccc gcggctcaac caccttgcag     120
gagagccgag aggggctgcc cgaggaggag gctccccggc cccagctgga cctgcaggcc     180
tccaaaaagc tgccagatct ctatggcaat ccaccccaag agctcatcgg agagccctg      240 gaggacctgg accccttcta tagcacccaa aagactttca tcgtactgaa taaaggcaag     300
accatcttcc ggttcagtgc caccaacgcc ttgtatgtcc tcagtccctt ccaccccatc     360
cggagagcgg ctgtgaagat tctggttcac tcgctcttca acatgctcat catgtgcacc     420
atcctcacca actgcgtgtt catggcccag cacgaccctc cacccctggac caagtatgtc     480 gagtacacct tcaccgccat ttacaccttt gagtctctgg tcaagattct ggctcgaggc     540
ttctgcctgc acgcgttcac tttccttcgg gacccatgga actggctgga ctttagtgtg     600
attatcatgg catacacaac tgaatttgtg gacctgggca atgtctcagc cttacgcacc     660
ttccgagtcc tccgggccct gaaaactata tcagtcattt cagggctgaa gaccatcgtg     720
ggggccctga tccagtctgt gaagaagctg gctgatgtga tggtcctcac agtcttctgc     780
ctcagcgtct ttgccctcat cggcctgcag ctcttcatgg gcaacctaag gcacaagtgc     840
gtgcgcaact tcacagcgct caacggcacc aacggctccg tggaggccga cggcttggtc     900
tgggaatccc tggacctta cctcagtgat ccagaaaatt acctgctcaa gaacggcacc     960
tctgatgtgt tactgtgtgg gaacagctct gacgctggga catgtccgga gggctaccgg    1020
tgcctaaagg caggcgagaa ccccgaccac ggctacacca gcttcgattc ctttgcctgg    1080
gcctttcttg cactcttccg cctgatgacg caggactgct gggagcgcct ctatcagcag    1140
accctcaggt ccgcagggaa gatctacatg atcttcttca tgcttgtcat cttcctgggg    1200
tccttctacc tggtgaacct gatcctggcc gtggtcgcaa tggcctatga ggagcaaaac    1260
```

```
caagccacca tcgctgagac cgaggagaag gaaaagcgct tccaggaggc catggaaatg    1320
ctcaagaaag aacacgaggc cctcaccatc aggggtgtgg ataccgtgtc ccgtagctcc    1380
ttggagatgt ccccttTggc cccagtaaac agccatgaga aagaagcaa gaggagaaaa    1440 cggatgtctt caggaactga ggagtgtggg gaggacaggc tccccaagtc tgactcagaa    1500
gatggtccca gagcaatgaa tcatctcagc ctcacccgtg gcctcagcag gacttctatg    1560
aagccacgtt ccagccgcgg gagcattttc acctttcgca ggcgagacct gggttctgaa    1620
gcagattttg cagatgatga aaacagcaca gcggggagaa gcgagagcca ccacacatca    1680
ctgctggtgc cctggcccct cgcgcggacc agtgcccagg acagcccag tcccggaacc    1740 tcggctcctg ccacgcccct ccatggcaaa aagaacagca ctgtggactg caatggggtg    1800
gtctcattac tgggggcagg cgacccgag gccacatccc caggaagcca cctcctccgc    1860
cctgtgatgc tagagcaccc gccagacacg accacgccat cggaggagcc aggcgggccc    1920
cagatgctga cctcccaggc tccgtgtgta gatggcttcg aggagccagg agcacggcag    1980
cgggccctca gcgcagtcag cgtcctcacc agcgcactgg aagagttaga ggagtctcgc    2040
cacaagtgtc caccatgctg gaaccgtctc gcccagcgct acctgatctg ggagtgctgc    2100
ccgctgtgga tgtccatcaa gcagggagtg aagttggtgg tcatggaccc gtttactgac    2160
ctcaccatca ctatgtgcat cgtactcaac acactcttca tggcgctgga gcactacaac    2220
atgacaagtg aattcgagga gatgctgcag gtcggaaacc tggtcttcac agggattttc    2280
acagcagaga tgaccttcaa gatcattgcc ctcgacccct actactactt ccaacagggc    2340
tggaacatct tcgacagcat catcgtcatc cttagcctca tggagctggg cctgtcccgc    2400
atgagcaact tgtcggtgct gcgctccttc gcctgctgc gggtcttcaa gctggccaaa    2460
tcatggccca ccctgaacac actcatcaag atcatcggga actcagtggg ggcactgggg    2520
aacctgacac tggtgctagc catcatcgtg ttcatctttg ctgtggtggg catgcagctc    2580
tttggcaaga actactcgga gctgagggac agcgactcag gcctgctgcc tcgctggcac    2640
atgatggact ctttTcatgc cttcctcatc atcttccgca tcctctgtgg agagtggatc    2700
gagaccatgt gggactgcat ggaggtgtcg ggcagtcat tatgcctgct ggtcttcttg    2760
cttgttatgg tcattggcaa ccttgtggtc ctgaatctct tcctggcctt gctgctcagc    2820
tccttcagtg cagacaacct cacagcccct gatgaggaca gagagatgaa caacctccag    2880
ctggccctgg cccgcatcca gaggggcctg cgctttgtca gcggaccac ctgggatttc    2940 tgctgtggtc tcctgcggca gcggcctcag aagcccgcag cccttgccgc ccagggccag    3000
ctgcccagct gcattgccac cccctactcc ccgccacccc cagagacgga aaggtgcct    3060 cccacccgca aggaaacacg gtttgaggaa ggcgagcaac caggccaggg cacccccggg    3120
gatccagagc ccgtgtgtgt gcccatcgct gtggccgagt cagacacaga tgaccaagaa    3180
gaagatgagg agaacagcct gggcacggag gaggagtcca gcaagcagca ggaatcccag    3240
cctgtgtccg gtgcccaga ggcccctccg gattccagga cctggagcca ggtgtcagcg    3300
actgcctcct ctgaggccga ggccagtgca tctcaggccg actggcggca gcagtggaaa    3360
gcggaacccc aggcccagg gtgcggtgag accccagagg acagttgctc cgagggcagc    3420
acagcagaca tgaccaacac cgctgagctc tggagcagaa tccctgacct cggccaggat    3480
gtcaaggacc cagaggactg cttcactgaa ggctgtgtcc ggcgctgtcc ctgctgtgcg    3540
gtggacacca cacaggcccc agggaaggtc tggtggcggt tgcgcaagac ctgctaccac    3600
atcgtggagc acagctggtt cgagacattc atcatcttca tgatcctact cagcagtgga    3660
```

```
gcgctggcct tcgaggacat ctacctagag gagcggaaga ccatcaaggt tctgcttgag    3720
tatgccgaca agatgttcac atatgtcttc gtgctggaga tgctgctcaa gtgggtggcc    3780
tacggcttca agaagtactt caccaatgcc tggtgctggc tcgacttcct catcgtagac    3840
gtctctctgg tcagcctggt ggccaacacc ctgggctttg ccgagatggg ccccatcaag    3900
tcactgcgga cgctgcgtgc actccgtcct ctgagagctc tgtcacgatt tgagggcatg    3960
agggtggtgg tcaatgccct ggtgggcgcc atcccgtcca tcatgaacgt cctcctcgtc    4020
tgcctcatct tctggctcat cttcagcatc atgggcgtga acctctttgc ggggaagttt    4080
gggaggtgca tcaaccagac agagggagac ttgcctttga actacaccat cgtgaacaac    4140
aagagccagt gtgagtcctt gaacttgacc ggagaattgt actggaccaa ggtgaaagtc    4200
aactttgaca acgtggggc cgggtacctg gcccttctgc aggtggcaac attttgtggc    4260
tggatggaca ttatgtatgc agctgtggac tccaggggt atgaagagca gcctcagtgg    4320
gaatacaacc tctacatgta catctatttt gtcattttca tcatctttgg gtctttcttc    4380
accctgaacc tctttattgg tgtcatcatt gacaacttca accaacagaa gaaaagttta    4440
gggggccagg acatccaaat gacagaggag cagaagaagt actacaatgc catgaagaag    4500
ctgggctcca agaagcccca gaagcccatc ccacggcccc tgaacaagta ccagggcttc    4560
atattcgaca ttgtgaccaa gcaggccttt gacgtcacca tcatgtttct gatctgcttg    4620
aatatggtga ccatgatggt ggagacagat gaccaaagtc ctgagaaaat caacatcttg    4680
gccaagatca acctgctctt tgtggccatc ttcacaggcg agtgtattgt caagctggct    4740
gccctgcgcc actactactt caccaacagc tggaatatct tcgacttcgt ggttgtcatc    4800
ctctccatcg tgggcactgt gctctcggac atcatccaga agtacttctt ctcccccgacg    4860
ctcttccgag tcatccgcct ggcccgaata ggccgcatcc tcagactgat ccgaggggcc    4920
aaggggatcc gcacgctgct cttttgccctc atgatgtccc tgcctgccct cttcaacatc    4980
gggctgctgc tcttcctcgt catgttcatc tactccatct ttggcatggc caacttcgct    5040
tatgtcaagt gggaggctgg catcgacgac atgttcaact ccagaccctt cgccaacagc    5100
atgctgtgcc tcttccagat caccacgtcg gccggctggg atggcctcct cagccccatc    5160
ctcaacactg gccgcccta ctgcgacccc actctgccca acagcaatgg ctctcggggg    5220
gactgcggga gccagccgt gggcatcctc ttcttcacca cctacatcat catctccttc    5280
ctcatcgtgg tcaacatgta cattgccatc atcctggaga acttcagcgt ggccacggag    5340
gagagcaccg agccctgag tgaggacgac ttcgatatgt tctatgagat ctgggagaaa    5400
tttgacccag aggccactca gtttattgag tattcggtcc tgtctgactt tgccgatgcc    5460
ctgtctgagc cactccgtat cgccaagccc aaccagataa gcctcatcaa catggacctg    5520
cccatggtga gtgggaccg catccattgc atggacattc tctttgcctt caccaaaagg    5580
gtcctggggg agtctgggga gatggacgcc ctgaagatcc agatggagga gaagttcatg    5640
gcagccaacc catccaagat ctcctacgag cccatcacca ccacactccg gcgcaagcac    5700
gaagaggtgt cggccatggt tatccagaga gccttccgca ggcacctgct gcaacgctct    5760
ttgaagcatg cctccttcct cttccgtcag caggcgggca gcggcctctc cgaagaggat    5820
gcccctgagc gagagggcct catcgcctac gtgatgagtg agaacttctc ccgaccctt    5880
ggcccaccct ccagctcctc catctcctcc acttccttcc caccctccta tgacagtgtc    5940
actagagcca ccagcgataa cctccaggtg cggggggtctg actacagcca cagtgaagat    6000
ctcgccgact tccccccttc tccggacagg gaccgtgagt ccatcgtgtg a              6051
```

<210> SEQ ID NO 2
<211> LENGTH: 6051
<212> TYPE: DNA
<213> ORGANISM: Homo sapiens

<400> SEQUENCE: 2

| | | | | | | |
|---|---|---|---|---|---|---|
| atggcaaact | tcctattacc | tcggggcacc | agcagcttcc | gcaggttcac | acgggagtcc | 60 |
| ctggcagcca | tcgagaagcg | catggcagag | aagcaagccc | gcggctcaac | caccttgcag | 120 |
| gagagccgag | aggggctgcc | cgaggaggag | gctccccggc | cccagctgga | cctgcaggcc | 180 |
| tccaaaaagc | tgccagatct | ctatggcaat | ccaccccaag | agctcatcgg | agagccctg | 240 |
| gaggacctgg | accccttcta | tagcacccaa | aagactttca | tcgtactgaa | taaaggcaag | 300 |
| accatcttcc | ggttcagtgc | caccaacgcc | ttgtatgtcc | tcagtccctt | ccacccatc | 360 |
| cggagagcgg | ctgtgaagat | tctggttcac | tcgctcttca | acatgctcat | catgtgcacc | 420 |
| atcctcacca | actgcgtgtt | catggcccag | cacgaccctc | caccctggac | caagtatgtc | 480 |
| gagtacacct | tcaccgccat | ttacacctt | gagtctctgg | tcaagattct | ggctcgaggc | 540 |
| ttctgcctgc | acgcgttcac | tttccttcgg | gacccatgga | actggctgga | ctttagtgtg | 600 |
| attatcatgg | catacacaac | tgaatttgtg | gacctgggca | atgtctcagc | cttacgcacc | 660 |
| ttccgagtcc | tccgggccct | gaaaactata | tcagtcattt | cagggctgaa | gaccatcgtg | 720 |
| ggggccctga | tccagtctgt | gaagaagctg | gctgatgtga | tggtcctcac | agtcttctgc | 780 |
| ctcagcgtct | ttgccctcat | cggcctgcag | ctcttcatgg | caacctaag | gcacaagtgc | 840 |
| gtgcgcaact | tcacagcgct | caacggcacc | aacggctccg | tggaggccga | cggcttggtc | 900 |
| tgggaatccc | tggaccttta | cctcagtgat | ccagaaaatt | acctgctcaa | gaacggcacc | 960 |
| tctgatgtgt | tactgtgtgg | gaacagctct | gacgctggga | catgtccgga | gggctaccgg | 1020 |
| tgcctaaagg | caggcgagaa | ccccgaccac | ggctacacca | gcttcgattc | ctttgcctgg | 1080 |
| gcctttcttg | cactcttccg | cctgatgacg | caggactgct | gggagcgcct | ctatcagcag | 1140 |
| accctcaggt | ccgcagggaa | gatctacatg | atcttcttca | tgcttgtcat | cttcctgggg | 1200 |
| tccttctacc | tggtgaacct | gatcctggcc | gtggtcgcaa | tggcctatga | ggagcaaaac | 1260 |
| caagccacca | tcgctgagac | cgaggagaag | gaaaagcgct | tccaggaggc | catggaaatg | 1320 |
| ctcaagaaag | aacacgaggc | cctccaccat | aggggtgtgg | ataccgtgtc | ccgtagctcc | 1380 |
| ttggagatgt | ccccttttggc | cccagtaaac | agccatgaga | agaagcaa | gaggagaaaa | 1440 |
| cggatgtctt | caggaactga | ggagtgtggg | gaggacaggc | tccccaagtc | tgactcagaa | 1500 |
| gatggtccca | gagcaatgaa | tcatctcagc | ctcacccgtg | gcctcagcag | gacttctatg | 1560 |
| aagccacgtt | ccagccgcgg | gagcattttc | acctttcgca | ggcgagacct | gggttctgaa | 1620 |
| gcagattttg | cagatgatga | aaacagcaca | gcgggggaga | gcgagagcca | ccacacatca | 1680 |
| ctgctggtgc | cctggcccct | cgccggacc | agtgcccagg | acagcccag | tcccggaacc | 1740 |
| tcggctcctg | gccacgccct | ccatggcaaa | agaacagca | ctgtggactg | caatggggtg | 1800 |
| gtctcattac | tggggggcagg | cgacccgag | gccacatccc | caggaagcca | cctcctccgc | 1860 |
| cctgtgatgc | tagagcaccc | gccagacacg | accacgccat | cggaggagcc | aggcgggccc | 1920 |
| cagatgctga | cctcccaggc | tccgtgtgta | gatggcttcg | aggagccagg | agcacggcag | 1980 |
| cgggccctca | gcgcagtcag | cgtcctcacc | agcgcactgg | aagagttaga | ggagtctcgc | 2040 |
| cacaagtgtc | caccatgctg | gaaccgtctc | gcccagcgct | acctgatctg | ggagtgctgc | 2100 |
| ccgctgtgga | tgtccatcaa | gcaggggagtg | aagttggtgg | tcatggaccc | gtttactgac | 2160 |

```
ctcaccatca ctatgtgcat cgtactcaac acactcttca tggcgctgga gcactacaac    2220
atgacaagtg aattcgagga gatgctgcag gtcggaaacc tggtcttcac agggatttttc   2280 acagcagaga tgaccttcaa gatcattgcc ctcgacccct actactactt ccaacagggc    2340
tggaacatct tcgacagcat catcgtcatc cttagcctca tggagctggg cctgtcccgc    2400
atgagcaact tgtcggtgct gcgctccttc cgcctgctgc gggtcttcaa gctggccaaa    2460
tcatggccca ccctgaacac actcatcaag atcatcggga actcagtggg ggcactgggg   2520
aacctgacac tggtgctagc catcatcgtg ttcatctttg ctgtggtggg catgcagctc    2580
tttggcaaga actactcgga gctgagggac agcgactcag gcctgctgcc tcgctggcac    2640
atgatggact tctttcatgc cttcctcatc atcttccgca tcctctgtgg agagtggatc    2700
gagaccatgt gggactgcat ggaggtgtcg gggcagtcat tatgcctgct ggtcttcttg    2760
cttgttatgg tcattggcaa ccttgtggtc ctgaatctct tcctggcctt gctgctcagc    2820
tccttcagtg cagacaacct cacagcccct gatgaggaca gagagatgaa caacctccag    2880
ctggccctgg cccgcatcca gagggggcctg cgctttgtca gcggaccac ctgggatttc    2940 tgctgtggtc tcctgcggca gcggcctcag aagcccgcag cccttgccgc ccagggccag    3000
ctgcccagct gcattgccac ccctactcc ccgccacccc cagagacgga aaggtgcct    3060 cccacccgca aggaaacacg gtttgaggaa ggcgagcaac caggccaggg cacccccggg   3120
gatccagagc ccgtgtgtgt gcccatcgct gtggccgagt cagacacaga tgaccaagaa    3180
gaagatgagg agaacagcct gggcacggag gaggagtcca gcaagcagca ggaatcccag    3240
cctgtgtccg gtggcccaga ggcccctccg gattccagga cctggagcca ggtgtcagcg    3300
actgcctcct ctgaggccga ggccagtgca tctcaggccg actggcggca gcagtggaaa    3360
gcggaacccc aggcccagg gtgcggtgag accccagagg acagttgctc cgagggcagc    3420
acagcagaca tgaccaacac cgctgagctc ctggagcaga tccctgacct cggccaggat    3480
gtcaaggacc cagaggactg cttcactgaa ggctgtgtcc ggcgctgtcc ctgctgtgcg    3540
gtggacacca cacaggcccc agggaaggtc tggtggcggt tgcgcaagac ctgctaccac    3600
atcgtggagc acagctggtt cgagacattc atcatcttca tgatcctact cagcagtgga    3660
gcgctggcct tcgaggacat ctacctagag gagcggaaga ccatcaaggt tctgcttgag    3720
tatgccgaca agatgttcac atatgtcttc gtgctggaga tgctgctcaa gtgggtggcc    3780
tacggcttca gaagtactt caccaatgcc tggtgctggc tcgacttcct catcgtagac    3840
gtctctctgg tcagcctggt ggccaacacc ctgggctttg ccgagatggg ccccatcaag    3900
tcactgcgga cgctgcgtgc actccgtcct ctgagagctc tgtcacgatt tgagggcatg    3960
agggtggtgg tcaatgccct ggtgggcgcc atcccgtcca tcatgaacgt cctcctcgtc    4020
tgcctcatct tctggctcat cttcagcatc atgggcgtga acctctttgc ggggaagttt    4080
gggaggtgca tcaaccagac agagggggagac ttgcctttga actacaccat cgtgaacaac    4140
aagagccagt gtgagtcctt gaacttgacc ggagaattgt actggaccaa ggtgaaagtc    4200
aactttgaca acgtggggc cgggtacctg gcccttctgc aggtggcaac atttttgtggc    4260 tggatggaca ttatgtatgc agctgtggac tccaggggggt atgaagagca gcctcagtgg    4320
gaatacaacc tctacatgta catctatttt gtcattttca tcatctttgg gtctttcttc    4380
accctgaacc tctttattgg tgtcatcatt gacaacttca ccaacagaa gaaaagtta    4440 gggggccagg acatccagat gacagaggag cagaagaagt actacaatgc catgaagaag    4500
ctgggctcca agaagccca gaagcccatc ccacggcccc tgaacaagta ccagggcttc    4560
```

| | |
|---|---|
| atattcgaca ttgtgaccaa gcaggccttt gacgtcacca tcatgtttct gatctgcttg | 4620 |
| aatatggtga ccatgatggt ggagacagat gaccaaagtc ctgagaaaat caacatcttg | 4680 |
| gccaagatca acctgctctt tgtggccatc ttcacaggcg agtgtattgt caagctggct | 4740 |
| gccctgcgcc actactactt caccaacagc tggaatatct tcgacttcgt ggttgtcatc | 4800 |
| ctctccatcg tgggcactgt gctctcggac atcatccaga agtacttctt ctccccgacg | 4860 |
| ctcttccgag tcatccgcct ggcccgaata ggccgcatcc tcagactgat ccgaggggcc | 4920 |
| aaggggatcc gcacgctgct ctttgccctc atgatgtccc tgcctgccct cttcaacatc | 4980 |
| gggctgctgc tcttcctcgt catgttcatc tactccatct ttggcatggc caacttcgct | 5040 |
| tatgtcaagt gggaggctgg catcgacgac atgttcaact tccagacctt cgccaacagc | 5100 |
| atgctgtgcc tcttccagat caccacgtcg gccggctggg atggcctcct cagccccatc | 5160 |
| ctcaacactg ggccgcccta ctgcgacccc actctgccca acagcaatgg ctctcggggg | 5220 |
| gactgcggga gcccagccgt gggcatcctc ttcttcacca cctacatcat catctccttc | 5280 |
| ctcatcgtgg tcaacatgta cattgccatc atcctggaga acttcagcgt ggccacggag | 5340 |
| gagagcaccg agcccctgag tgaggacgac ttcgatatgt tcgatgagat ctgggagaaa | 5400 |
| tttgacccag aggccactca gtttattgag tattcggtcc tgtctgactt tgccgatgcc | 5460 |
| ctgtctgagc cactccgtat cgccaagccc aaccagataa gcctcatcaa catggacctg | 5520 |
| cccatggtga gtggggaccg catccattgc atggacattc tctttgcctt caccaaaagg | 5580 |
| gtcctggggg agtctgggga gatggacgcc ctgaagatcc agatggagga gaagttcatg | 5640 |
| gcagccaacc catccaagat ctcctacgag cccatcacca ccacactccg gcgcaagcac | 5700 |
| gaagaggtgt cggccatggt tatccagaga gccttccgca ggcacctgct gcaacgctct | 5760 |
| ttgaagcatg cctccttcct cttccgtcag caggcgggca gcggcctctc cgaagaggat | 5820 |
| gcccctgagc gagagggcct catcgcctac gtgatgagtg agaacttctc ccgacccctt | 5880 |
| ggcccaccct ccagctcctc catctcctcc acttccttcc caccctccta tgacagtgtc | 5940 |
| actagagcca ccagcgataa cctccaggtg cgggggtctg actacagcca cagtgaagat | 6000 |
| ctcgccgact tccccccttc tccggacagg gaccgtgagt ccatcgtgtg a | 6051 |

```
<210> SEQ ID NO 3
<211> LENGTH: 6051
<212> TYPE: DNA
<213> ORGANISM: Homo sapiens

<400> SEQUENCE: 3
```

| | |
|---|---|
| atggcaaact tcctattacc tcggggcacc agcagcttcc gcaggttcac acgggagtcc | 60 |
| ctggcagcca tcgagaagcg catggcagag aagcaagccc gcggctcaac caccttgcag | 120 |
| gagagccgag aggggctgcc cgaggaggag gctccccggc cccagctgga cctgcaggcc | 180 |
| tccaaaaagc tgccagatct ctatggcaat ccaccccaag agctcatcgg agagcccctg | 240 |
| gaggacctgg acccctctcta tagcacccaa aagactttca tcgtactgaa taaaggcaag | 300 |
| accatcttcc ggttcagtgc caccaacgcc ttgtatgtcc tcagtccctt ccaccccatc | 360 |
| cggagagcgg ctgtgaagat tctggttcac tcgctcttca acatgctcat catgtgcacc | 420 |
| atcctcacca actgcgtgtt catggcccag cacgaccctc caccctggac caagtatgtc | 480 |
| gagtacacct tcaccgccat ttacacccttt gagtctctgg tcaagattct ggctcgaggc | 540 |
| ttctgcctgc acgcgttcac tttccttcgg gacccatgga actggctgga ctttagtgtg | 600 |
| attatcatgg catacacaac tgaatttgtg gacctgggca atgtctcagc cttacgcacc | 660 |

```
ttccgagtcc tccgggccct gaaaactata tcagtcattt cagggctgaa gaccatcgtg    720
ggggccctga tccagtctgt gaagaagctg gctgatgtga tggtcctcac agtcttctgc    780
ctcagcgtct ttgccctcat cggcctgcag ctcttcatgg caacctaag gcacaagtgc    840
gtgcgcaact tcacagcgct caacggcacc aacggctccg tggaggccga cggcttggtc    900
tgggaatccc tggacctta cctcagtgat ccagaaaatt acctgctcaa gaacggcacc    960
tctgatgtgt tactgtgtgg aacagctct gacgctggga catgtccgga gggctaccgg   1020
tgcctaaagg caggcgagaa ccccgaccac ggctacacca gcttcgattc ctttgcctgg   1080
gcctttcttg cactcttccg cctgatgacg caggactgct gggagcgcct ctatcagcag   1140
accctcaggt ccgcagggaa gatctacatg atcttcttca tgcttgtcat cttcctgggg   1200
tccttctacc tggtgaacct gatcctggcc gtggtcgcaa tggcctatga ggagcaaaac   1260
caagccacca tcgctgagac cgaggagaag gaaaagcgct tccaggaggc catggaaatg   1320
ctcaagaaag aacacgaggc cctcaccatc agggtgtgg ataccgtgtc ccgtagctcc   1380
ttggagatgt cccctttggc cccagtaaac agccatgaga gaagaagcaa gaggagaaaa   1440
cggatgtctt caggaactga ggagtgtggg gaggacaggc tccccaagtc tgactcagaa   1500
gatggtccca gagcaatgaa tcatctcagc ctcacccgtg gcctcagcag gacttctatg   1560
aagccacgtt ccagccgcgg gagcattttc acctttcgca ggcgagacct gggttctgaa   1620
gcagattttg cagatgatga aaacagcaca gcggggaga gcgagagcca ccacacatca   1680
ctgctggtgc cctggcccct cgccggacc agtgcccagg gacagcccag tcccggaacc   1740
tcggctcctg gccacgccct ccatggcaaa aagaacagca ctgtggactg caatggggtg   1800
gtctcattac tgggggcagg cgacccgag gccacatccc caggaagcca cctcctccgc   1860
cctgtgatgc tagagcaccc gccagacacg accacgccat cggaggagcc aggcgggccc   1920
cagatgctga cctcccaggc tccgtgtgta gatggcttcg aggagccagg agcacggcag   1980
cgggccctca gcgcagtcag cgtcctcacc agcgcactgg aagagttaga ggagtctcgc   2040
cacaagtgtc caccatgctg gaaccgtctc gcccagcgct acctgatctg ggagtgctgc   2100
ccgctgtgga tgtccatcaa gcagggagtg aagttggtgg tcatggaccc gtttactgac   2160
ctcaccatca ctatgtgcat cgtactcaac acactcttca tggcgctgga gcactacaac   2220
atgacaagtg aattcgagga gatgctgcag gtcggaaacc tggtcttcac agggattttc   2280
acagcagaga tgaccttcaa gatcattgcc ctcgaccct actactactt ccaacagggc   2340
tggaacatct tcgacagcat catcgtcatc cttagcctca tggagctggg cctgtcccgc   2400
atgagcaact tgtcggtgct gcgctccttc cgcctgctgc gggtcttcaa gctggccaaa   2460
tcatggcccca cctgaacac actcatcaag atcatcggga actcagtggg ggcactgggg   2520
aacctgacac tggtgctagc catcatcgtg ttcatctttg ctgtggtggg catgcagctc   2580
tttggcaaga actactcgga gctgagggac agcgactcag gcctgctgcc tcgctggcac   2640
atgatggact ctttcatgc cttcctcatc atcttccgca tcctctgtgg agagtggatc   2700
gagaccatgt gggactgcat ggaggtgtcg ggcagtcat tatgcctgct ggtcttcttg   2760
cttgttatgg tcattggcaa ccttgtggtc ctgaatctct tcctggcctt gctgctcagc   2820
tccttcagtg cagacaacct cacagcccct gatgaggaca gagagatgaa caacctccag   2880
ctggccctgg cccgcatcca gggggcctg cgctttgtca gcggaccac ctgggatttc   2940
tgctgtggtc tcctgcggca gcggcctcag aagcccgcag cccttgccgc ccagggccag   3000
ctgcccagct gcattgccac ccctactcc ccgccacccc cagagacgga gaaggtgcct   3060
```

```
cccacccgca aggaaacacg gtttgaggaa ggcgagcaac caggccaggg caccccgggg   3120
gatccagagc ccgtgtgtgt gcccatcgct gtggccgagt cagacacaga tgaccaagaa   3180
gaagatgagg agaacagcct gggcacggag gaggagtcca gcaagcagca ggaatcccag   3240
cctgtgtccg gtggcccaga ggcccctccg gattccagga cctggagcca ggtgtcagcg   3300
actgcctcct ctgaggccga ggccagtgca tctcaggccg actggcggca gcagtggaaa   3360
gcggaacccc aggccccagg gtgcggtgag accccagagg acagttgctc cgagggcagc   3420
acagcagaca tgaccaacac cgctgagctc ctggagcaga tccctgacct cggccaggat   3480
gtcaaggacc cagaggactg cttcactgaa ggctgtgtcc ggcgctgtcc ctgctgtgcg   3540
gtggacacca cacaggcccc agggaaggtc tggtggcggt tgcgcaagac ctgctaccac   3600
atcgtggagc acagctggtt cgagacattc atcatcttca tgatcctact cagcagtgga   3660
gcgctggcct tcgaggacat ctacctagag gagcggaaga ccatcaaggt tctgcttgag   3720
tatgccgaca agatgttcac atatgtcttc gtgctggaga tgctgctcaa gtgggtggcc   3780
tacggcttca agaagtactt caccaatgcc tggtgctggc tcgacttcct catcgtagac   3840
gtctctctgg tcagcctggt ggccaacacc ctgggctttg ccgagatggg ccccatcaag   3900
tcactgcgga cgctgcgtgc actccgtcct ctgagagctc tgtcacgatt tgagggcatg   3960
agggtggtgg tcaatgccct ggtgggcgcc atcccgtcca tcatgaacgt cctcctcgtc   4020
tgcctcatct tctggctcat cttcagcatc atgggcgtga acctctttgc ggggaagttt   4080
gggaggtgca tcaaccagac agaggggagac ttgcctttga actacaccat cgtgaacaac   4140
aagagccagt gtgagtcctt gaacttgacc ggagaattgt actggaccaa ggtgaaagtc   4200
aactttgaca acgtggggc cgggtacctg gcccttctgc aggtggcaac attttgcggc   4260
tggatggaca ttatgtatgc agctgtggac tccaggggg atgaagagca gcctcagtgg   4320
gaatacaacc tctacatgta catctatttt gtcattttca tcatctttgg gtctttcttc   4380
accctgaacc tctttattgg tgtcatcatt gacaacttca accaacagaa gaaaaagtta   4440
gggggccagg acatccaaat gacagaggag cagaagaagt actacaatgc catgaagaag   4500
ctgggctcca agaagcccca gaagcccatc ccacggcccc tgaacaagta ccagggcttc   4560
atattcgaca ttgtgaccaa gcaggccttt gacgtcacca tcatgtttct gatctgcttg   4620
aatatggtga ccatgatggt ggagacagat gaccaaagtc ctgagaaaat caacatcttg   4680
gccaagatca acctgctctt tgtggccatc ttcacaggcg agtgtattgt caagctggct   4740
gccctgcgcc actactactt caccaacagc tggaatatct tcgacttcgt ggttgtcatc   4800
ctctccatcg tgggcactgt gctctcggac atcatccaga agtacttctt ctccccgacg   4860
ctcttccgag tcatccgcct ggcccgaata ggccgcatcc tcagactgat ccgaggggcc   4920
aaggggatcc gcacgctgct ctttgccctc atgatgtccc tgcctgccct cttcaacatc   4980
gggctgctgc tcttcctcgt catgttcatc tactccatct ttggcatggc caacttcgct   5040
tatgtcaagt gggaggctgg catcgacgac atgttcaact tccagacctt cgccaacagc   5100
atgctgtgcc tcttccagat caccacgtcg gccggctggg atggcctcct cagccccatc   5160
ctcaacactg ggccgcccta ctgcgacccc actctgccca acagcaatgg ctctcggggg   5220
gactgcggga gcccagccgt gggcatcctc ttcttcacca cctacatcat catctccttc   5280
ctcatcgtgg tcaacatgta cattgccatc atcctggaga acttcagcgt ggccacggag   5340
gagagcaccg agccctgag tgaggacgac ttcgatatgt tctatgagat ctgggagaaa   5400
tttgacccag aggccactca gtttattgag tattcggtcc tgtctgactt tgccgatgcc   5460
```

-continued

| | |
|---|---|
| ctgtctgagc cactccgtat cgccaagccc aaccagataa gcctcatcaa catggacctg | 5520 |
| cccatggtga gtggggaccg catccattgc atggacattc tctttgcctt caccaaaagg | 5580 |
| gtcctggggg agtctgggga gatggacgcc ctgaagatcc agatggagga aagttcatg | 5640 |
| gcagccaacc catccaagat ctcctacgag cccatcacca ccacactccg gcgcaagcac | 5700 |
| gaagaggtgt cggccatggt tatccagaga gccttccgca ggcacctgct gcaacgctct | 5760 |
| ttgaagcatg cctccttcct cttccgtcag caggcgggca gcggcctctc cgaagaggat | 5820 |
| gcccctgagc gagagggcct catcgcctac gtgatgagtg agaacttctc ccgacccctt | 5880 |
| ggcccaccct ccagctcctc catctcctcc acttccttcc caccctccta tgacagtgtc | 5940 |
| actagagcca ccagcgataa cctccaggtg cgggggtctg actacagcca cagtgaagat | 6000 |
| ctcgccgact ccccccttc tccggacagg gaccgtgagt ccatcgtgtg a | 6051 |

<210> SEQ ID NO 4
<211> LENGTH: 6051
<212> TYPE: DNA
<213> ORGANISM: Homo sapiens

<400> SEQUENCE: 4

| | |
|---|---|
| atggcaaact tcctattacc tcggggcacc agcagcttcc gcaggttcac acgggagtcc | 60 |
| ctggcagcca tcgagaagcg catggcagag aagcaagccc gcggctcaac caccttgcag | 120 |
| gagagccgag aggggctgcc cgaggaggag gctccccggc cccagctgga cctgcaggcc | 180 |
| tccaaaaagc tgccagatct ctatggcaat ccacccccaag agctcatcgg agagcccctg | 240 |
| gaggacctgg accccttcta tagcacccaa aagactttca tcgtactgaa taaaggcaag | 300 |
| accatcttcc ggttcagtgc caccaacgcc ttgtatgtcc tcagtccctt ccaccccatc | 360 |
| cggagagcgg ctgtgaagat tctggttcac tcgctcttca acatgctcat catgtgcacc | 420 |
| atcctcacca actgcgtgtt catggcccag acgaccctc caccctggac caagtatgtc | 480 |
| gagtacacct tcaccgccat ttacacccttt gagtctctgg tcaagattct ggctcgaggc | 540 |
| ttctgcctgc acgcgttcac tttccttcgg gacccatgga actggctgga ctttagtgtg | 600 |
| attatcatgg catacacaac tgaatttgtg gacctgggca atgtctcagc ttacgcacc | 660 |
| ttccgagtcc tccggcccct gaaaactata tcagtcattt cagggctgaa gaccatcgtg | 720 |
| ggggccctga tccagtctgt gaagaagctg gctgatgtga tggtcctcac agtcttctgc | 780 |
| ctcagcgtct ttgcccctcat cggcctgcag ctcttcatgg gcaacctaag gcacaagtgc | 840 |
| gtgcgcaact tcacagcgct caacggcacc aacggctccg tggaggccga cggcttggtc | 900 |
| tgggaatccc tggacctta cctcagtgat ccagaaaatt acctgctcaa gaacggcacc | 960 |
| tctgatgtgt actgtgtgg aacagctct gacgctggga catgtccgga gggctaccgg | 1020 |
| tgcctaaagg caggcgagaa ccccgaccac ggctacacca gcttcgattc ctttgcctgg | 1080 |
| gcctttcttg cactcttccg cctgatgacg caggactgct gggagcgcct ctatcagcag | 1140 |
| accctcaggt ccgcagggaa gatctacatg atcttcttca tgcttgtcat cttcctgggg | 1200 |
| tccttctacc tggtgaacct gatcctggcc gtggtcgcaa tggcctatga ggagcaaaac | 1260 |
| caagccacca tcgctgagac cgaggagaag gaaaagcgct tccaggaggc catggaaatg | 1320 |
| ctcaagaaag aacacgaggc cctcaccatc agggtgtgg ataccgtgtc ccgtagctcc | 1380 |
| ttggagatgt cccctttggc cccagtaaac agccatgaga aagaagcaa gaggagaaaa | 1440 |
| cggatgtctt caggaactga ggagtgtggg aggacaggc tcccaagtc tgactcagaa | 1500 |
| gatggtccca gagcaatgaa tcatctcagc ctcacccgtg gcctcagcag gacttctatg | 1560 |

```
aagccacgtt ccagccgcgg gagcatttc accttcgca ggcgagacct gggttctgaa    1620
gcagattttg cagatgatga aaacagcaca gcggggggaga gcgagagcca ccacacatca   1680
ctgctggtgc cctggcccct gcgccggacc agtgcccagg acagcccag tcccggaacc   1740 tcggctcctg gccacgccct ccatggcaaa agaacagca ctgtggactg caatggggtg   1800
gtctcattac tgggggcagg cgacccagag gccacatccc caggaagcca cctcctccgc   1860
cctgtgatgc tagagcaccc gccagacacg accacgccat cggaggagcc aggcgggccc   1920
cagatgctga cctcccaggc tccgtgtgta gatggcttcg aggagccagg agcacggcag   1980 cgggcctca gcgcagtcag cgtcctcacc agcgcactgg aagagttaga ggagtctcgc   2040
cacaagtgtc caccatgctg gaaccgtctc gcccagcgct acctgatctg ggagtgctgc   2100
ccgctgtgga tgtccatcaa gcagggagtg aagttggtgg tcatggaccc gtttactgac   2160
ctcaccatca ctatgtgcat cgtactcaac acactcttca tggcgctgga gcactacaac   2220
atgacaagtg aattcgagga gatgctgcag gtcggaaacc tggtcttcac agggattttc   2280
acagcagaga tgaccttcaa gatcattgcc ctcgacccct actactactt ccaacagggc   2340
tggaacatct tcgacagcat catcgtcatc cttagcctca tggagctggg cctgtccgc   2400 atgagcaact tgtcggtgct gcgctccttc cgcctgctgc gggtcttcaa gctggccaaa   2460
tcatggccca ccctgaacac actcatcaag atcatcggga actcagtggg ggcactgggg   2520
aacctgacac tggtgctagc catcatcgtg ttcatctttg ctgtggtggg catgcagctc   2580
tttggcaaga actactcgga gctgagggac agcgactcag gcctgctgcc tcgctggcac   2640
atgatggact tctttcatgc cttcctcatc atcttccgca tcctctgtgg agagtggatc   2700
gagaccatgt gggactgcat ggaggtgtcg gggcagtcat tatgcctgct ggtcttcttg   2760
cttgttatgg tcattggcaa ccttgtggtc ctgaatctct tcctggcctt gctgctcagc   2820
tccttcagtg cagacaacct cacagcccct gatgaggaca gagagatgaa caacctccag   2880
ctggccctgg cccgcatcca gaggggcctg cgctttgtca gcggaccac ctgggatttc   2940 tgctgtggtc tcctgcggca gcggcctcag aagcccgcag cccttgccgc ccagggccag   3000
ctgcccagct gcattgccac cccctactcc ccgccacccc cagagacgga aaggtgcct   3060 cccacccgca aggaaacacg gtttgaggaa ggcgagcaac caggccaggg cacccccggg   3120
gatccagagc ccgtgtgtgt gcccatcgct gtggccgagt cagacacaga tgaccaagaa   3180
gaagatgagg agaacagcct gggcacggag gaggagtcca gcaagcagca ggaatcccag   3240
cctgtgtccg gtggcccaga ggcccctccg gattccagga cctggagcca ggtgtcagcg   3300
actgcctcct ctgaggccga ggccagtgca tctcaggccg actggcggca gcagtggaaa   3360
gcggaacccc aggcccagg gtgcggtgag acccccagagg acagttgctc cgagggcagc   3420
acagcagaca tgaccaacac cgctgagctc ctggagcaga tccctgacct cggccaggat   3480
gtcaaggacc cagaggactg cttcactgaa ggctgtgtcc ggcgctgtcc ctgctgtgcg   3540
gtggacacca cacaggcccc agggaaggtc tggtggcggt tgcgcaagac ctgctaccac   3600
atcgtggagc acagctggtt cgagacattc atcatcttca tgatcctact cagcagtgga   3660
gcgctggcct tcgaggacat ctacctagag gagcggaaga ccatcaaggt tctgcttgag   3720
tatgccgaca agatgttcac atatgtcttc gtgctggaga tgctgctcaa gtgggtggcc   3780
tacggcttca agaagtactt caccaatgcc tggtgctggc tcgacttcct catcgtagac   3840
gtctctctgg tcagcctggt ggccaacacc ctgggctttg ccgagatggg ccccatcaag   3900
tcactgcgga cgctgcgtgc actccgtcct ctgagagctc tgtcacgatt tgagggcatg   3960
```

-continued

```
agggtggtgg tcaatgccct ggtgggcgcc atcccgtcca tcatgaacgt cctcctcgtc    4020
tgcctcatct tctggctcat cttcagcatc atgggcgtga acctctttgc ggggaagttt    4080
gggaggtgca tcaaccagac agagggagac ttgcctttga actacaccat cgtgaacaac    4140
aagagccagt gtgagtcctt gaacttgacc ggagaattgt actggaccaa ggtgaaagtc    4200
aactttgaca acgtggggc cgggtacctg gccttctgc aggtggcaac attttgcggc     4260
tggatggaca ttatgtatgc agctgtggac tccagggggt atgaagagca gcctcagtgg    4320
gaatacaacc tctacatgta catctatttt gtcattttca tcatctttgg gtctttcttc    4380
accctgaacc tctttattgg tgtcatcatt gacaacttca accaacagaa gaaaaagtta    4440
gggggccagg acatccagat gacagaggag cagaagaagt actacaatgc catgaagaag    4500
ctgggctcca agaagcccca gaagcccatc ccacggcccc tgaacaagta ccagggcttc    4560
atattcgaca ttgtgaccaa gcaggccttt gacgtcacca tcatgtttct gatctgcttg    4620
aatatggtga ccatgatggt ggagacagat gaccaaagtc ctgagaaaat caacatcttg    4680
gccaagatca acctgctctt tgtggccatc ttcacaggcg agtgtattgt caagctggct    4740
gccctgcgcc actactactt caccaacagc tggaatatct tcgacttcgt ggttgtcatc    4800
ctctccatcg tgggcactgt gctctcggac atcatccaga agtacttctt ctcccccgacg    4860 ctcttccgag tcatccgcct ggcccgaata ggccgcatcc tcagactgat ccgaggggcc    4920
aaggggatcc gcacgctgct cttcgccctc atgatgtccc tgcctgccct cttcaacatc    4980
gggctgctgc tcttcctcgt catgttcatc tactccatct ttggcatggc caacttcgct    5040
tatgtcaagt gggaggctgg catcgacgac atgttcaact ccagaccctt cgccaacagc    5100
atgctgtgcc tcttccagat caccacgtcg gccggctggg atggcctcct cagccccatc    5160
ctcaacactg gccgccccta ctgcgacccc actctgccca cagcaatgg ctctcggggg     5220 gactgcggga gcccagccgt gggcatcctc ttcttcacca cctacatcat catctccttc    5280
ctcatcgtgg tcaacatgta cattgccatc atcctggaga acttcagcgt ggccacggag    5340
gagagcaccg agcccctgag tgaggacgac ttcgatatgt tctatgagat ctgggagaaa    5400
tttgacccag aggccactca gtttattgag tattcggtcc tgtctgactt tgccgatgcc    5460
ctgtctgagc cactccgtat cgccaagccc aaccagataa gcctcatcaa catggacctg    5520
cccatggtga gtggggaccg catccattgc atggacattc tctttgcctt caccaaaagg    5580
gtcctggggg agtctgggga gatggacgcc ctgaagatcc agatggagga agttcatg      5640 gcagccaacc catccaagat ctcctacgag cccatcacca ccacactccg gcgcaagcac    5700
gaagaggtgt cggccatggt tatccagaga gccttccgca ggcacctgct gcaacgctct    5760
ttgaagcatg cctccttcct cttccgtcag caggcgggca gcggcctctc cgaagaggat    5820
gcccctgagc gagagggcct catcgcctac gtgatgagtg agaacttctc ccgaccccct    5880
ggccacccct ccagctcctc catctcctcc acttccttcc caccctccta tgacagtgtc    5940
actagagcca ccagcgataa cctccaggtg cgggggtctg actacagcca cagtgaagat    6000
ctcgccgact tccccccttc tccggacagg gaccgtgagt ccatcgtgtg a              6051
```

<210> SEQ ID NO 5
<211> LENGTH: 2016
<212> TYPE: PRT
<213> ORGANISM: Homo sapiens

<400> SEQUENCE: 5

```
Met Ala Asn Phe Leu Leu Pro Arg Gly Thr Ser Ser Phe Arg Arg Phe
1               5                   10                  15
```

-continued

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
            35                  40                  45

Glu Glu Ala Pro Arg Pro Gln Leu Asp Leu Gln Ala Ser Lys Lys Leu
 50                  55                  60

Pro Asp Leu Tyr Gly Asn Pro Pro Gln Glu Leu Ile Gly Glu Pro Leu
 65                  70                  75                  80

Glu Asp Leu Asp Pro Phe Tyr Ser Thr Gln Lys Thr Phe Ile Val Leu
                 85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
            115                 120                 125

Val His Ser Leu Phe Asn Met Leu Ile Met Cys Thr Ile Leu Thr Asn
        130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
            195                 200                 205

Phe Val Asp Leu Gly Asn Val Ser Ala Leu Arg Thr Phe Arg Val Leu
 210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
            275                 280                 285

Gly Thr Asn Gly Ser Val Glu Ala Asp Gly Leu Val Trp Glu Ser Leu
 290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
            355                 360                 365

Met Thr Gln Asp Cys Trp Glu Arg Leu Tyr Gln Gln Thr Leu Arg Ser
 370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
            420                 425                 430

Arg Phe Gln Glu Ala Met Glu Met Leu Lys Lys Glu His Glu Ala Leu

-continued

```
            435                 440                 445
Thr Ile Arg Gly Val Asp Thr Val Ser Arg Ser Leu Glu Met Ser
        450                 455                 460
Pro Leu Ala Pro Val Asn Ser His Glu Arg Arg Ser Lys Arg Lys
465                 470                 475                 480
Arg Met Ser Ser Gly Thr Glu Glu Cys Gly Glu Asp Arg Leu Pro Lys
                485                 490                 495
Ser Asp Ser Glu Asp Gly Pro Arg Ala Met Asn His Leu Ser Leu Thr
            500                 505                 510
Arg Gly Leu Ser Arg Thr Ser Met Lys Pro Arg Ser Ser Arg Gly Ser
            515                 520                 525
Ile Phe Thr Phe Arg Arg Arg Asp Leu Gly Ser Glu Ala Asp Phe Ala
            530                 535                 540
Asp Asp Glu Asn Ser Thr Ala Gly Glu Ser Glu Ser His His Thr Ser
545                 550                 555                 560
Leu Leu Val Pro Trp Pro Leu Arg Arg Thr Ser Ala Gln Gly Gln Pro
                565                 570                 575
Ser Pro Gly Thr Ser Ala Pro Gly His Ala Leu His Gly Lys Lys Asn
            580                 585                 590
Ser Thr Val Asp Cys Asn Gly Val Val Ser Leu Leu Gly Ala Gly Asp
            595                 600                 605
Pro Glu Ala Thr Ser Pro Gly Ser His Leu Leu Arg Pro Val Met Leu
            610                 615                 620
Glu His Pro Pro Asp Thr Thr Thr Pro Ser Glu Glu Pro Gly Gly Pro
625                 630                 635                 640
Gln Met Leu Thr Ser Gln Ala Pro Cys Val Asp Gly Phe Glu Glu Pro
                645                 650                 655
Gly Ala Arg Gln Arg Ala Leu Ser Ala Val Ser Val Leu Thr Ser Ala
                660                 665                 670
Leu Glu Glu Leu Glu Glu Ser Arg His Lys Cys Pro Pro Cys Trp Asn
            675                 680                 685
Arg Leu Ala Gln Arg Tyr Leu Ile Trp Glu Cys Cys Pro Leu Trp Met
            690                 695                 700
Ser Ile Lys Gln Gly Val Lys Leu Val Val Met Asp Pro Phe Thr Asp
705                 710                 715                 720
Leu Thr Ile Thr Met Cys Ile Val Leu Asn Thr Leu Phe Met Ala Leu
                725                 730                 735
Glu His Tyr Asn Met Thr Ser Glu Phe Glu Glu Met Leu Gln Val Gly
            740                 745                 750
Asn Leu Val Phe Thr Gly Ile Phe Thr Ala Glu Met Thr Phe Lys Ile
            755                 760                 765
Ile Ala Leu Asp Pro Tyr Tyr Tyr Phe Gln Gln Gly Trp Asn Ile Phe
            770                 775                 780
Asp Ser Ile Ile Val Ile Leu Ser Leu Met Glu Leu Gly Leu Ser Arg
785                 790                 795                 800
Met Ser Asn Leu Ser Val Leu Arg Ser Phe Arg Leu Leu Arg Val Phe
                805                 810                 815
Lys Leu Ala Lys Ser Trp Pro Thr Leu Asn Thr Leu Ile Lys Ile Ile
                820                 825                 830
Gly Asn Ser Val Gly Ala Leu Gly Asn Leu Thr Leu Val Leu Ala Ile
            835                 840                 845
Ile Val Phe Ile Phe Ala Val Val Gly Met Gln Leu Phe Gly Lys Asn
            850                 855                 860
```

```
Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
            885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
            915                 920                 925

Val Val Leu Asn Leu Phe Leu Ala Leu Leu Leu Ser Ser Phe Ser Ala
930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
            965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln Leu Pro Ser Cys Ile Ala Thr Pro
            995                 1000                1005

Tyr Ser Pro Pro Pro Pro Glu Thr Glu Lys Val Pro Pro Thr Arg
    1010                1015                1020

Lys Glu Thr Arg Phe Glu Glu Gly Glu Gln Pro Gly Gln Gly Thr
    1025                1030                1035

Pro Gly Asp Pro Glu Pro Val Cys Val Pro Ile Ala Val Ala Glu
    1040                1045                1050

Ser Asp Thr Asp Asp Gln Glu Glu Asp Glu Glu Asn Ser Leu Gly
    1055                1060                1065

Thr Glu Glu Glu Ser Ser Lys Gln Gln Glu Ser Gln Pro Val Ser
    1070                1075                1080

Gly Gly Pro Glu Ala Pro Pro Asp Ser Arg Thr Trp Ser Gln Val
    1085                1090                1095

Ser Ala Thr Ala Ser Ser Glu Ala Glu Ala Ser Ala Ser Gln Ala
    1100                1105                1110

Asp Trp Arg Gln Gln Trp Lys Ala Glu Pro Gln Ala Pro Gly Cys
    1115                1120                1125

Gly Glu Thr Pro Glu Asp Ser Cys Ser Glu Gly Ser Thr Ala Asp
    1130                1135                1140

Met Thr Asn Thr Ala Glu Leu Leu Glu Gln Ile Pro Asp Leu Gly
    1145                1150                1155

Gln Asp Val Lys Asp Pro Glu Asp Cys Phe Thr Glu Gly Cys Val
    1160                1165                1170

Arg Arg Cys Pro Cys Cys Ala Val Asp Thr Thr Gln Ala Pro Gly
    1175                1180                1185

Lys Val Trp Trp Arg Leu Arg Lys Thr Cys Tyr His Ile Val Glu
    1190                1195                1200

His Ser Trp Phe Glu Thr Phe Ile Ile Phe Met Ile Leu Leu Ser
    1205                1210                1215

Ser Gly Ala Leu Ala Phe Glu Asp Ile Tyr Leu Glu Glu Arg Lys
    1220                1225                1230

Thr Ile Lys Val Leu Leu Glu Tyr Ala Asp Lys Met Phe Thr Tyr
    1235                1240                1245

Val Phe Val Leu Glu Met Leu Leu Lys Trp Val Ala Tyr Gly Phe
    1250                1255                1260

Lys Lys Tyr Phe Thr Asn Ala Trp Cys Trp Leu Asp Phe Leu Ile
    1265                1270                1275
```

```
Val Asp Val Ser Leu Val Ser Leu Val Ala Asn Thr Leu Gly Phe
    1280            1285                1290

Ala Glu Met Gly Pro Ile Lys Ser Leu Arg Thr Leu Arg Ala Leu
    1295            1300                1305

Arg Pro Leu Arg Ala Leu Ser Arg Phe Glu Gly Met Arg Val Val
    1310            1315                1320

Val Asn Ala Leu Val Gly Ala Ile Pro Ser Ile Met Asn Val Leu
    1325            1330                1335

Leu Val Cys Leu Ile Phe Trp Leu Ile Phe Ser Ile Met Gly Val
    1340            1345                1350

Asn Leu Phe Ala Gly Lys Phe Gly Arg Cys Ile Asn Gln Thr Glu
    1355            1360                1365

Gly Asp Leu Pro Leu Asn Tyr Thr Ile Val Asn Asn Lys Ser Gln
    1370            1375                1380

Cys Glu Ser Leu Asn Leu Thr Gly Glu Leu Tyr Trp Thr Lys Val
    1385            1390                1395

Lys Val Asn Phe Asp Asn Val Gly Ala Gly Tyr Leu Ala Leu Leu
    1400            1405                1410

Gln Val Ala Thr Phe Cys Gly Trp Met Asp Ile Met Tyr Ala Ala
    1415            1420                1425

Val Asp Ser Arg Gly Tyr Glu Glu Gln Pro Gln Trp Glu Tyr Asn
    1430            1435                1440

Leu Tyr Met Tyr Ile Tyr Phe Val Ile Phe Ile Ile Phe Gly Ser
    1445            1450                1455

Phe Phe Thr Leu Asn Leu Phe Ile Gly Val Ile Ile Asp Asn Phe
    1460            1465                1470

Asn Gln Gln Lys Lys Lys Leu Gly Gly Gln Asp Ile Gln Met Thr
    1475            1480                1485

Glu Glu Gln Lys Lys Tyr Tyr Asn Ala Met Lys Lys Leu Gly Ser
    1490            1495                1500

Lys Lys Pro Gln Lys Pro Ile Pro Arg Pro Leu Asn Lys Tyr Gln
    1505            1510                1515

Gly Phe Ile Phe Asp Ile Val Thr Lys Gln Ala Phe Asp Val Thr
    1520            1525                1530

Ile Met Phe Leu Ile Cys Leu Asn Met Val Thr Met Met Val Glu
    1535            1540                1545

Thr Asp Asp Gln Ser Pro Glu Lys Ile Asn Ile Leu Ala Lys Ile
    1550            1555                1560

Asn Leu Leu Phe Val Ala Ile Phe Thr Gly Glu Cys Ile Val Lys
    1565            1570                1575

Leu Ala Ala Leu Arg His Tyr Tyr Phe Thr Asn Ser Trp Asn Ile
    1580            1585                1590

Phe Asp Phe Val Val Val Ile Leu Ser Ile Val Gly Thr Val Leu
    1595            1600                1605

Ser Asp Ile Ile Gln Lys Tyr Phe Phe Ser Pro Thr Leu Phe Arg
    1610            1615                1620

Val Ile Arg Leu Ala Arg Ile Gly Arg Ile Leu Arg Leu Ile Arg
    1625            1630                1635

Gly Ala Lys Gly Ile Arg Thr Leu Leu Phe Ala Leu Met Met Ser
    1640            1645                1650

Leu Pro Ala Leu Phe Asn Ile Gly Leu Leu Leu Phe Leu Val Met
    1655            1660                1665

Phe Ile Tyr Ser Ile Phe Gly Met Ala Asn Phe Ala Tyr Val Lys
```

```
            1670                1675               1680

Trp Glu Ala Gly Ile Asp Asp Met Phe Asn Phe Gln Thr Phe Ala
    1685                1690               1695

Asn Ser Met Leu Cys Leu Phe Gln Ile Thr Thr Ser Ala Gly Trp
    1700                1705               1710

Asp Gly Leu Leu Ser Pro Ile Leu Asn Thr Gly Pro Pro Tyr Cys
    1715                1720               1725

Asp Pro Thr Leu Pro Asn Ser Asn Gly Ser Arg Gly Asp Cys Gly
    1730                1735               1740

Ser Pro Ala Val Gly Ile Leu Phe Phe Thr Thr Tyr Ile Ile Ile
    1745                1750               1755

Ser Phe Leu Ile Val Val Asn Met Tyr Ile Ala Ile Ile Leu Glu
    1760                1765               1770

Asn Phe Ser Val Ala Thr Glu Glu Ser Thr Glu Pro Leu Ser Glu
    1775                1780               1785

Asp Asp Phe Asp Met Phe Tyr Glu Ile Trp Glu Lys Phe Asp Pro
    1790                1795               1800

Glu Ala Thr Gln Phe Ile Glu Tyr Ser Val Leu Ser Asp Phe Ala
    1805                1810               1815

Asp Ala Leu Ser Glu Pro Leu Arg Ile Ala Lys Pro Asn Gln Ile
    1820                1825               1830

Ser Leu Ile Asn Met Asp Leu Pro Met Val Ser Gly Asp Arg Ile
    1835                1840               1845

His Cys Met Asp Ile Leu Phe Ala Phe Thr Lys Arg Val Leu Gly
    1850                1855               1860

Glu Ser Gly Glu Met Asp Ala Leu Lys Ile Gln Met Glu Glu Lys
    1865                1870               1875

Phe Met Ala Ala Asn Pro Ser Lys Ile Ser Tyr Glu Pro Ile Thr
    1880                1885               1890

Thr Thr Leu Arg Arg Lys His Glu Glu Val Ser Ala Met Val Ile
    1895                1900               1905

Gln Arg Ala Phe Arg Arg His Leu Leu Gln Arg Ser Leu Lys His
    1910                1915               1920

Ala Ser Phe Leu Phe Arg Gln Gln Ala Gly Ser Gly Leu Ser Glu
    1925                1930               1935

Glu Asp Ala Pro Glu Arg Glu Gly Leu Ile Ala Tyr Val Met Ser
    1940                1945               1950

Glu Asn Phe Ser Arg Pro Leu Gly Pro Pro Ser Ser Ser Ser Ile
    1955                1960               1965

Ser Ser Thr Ser Phe Pro Pro Ser Tyr Asp Ser Val Thr Arg Ala
    1970                1975               1980

Thr Ser Asp Asn Leu Gln Val Arg Gly Ser Asp Tyr Ser His Ser
    1985                1990               1995

Glu Asp Leu Ala Asp Phe Pro Pro Ser Pro Asp Arg Asp Arg Glu
    2000                2005               2010

Ser Ile Val
    2015

<210> SEQ ID NO 6
<211> LENGTH: 8504
<212> TYPE: DNA
<213> ORGANISM: Homo sapiens
<220> FEATURE:
<221> NAME/KEY: CDS
<222> LOCATION: (195)..(6245)
```

-continued

```
<400> SEQUENCE: 6
agacggcggc ggcgcccgta ggatgcaggg atcgctcccc cggggccgct gagcctgcgc      60
ccagtgcccc gagccccgcg ccgagccgag tccgcgccaa gcagcagccg cccaccccgg     120
ggcccggccg gggaccagca gcttccccca caggcaacgt gaggagagcc tgtgcccaga     180
agcaggatga gaag atg gca aac ttc cta tta cct cgg ggc acc agc agc      230
             Met Ala Asn Phe Leu Leu Pro Arg Gly Thr Ser Ser
             1               5                   10 ttc cgc agg ttc aca cgg gag tcc ctg gca gcc atc gag aag cgc atg      278
Phe Arg Arg Phe Thr Arg Glu Ser Leu Ala Ala Ile Glu Lys Arg Met
            15                  20                  25 gca gag aag caa gcc cgc ggc tca acc acc ttg cag gag agc cga gag      326
Ala Glu Lys Gln Ala Arg Gly Ser Thr Thr Leu Gln Glu Ser Arg Glu
 30                  35                  40 ggg ctg ccc gag gag gag gct ccc cgg ccc cag ctg gac ctg cag gcc      374
Gly Leu Pro Glu Glu Glu Ala Pro Arg Pro Gln Leu Asp Leu Gln Ala
45                  50                  55                  60 tcc aaa aag ctg cca gat ctc tat ggc aat cca ccc caa gag ctc atc      422
Ser Lys Lys Leu Pro Asp Leu Tyr Gly Asn Pro Pro Gln Glu Leu Ile
                65                  70                  75 gga gag ccc ctg gag gac ctg gac ccc ttc tat agc acc caa aag act      470
Gly Glu Pro Leu Glu Asp Leu Asp Pro Phe Tyr Ser Thr Gln Lys Thr
            80                  85                  90 ttc atc gta ctg aat aaa ggc aag acc atc ttc cgg ttc agt gcc acc      518
Phe Ile Val Leu Asn Lys Gly Lys Thr Ile Phe Arg Phe Ser Ala Thr
        95                 100                 105 aac gcc ttg tat gtc ctc agt ccc ttc cac ccc atc cgg aga gcg gct      566
Asn Ala Leu Tyr Val Leu Ser Pro Phe His Pro Ile Arg Arg Ala Ala
    110                 115                 120 gtg aag att ctg gtt cac tcg ctc ttc aac atg ctc atc atg tgc acc      614
Val Lys Ile Leu Val His Ser Leu Phe Asn Met Leu Ile Met Cys Thr
125                 130                 135                 140 atc ctc acc aac tgc gtg ttc atg gcc cag cac gac cct cca ccc tgg      662
Ile Leu Thr Asn Cys Val Phe Met Ala Gln His Asp Pro Pro Pro Trp
                145                 150                 155 acc aag tat gtc gag tac acc ttc acc gcc att tac acc ttt gag tct      710
Thr Lys Tyr Val Glu Tyr Thr Phe Thr Ala Ile Tyr Thr Phe Glu Ser
            160                 165                 170 ctg gtc aag att ctg gct cga ggc ttc tgc ctg cac gcg ttc act ttc      758
Leu Val Lys Ile Leu Ala Arg Gly Phe Cys Leu His Ala Phe Thr Phe
        175                 180                 185 ctt cgg gac cca tgg aac tgg ctg gac ttt agt gtg att atc atg gca      806
Leu Arg Asp Pro Trp Asn Trp Leu Asp Phe Ser Val Ile Ile Met Ala
    190                 195                 200 tac aca act gaa ttt gtg gac ctg ggc aat gtc tca gcc tta cgc acc      854
Tyr Thr Thr Glu Phe Val Asp Leu Gly Asn Val Ser Ala Leu Arg Thr
205                 210                 215                 220 ttc cga gtc ctc cgg gcc ctg aaa act ata tca gtc att tca ggg ctg      902
Phe Arg Val Leu Arg Ala Leu Lys Thr Ile Ser Val Ile Ser Gly Leu
                225                 230                 235 aag acc atc gtg ggg gcc ctg atc cag tct gtg aag aag ctg gct gat      950
Lys Thr Ile Val Gly Ala Leu Ile Gln Ser Val Lys Lys Leu Ala Asp
            240                 245                 250 gtg atg gtc ctc aca gtc ttc tgc ctc agc gtc ttt gcc ctc atc ggc      998
Val Met Val Leu Thr Val Phe Cys Leu Ser Val Phe Ala Leu Ile Gly
        255                 260                 265 ctg cag ctc ttc atg ggc aac cta agg cac aag tgc gtg cgc aac ttc     1046
Leu Gln Leu Phe Met Gly Asn Leu Arg His Lys Cys Val Arg Asn Phe
    270                 275                 280
```

|  |  |  |  |  |  |  |  |  |  |  |  |  |  |  |  |
|---|---|---|---|---|---|---|---|---|---|---|---|---|---|---|---|
| aca | gcg | ctc | aac | ggc | acc | aac | ggc | tcc | gtg | gag | gcc | gac | ggc | ttg | gtc | 1094 |
| Thr | Ala | Leu | Asn | Gly | Thr | Asn | Gly | Ser | Val | Glu | Ala | Asp | Gly | Leu | Val |
| 285 | | | | | 290 | | | | | 295 | | | | | 300 |

```
aca gcg ctc aac ggc acc aac ggc tcc gtg gag gcc gac ggc ttg gtc      1094
Thr Ala Leu Asn Gly Thr Asn Gly Ser Val Glu Ala Asp Gly Leu Val
285                 290                 295                 300 tgg gaa tcc ctg gac ctt tac ctc agt gat cca gaa aat tac ctg ctc      1142
Trp Glu Ser Leu Asp Leu Tyr Leu Ser Asp Pro Glu Asn Tyr Leu Leu
                305                 310                 315 aag aac ggc acc tct gat gtg tta ctg tgt ggg aac agc tct gac gct      1190
Lys Asn Gly Thr Ser Asp Val Leu Leu Cys Gly Asn Ser Ser Asp Ala
            320                 325                 330 ggg aca tgt ccg gag ggc tac cgg tgc cta aag gca ggc gag aac ccc      1238
Gly Thr Cys Pro Glu Gly Tyr Arg Cys Leu Lys Ala Gly Glu Asn Pro
                335                 340                 345 gac cac ggc tac acc agc ttc gat tcc ttt gcc tgg gcc ttt ctt gca      1286
Asp His Gly Tyr Thr Ser Phe Asp Ser Phe Ala Trp Ala Phe Leu Ala
        350                 355                 360 ctc ttc cgc ctg atg acg cag gac tgc tgg gag cgc ctc tat cag cag      1334
Leu Phe Arg Leu Met Thr Gln Asp Cys Trp Glu Arg Leu Tyr Gln Gln
365                 370                 375                 380 acc ctc agg tcc gca ggg aag atc tac atg atc ttc ttc atg ctt gtc      1382
Thr Leu Arg Ser Ala Gly Lys Ile Tyr Met Ile Phe Phe Met Leu Val
                385                 390                 395 atc ttc ctg ggg tcc ttc tac ctg gtg aac ctg atc ctg gcc gtg gtc      1430
Ile Phe Leu Gly Ser Phe Tyr Leu Val Asn Leu Ile Leu Ala Val Val
            400                 405                 410 gca atg gcc tat gag gag caa aac caa gcc acc atc gct gag acc gag      1478
Ala Met Ala Tyr Glu Glu Gln Asn Gln Ala Thr Ile Ala Glu Thr Glu
        415                 420                 425 gag aag gaa aag cgc ttc cag gag gcc atg gaa atg ctc aag aaa gaa      1526
Glu Lys Glu Lys Arg Phe Gln Glu Ala Met Glu Met Leu Lys Lys Glu
430                 435                 440 cac gag gcc ctc acc atc agg ggt gtg gat acc gtg tcc cgt agc tcc      1574
His Glu Ala Leu Thr Ile Arg Gly Val Asp Thr Val Ser Arg Ser Ser
445                 450                 455                 460 ttg gag atg tcc cct ttg gcc cca gta aac agc cat gag aga aga agc      1622
Leu Glu Met Ser Pro Leu Ala Pro Val Asn Ser His Glu Arg Arg Ser
                465                 470                 475 aag agg aga aaa cgg atg tct tca gga act gag gag tgt ggg gag gac      1670
Lys Arg Arg Lys Arg Met Ser Ser Gly Thr Glu Glu Cys Gly Glu Asp
            480                 485                 490 agg ctc ccc aag tct gac tca gaa gat ggt ccc aga gca atg aat cat      1718
Arg Leu Pro Lys Ser Asp Ser Glu Asp Gly Pro Arg Ala Met Asn His
        495                 500                 505 ctc agc ctc acc cgt ggc ctc agc agg act tct atg aag cca cgt tcc      1766
Leu Ser Leu Thr Arg Gly Leu Ser Arg Thr Ser Met Lys Pro Arg Ser
510                 515                 520 agc cgc ggg agc att ttc acc ttt cgc agg cga gac ctg ggt tct gaa      1814
Ser Arg Gly Ser Ile Phe Thr Phe Arg Arg Arg Asp Leu Gly Ser Glu
525                 530                 535                 540 gca gat ttt gca gat gat gaa aac agc aca gcg ggg gag agc gag agc      1862
Ala Asp Phe Ala Asp Asp Glu Asn Ser Thr Ala Gly Glu Ser Glu Ser
                545                 550                 555 cac cac aca tca ctg ctg gtg ccc tgg ccc ctg cgg acc agt gcc      1910
His His Thr Ser Leu Leu Val Pro Trp Pro Leu Arg Arg Thr Ser Ala
            560                 565                 570 cag gga cag ccc agt ccc gga acc tcg gct cct ggc cac gcc ctc cat      1958
Gln Gly Gln Pro Ser Pro Gly Thr Ser Ala Pro Gly His Ala Leu His
        575                 580                 585 ggc aaa aag aac agc act gtg gac tgc aat ggg gtg gtc tca tta ctg      2006
Gly Lys Lys Asn Ser Thr Val Asp Cys Asn Gly Val Val Ser Leu Leu
590                 595                 600
```

```
ggg gca ggc gac cca gag gcc aca tcc cca gga agc cac ctc ctc cgc      2054
Gly Ala Gly Asp Pro Glu Ala Thr Ser Pro Gly Ser His Leu Leu Arg
605                 610                 615                 620 cct gtg atg cta gag cac ccg cca gac acg acc acg cca tcg gag gag      2102
Pro Val Met Leu Glu His Pro Pro Asp Thr Thr Thr Pro Ser Glu Glu
                625                 630                 635 cca ggc ggg ccc cag atg ctg acc tcc cag gct ccg tgt gta gat ggc      2150
Pro Gly Gly Pro Gln Met Leu Thr Ser Gln Ala Pro Cys Val Asp Gly
            640                 645                 650 ttc gag gag cca gga gca cgg cag cgg gcc ctc agc gca gtc agc gtc      2198
Phe Glu Glu Pro Gly Ala Arg Gln Arg Ala Leu Ser Ala Val Ser Val
        655                 660                 665 ctc acc agc gca ctg gaa gag tta gag gag tct cgc cac aag tgt cca      2246
Leu Thr Ser Ala Leu Glu Glu Leu Glu Glu Ser Arg His Lys Cys Pro
    670                 675                 680 cca tgc tgg aac cgt ctc gcc cag cgc tac ctg atc tgg gag tgc tgc      2294
Pro Cys Trp Asn Arg Leu Ala Gln Arg Tyr Leu Ile Trp Glu Cys Cys
685                 690                 695                 700 ccg ctg tgg atg tcc atc aag cag gga gtg aag ttg gtg gtc atg gac      2342
Pro Leu Trp Met Ser Ile Lys Gln Gly Val Lys Leu Val Val Met Asp
                705                 710                 715 ccg ttt act gac ctc acc atc act atg tgc atc gta ctc aac aca ctc      2390
Pro Phe Thr Asp Leu Thr Ile Thr Met Cys Ile Val Leu Asn Thr Leu
            720                 725                 730 ttc atg gcg ctg gag cac tac aac atg aca agt gaa ttc gag gag atg      2438
Phe Met Ala Leu Glu His Tyr Asn Met Thr Ser Glu Phe Glu Glu Met
        735                 740                 745 ctg cag gtc gga aac ctg gtc ttc aca ggg att ttc aca gca gag atg      2486
Leu Gln Val Gly Asn Leu Val Phe Thr Gly Ile Phe Thr Ala Glu Met
    750                 755                 760 acc ttc aag atc att gcc ctc gac ccc tac tac tac ttc caa cag ggc      2534
Thr Phe Lys Ile Ile Ala Leu Asp Pro Tyr Tyr Tyr Phe Gln Gln Gly
765                 770                 775                 780 tgg aac atc ttc gac agc atc atc gtc atc ctt agc ctc atg gag ctg      2582
Trp Asn Ile Phe Asp Ser Ile Ile Val Ile Leu Ser Leu Met Glu Leu
                785                 790                 795 ggc ctg tcc cgc atg agc aac ttg tcg gtg ctg cgc tcc ttc cgc ctg      2630
Gly Leu Ser Arg Met Ser Asn Leu Ser Val Leu Arg Ser Phe Arg Leu
            800                 805                 810 ctg cgg gtc ttc aag ctg gcc aaa tca tgg ccc acc ctg aac aca ctc      2678
Leu Arg Val Phe Lys Leu Ala Lys Ser Trp Pro Thr Leu Asn Thr Leu
        815                 820                 825 atc aag atc atc ggg aac tca gtg ggg gca ctg ggg aac ctg aca ctg      2726
Ile Lys Ile Ile Gly Asn Ser Val Gly Ala Leu Gly Asn Leu Thr Leu
    830                 835                 840 gtg cta gcc atc atc gtg ttc atc ttt gct gtg gtg ggc atg cag ctc      2774
Val Leu Ala Ile Ile Val Phe Ile Phe Ala Val Val Gly Met Gln Leu
845                 850                 855                 860 ttt ggc aag aac tac tcg gag ctg agg gac agc gac tca ggc ctg ctg      2822
Phe Gly Lys Asn Tyr Ser Glu Leu Arg Asp Ser Asp Ser Gly Leu Leu
                865                 870                 875 cct cgc tgg cac atg atg gac ttc ttt cat gcc ttc ctc atc atc ttc      2870
Pro Arg Trp His Met Met Asp Phe Phe His Ala Phe Leu Ile Ile Phe
            880                 885                 890 cgc atc ctc tgt gga gag tgg atc gag acc atg tgg gac tgc atg gag      2918
Arg Ile Leu Cys Gly Glu Trp Ile Glu Thr Met Trp Asp Cys Met Glu
        895                 900                 905 gtg tcg ggg cag tca tta tgc ctg ctg gtc ttc ttg ctt gtt atg gtc      2966
Val Ser Gly Gln Ser Leu Cys Leu Leu Val Phe Leu Leu Val Met Val
    910                 915                 920
```

```
att ggc aac ctt gtg gtc ctg aat ctc ttc ctg gcc ttg ctg ctc agc    3014
Ile Gly Asn Leu Val Val Leu Asn Leu Phe Leu Ala Leu Leu Leu Ser
925                 930                 935                 940 tcc ttc agt gca gac aac ctc aca gcc cct gat gag gac aga gag atg    3062
Ser Phe Ser Ala Asp Asn Leu Thr Ala Pro Asp Glu Asp Arg Glu Met
            945                 950                 955 aac aac ctc cag ctg gcc ctg gcc cgc atc cag agg ggc ctg cgc ttt    3110
Asn Asn Leu Gln Leu Ala Leu Ala Arg Ile Gln Arg Gly Leu Arg Phe
        960                 965                 970 gtc aag cgg acc acc tgg gat ttc tgc tgt ggt ctc ctg cgg cag cgg    3158
Val Lys Arg Thr Thr Trp Asp Phe Cys Cys Gly Leu Leu Arg Gln Arg
    975                 980                 985 cct cag aag ccc gca gcc ctt gcc gcc cag ggc cag ctg ccc agc tgc    3206
Pro Gln Lys Pro Ala Ala Leu Ala Ala Gln Gly Gln Leu Pro Ser Cys
990                 995                 1000 att gcc acc ccc tac tcc ccg cca ccc cca gag acg gag aag gtg        3251
Ile Ala Thr Pro Tyr Ser Pro Pro Pro Pro Glu Thr Glu Lys Val
1005                1010                1015 cct ccc acc cgc aag gaa aca cgg ttt gag gaa ggc gag caa cca        3296
Pro Pro Thr Arg Lys Glu Thr Arg Phe Glu Glu Gly Glu Gln Pro
1020                1025                1030 ggc cag ggc acc ccc ggg gat cca gag ccc gtg tgt gtg ccc atc        3341
Gly Gln Gly Thr Pro Gly Asp Pro Glu Pro Val Cys Val Pro Ile
1035                1040                1045 gct gtg gcc gag tca gac aca gat gac caa gaa gaa gat gag gag        3386
Ala Val Ala Glu Ser Asp Thr Asp Asp Gln Glu Glu Asp Glu Glu
1050                1055                1060 aac agc ctg ggc acg gag gag gag tcc agc aag cag cag gaa tcc        3431
Asn Ser Leu Gly Thr Glu Glu Glu Ser Ser Lys Gln Gln Glu Ser
1065                1070                1075 cag cct gtg tcc ggt ggc cca gag gcc cct ccg gat tcc agg acc        3476
Gln Pro Val Ser Gly Gly Pro Glu Ala Pro Pro Asp Ser Arg Thr
1080                1085                1090 tgg agc cag gtg tca gcg act gcc tcc tct gag gcc gag gcc agt        3521
Trp Ser Gln Val Ser Ala Thr Ala Ser Ser Glu Ala Glu Ala Ser
1095                1100                1105 gca tct cag gcc gac tgg cgg cag cag tgg aaa gcg gaa ccc cag        3566
Ala Ser Gln Ala Asp Trp Arg Gln Gln Trp Lys Ala Glu Pro Gln
1110                1115                1120 gcc cca ggg tgc ggt gag acc cca gag gac agt tgc tcc gag ggc        3611
Ala Pro Gly Cys Gly Glu Thr Pro Glu Asp Ser Cys Ser Glu Gly
1125                1130                1135 agc aca gca gac atg acc aac acc gct gag ctc ctg gag cag atc        3656
Ser Thr Ala Asp Met Thr Asn Thr Ala Glu Leu Leu Glu Gln Ile
1140                1145                1150 cct gac ctc ggc cag gat gtc aag gac cca gag gac tgc ttc act        3701
Pro Asp Leu Gly Gln Asp Val Lys Asp Pro Glu Asp Cys Phe Thr
1155                1160                1165 gaa ggc tgt gtc cgg cgc tgt ccc tgc tgt gcg gtg gac acc aca        3746
Glu Gly Cys Val Arg Arg Cys Pro Cys Cys Ala Val Asp Thr Thr
1170                1175                1180 cag gcc cca ggg aag gtc tgg tgg cgg ttg cgc aag acc tgc tac        3791
Gln Ala Pro Gly Lys Val Trp Trp Arg Leu Arg Lys Thr Cys Tyr
1185                1190                1195 cac atc gtg gag cac agc tgg ttc gag aca ttc atc atc ttc atg        3836
His Ile Val Glu His Ser Trp Phe Glu Thr Phe Ile Ile Phe Met
1200                1205                1210 atc cta ctc agc agt gga gcg ctg gcc ttc gag gac atc tac cta        3881
Ile Leu Leu Ser Ser Gly Ala Leu Ala Phe Glu Asp Ile Tyr Leu
1215                1220                1225
```

```
gag gag cgg aag acc atc aag gtt ctg ctt gag tat gcc gac aag       3926
Glu Glu Arg Lys Thr Ile Lys Val Leu Leu Glu Tyr Ala Asp Lys
1230                1235                1240 atg ttc aca tat gtc ttc gtg ctg gag atg ctg ctc aag tgg gtg       3971
Met Phe Thr Tyr Val Phe Val Leu Glu Met Leu Leu Lys Trp Val
1245                1250                1255 gcc tac ggc ttc aag aag tac ttc acc aat gcc tgg tgc tgg ctc       4016
Ala Tyr Gly Phe Lys Lys Tyr Phe Thr Asn Ala Trp Cys Trp Leu
1260                1265                1270 gac ttc ctc atc gta gac gtc tct ctg gtc agc ctg gtg gcc aac       4061
Asp Phe Leu Ile Val Asp Val Ser Leu Val Ser Leu Val Ala Asn
1275                1280                1285 acc ctg ggc ttt gcc gag atg ggc ccc atc aag tca ctg cgg acg       4106
Thr Leu Gly Phe Ala Glu Met Gly Pro Ile Lys Ser Leu Arg Thr
1290                1295                1300 ctg cgt gca ctc cgt cct ctg aga gct ctg tca cga ttt gag ggc       4151
Leu Arg Ala Leu Arg Pro Leu Arg Ala Leu Ser Arg Phe Glu Gly
1305                1310                1315 atg agg gtg gtg gtc aat gcc ctg gtg ggc gcc atc ccg tcc atc       4196
Met Arg Val Val Val Asn Ala Leu Val Gly Ala Ile Pro Ser Ile
1320                1325                1330 atg aac gtc ctc ctc gtc tgc ctc atc ttc tgg ctc atc ttc agc       4241
Met Asn Val Leu Leu Val Cys Leu Ile Phe Trp Leu Ile Phe Ser
1335                1340                1345 atc atg ggc gtg aac ctc ttt gcg ggg aag ttt ggg agg tgc atc       4286
Ile Met Gly Val Asn Leu Phe Ala Gly Lys Phe Gly Arg Cys Ile
1350                1355                1360 aac cag aca gag gga gac ttg cct ttg aac tac acc atc gtg aac       4331
Asn Gln Thr Glu Gly Asp Leu Pro Leu Asn Tyr Thr Ile Val Asn
1365                1370                1375 aac aag agc cag tgt gag tcc ttg aac ttg acc gga gaa ttg tac       4376
Asn Lys Ser Gln Cys Glu Ser Leu Asn Leu Thr Gly Glu Leu Tyr
1380                1385                1390 tgg acc aag gtg aaa gtc aac ttt gac aac gtg ggg gcc ggg tac       4421
Trp Thr Lys Val Lys Val Asn Phe Asp Asn Val Gly Ala Gly Tyr
1395                1400                1405 ctg gcc ctt ctg cag gtg gca aca ttt aaa ggc tgg atg gac att       4466
Leu Ala Leu Leu Gln Val Ala Thr Phe Lys Gly Trp Met Asp Ile
1410                1415                1420 atg tat gca gct gtg gac tcc agg ggg tat gaa gag cag cct cag       4511
Met Tyr Ala Ala Val Asp Ser Arg Gly Tyr Glu Glu Gln Pro Gln
1425                1430                1435 tgg gaa tac aac ctc tac atg tac atc tat ttt gtc att ttc atc       4556
Trp Glu Tyr Asn Leu Tyr Met Tyr Ile Tyr Phe Val Ile Phe Ile
1440                1445                1450 atc ttt ggg tct ttc ttc acc ctg aac ctc ttt att ggt gtc atc       4601
Ile Phe Gly Ser Phe Phe Thr Leu Asn Leu Phe Ile Gly Val Ile
1455                1460                1465 att gac aac ttc aac caa cag aag aaa aag tta ggg ggc cag gac       4646
Ile Asp Asn Phe Asn Gln Gln Lys Lys Lys Leu Gly Gly Gln Asp
1470                1475                1480 atc ttc atg aca gag gag cag aag aag tac tac aat gcc atg aag       4691
Ile Phe Met Thr Glu Glu Gln Lys Lys Tyr Tyr Asn Ala Met Lys
1485                1490                1495 aag ctg ggc tcc aag aag ccc cag aag ccc atc cca cgg ccc ctg       4736
Lys Leu Gly Ser Lys Lys Pro Gln Lys Pro Ile Pro Arg Pro Leu
1500                1505                1510 aac aag tac cag ggc ttc ata ttc gac att gtg acc aag cag gcc       4781
Asn Lys Tyr Gln Gly Phe Ile Phe Asp Ile Val Thr Lys Gln Ala
1515                1520                1525
```

```
ttt gac gtc acc atc atg ttt ctg atc tgc ttg aat atg gtg acc       4826
Phe Asp Val Thr Ile Met Phe Leu Ile Cys Leu Asn Met Val Thr
1530                1535                1540 atg atg gtg gag aca gat gac caa agt cct gag aaa atc aac atc       4871
Met Met Val Glu Thr Asp Asp Gln Ser Pro Glu Lys Ile Asn Ile
1545                1550                1555 ttg gcc aag atc aac ctg ctc ttt gtg gcc atc ttc aca ggc gag       4916
Leu Ala Lys Ile Asn Leu Leu Phe Val Ala Ile Phe Thr Gly Glu
1560                1565                1570 tgt att gtc aag ctg gct gcc ctg cgc cac tac tac ttc acc aac       4961
Cys Ile Val Lys Leu Ala Ala Leu Arg His Tyr Tyr Phe Thr Asn
1575                1580                1585 agc tgg aat atc ttc gac ttc gtg gtt gtc atc ctc tcc atc gtg       5006
Ser Trp Asn Ile Phe Asp Phe Val Val Val Ile Leu Ser Ile Val
1590                1595                1600 ggc act gtg ctc tcg gac atc atc cag aag tac ttc ttc tcc ccg       5051
Gly Thr Val Leu Ser Asp Ile Ile Gln Lys Tyr Phe Phe Ser Pro
1605                1610                1615 acg ctc ttc cga gtc atc cgc ctg gcc cga ata ggc cgc atc ctc       5096
Thr Leu Phe Arg Val Ile Arg Leu Ala Arg Ile Gly Arg Ile Leu
1620                1625                1630 aga ctg atc cga ggg gcc aag ggg atc cgc acg ctg ctc ttt gcc       5141
Arg Leu Ile Arg Gly Ala Lys Gly Ile Arg Thr Leu Leu Phe Ala
1635                1640                1645 ctc atg atg tcc ctg cct gcc ctc ttc aac atc ggg ctg ctc ctc       5186
Leu Met Met Ser Leu Pro Ala Leu Phe Asn Ile Gly Leu Leu Leu
1650                1655                1660 ttc ctc gtc atg ttc atc tac tcc atc ttt ggc atg gcc aac ttc       5231
Phe Leu Val Met Phe Ile Tyr Ser Ile Phe Gly Met Ala Asn Phe
1665                1670                1675 gct tat gtc aag tgg gag gct ggc atc gac gac atg ttc aac ttc       5276
Ala Tyr Val Lys Trp Glu Ala Gly Ile Asp Asp Met Phe Asn Phe
1680                1685                1690 cag acc ttc gcc aac agc atg ctg tgc ctc ttc cag atc acc acg       5321
Gln Thr Phe Ala Asn Ser Met Leu Cys Leu Phe Gln Ile Thr Thr
1695                1700                1705 tcg gcc ggc tgg gat ggc ctc ctc agc ccc atc ctc aac act ggg       5366
Ser Ala Gly Trp Asp Gly Leu Leu Ser Pro Ile Leu Asn Thr Gly
1710                1715                1720 ccg ccc tac tgc gac ccc act ctg ccc aac agc aat ggc tct cgg       5411
Pro Pro Tyr Cys Asp Pro Thr Leu Pro Asn Ser Asn Gly Ser Arg
1725                1730                1735 ggg gac tgc ggg agc cca gcc gtg ggc atc ctc ttc ttc acc acc       5456
Gly Asp Cys Gly Ser Pro Ala Val Gly Ile Leu Phe Phe Thr Thr
1740                1745                1750 tac atc atc atc tcc ttc ctc atc gtg gtc aac atg tac att gcc       5501
Tyr Ile Ile Ile Ser Phe Leu Ile Val Val Asn Met Tyr Ile Ala
1755                1760                1765 atc atc ctg gag aac ttc agc gtg gcc acg gag gag agc acc gag       5546
Ile Ile Leu Glu Asn Phe Ser Val Ala Thr Glu Glu Ser Thr Glu
1770                1775                1780 ccc ctg agt gag gac gac ttc gat atg ttc tat gag atc tgg gag       5591
Pro Leu Ser Glu Asp Asp Phe Asp Met Phe Tyr Glu Ile Trp Glu
1785                1790                1795 aaa ttt gac cca gag gcc act cag ttt att gag tat tcg gtc ctg       5636
Lys Phe Asp Pro Glu Ala Thr Gln Phe Ile Glu Tyr Ser Val Leu
1800                1805                1810 tct gac ttt gcc gat gcc ctg tct gag cca ctc cgt atc gcc aag       5681
Ser Asp Phe Ala Asp Ala Leu Ser Glu Pro Leu Arg Ile Ala Lys
1815                1820                1825
```

| | | | | | | | | | | | | |
|---|---|---|---|---|---|---|---|---|---|---|---|---|
| ccc | aac | cag | ata | agc | ctc | atc | aac | atg | gac | ctg | ccc atg gtg agt | 5726 |
| Pro | Asn | Gln | Ile | Ser | Leu | Ile | Asn | Met | Asp | Leu | Pro Met Val Ser | |
| 1830 | | | | 1835 | | | | | 1840 | | | |
| ggg | gac | cgc | atc | cat | tgc | atg | gac | att | ctc | ttt | gcc ttc acc aaa | 5771 |
| Gly | Asp | Arg | Ile | His | Cys | Met | Asp | Ile | Leu | Phe | Ala Phe Thr Lys | |
| 1845 | | | | 1850 | | | | | 1855 | | | |
| agg | gtc | ctg | ggg | gag | tct | ggg | gag | atg | gac | gcc | ctg aag atc cag | 5816 |
| Arg | Val | Leu | Gly | Glu | Ser | Gly | Glu | Met | Asp | Ala | Leu Lys Ile Gln | |
| 1860 | | | | 1865 | | | | | 1870 | | | |
| atg | gag | gag | aag | ttc | atg | gca | gcc | aac | cca | tcc | aag atc tcc tac | 5861 |
| Met | Glu | Glu | Lys | Phe | Met | Ala | Ala | Asn | Pro | Ser | Lys Ile Ser Tyr | |
| 1875 | | | | 1880 | | | | | 1885 | | | |
| gag | ccc | atc | acc | acc | aca | ctc | cgg | cgc | aag | cac | gaa gag gtg tcg | 5906 |
| Glu | Pro | Ile | Thr | Thr | Thr | Leu | Arg | Arg | Lys | His | Glu Glu Val Ser | |
| 1890 | | | | 1895 | | | | | 1900 | | | |
| gcc | atg | gtt | atc | cag | aga | gcc | ttc | cgc | agg | cac | ctg ctg caa cgc | 5951 |
| Ala | Met | Val | Ile | Gln | Arg | Ala | Phe | Arg | Arg | His | Leu Leu Gln Arg | |
| 1905 | | | | 1910 | | | | | 1915 | | | |
| tct | ttg | aag | cat | gcc | tcc | ttc | ctc | ttc | cgt | cag | cag gcg ggc agc | 5996 |
| Ser | Leu | Lys | His | Ala | Ser | Phe | Leu | Phe | Arg | Gln | Gln Ala Gly Ser | |
| 1920 | | | | 1925 | | | | | 1930 | | | |
| ggc | ctc | tcc | gaa | gag | gat | gcc | cct | gag | cga | gag | ggc ctc atc gcc | 6041 |
| Gly | Leu | Ser | Glu | Glu | Asp | Ala | Pro | Glu | Arg | Glu | Gly Leu Ile Ala | |
| 1935 | | | | 1940 | | | | | 1945 | | | |
| tac | gtg | atg | agt | gag | aac | ttc | tcc | cga | ccc | ctt | ggc cca ccc tcc | 6086 |
| Tyr | Val | Met | Ser | Glu | Asn | Phe | Ser | Arg | Pro | Leu | Gly Pro Pro Ser | |
| 1950 | | | | 1955 | | | | | 1960 | | | |
| agc | tcc | tcc | atc | tcc | tcc | act | tcc | ttc | cca | ccc | tcc tat gac agt | 6131 |
| Ser | Ser | Ser | Ile | Ser | Ser | Thr | Ser | Phe | Pro | Pro | Ser Tyr Asp Ser | |
| 1965 | | | | 1970 | | | | | 1975 | | | |
| gtc | act | aga | gcc | acc | agc | gat | aac | ctc | cag | gtg | cgg ggg tct gac | 6176 |
| Val | Thr | Arg | Ala | Thr | Ser | Asp | Asn | Leu | Gln | Val | Arg Gly Ser Asp | |
| 1980 | | | | 1985 | | | | | 1990 | | | |
| tac | agc | cac | agt | gaa | gat | ctc | gcc | gac | ttc | ccc | cct tct ccg gac | 6221 |
| Tyr | Ser | His | Ser | Glu | Asp | Leu | Ala | Asp | Phe | Pro | Pro Ser Pro Asp | |
| 1995 | | | | 2000 | | | | | 2005 | | | |
| agg | gac | cgt | gag | tcc | atc | gtg | tga | gcctcggcct ggctggccag | | | | 6265 |
| Arg | Asp | Arg | Glu | Ser | Ile | Val | | | | | | |
| 2010 | | | | 2015 | | | | | | | | |

```
gacacactga aaagcagcct ttttcaccat ggcaaaccta atgcagtca gtcacaaacc      6325
agcctggggc cttcctggct ttgggagtaa gaaatgggcc tcagcccgc ggatcaacca       6385
ggcagagttc tgtggcgccg cgtgacagc cggagcagtt ggcctgtgct tggaggcctc       6445
agatagacct gtgacctggt ctggtcaggc aatgccctgc ggctctggaa agcaacttca      6505
tcccagctgc tgaggcgaaa tataaaactg agactgtata tgttgtgaat gggcttttcat    6565
aaatttatta tatttgatat ttttttactt gagcaaagaa ctaaggattt ttccatggac     6625
atgggcagca attcacgctg tctcttctta accctgaaca agagtgtcta tggagcagcc     6685
ggaagtctgt tctcaaagca gaagtggaat ccagtgtggc tcccacaggt cttcactgcc     6745
caggggtcga atggggtccc cctcccactt gacctgagat gctgggaggg ctgaaccccc     6805
actcacacaa gcacacacac acagtcctca cacacggagg ccagacacag gccgtgggac     6865
ccaggctccc agcctaaggg agacaggcct ttccctgccg gccccccaag gatgggttc     6925
ttgtccacgg ggctcactct ggcccccctat tgtctccaag gtcccatttt cccctgtgt    6985
tttcacgcag gtcatattgt cagtcctaca aaaataaaag gcttcagag gagagtggcc     7045
tgggtcccag ggctggccct aggcactgat agttgccttt tcttcccctc ctgtaagagt    7105
```

```
attaacaaaa ccaaaggaca caagggtgca agccccattc acggcctggc atgcagcttg    7165
tccttgctcc tggaacctgg caggccctgc ccagccagcc atcggaagag agggctgagc    7225
catgggggtt tggggctaag aagttcacca gccctgagcc atggcggccc ctcagcctgc    7285
ctgaagagag gaaactggcg atctcccagg gctctctgga ccatacgcgg aggagttttc    7345
tgtgtggtct ccagctcctc tccagacaca gagacatggg agtggggagc ggagcttggc    7405
cctgcgccct gtgcagggaa agggatggtc aggcccagtt ctcgtgccct tagaggggaa    7465
tgaaccatgg caccttttgag agaggggca ctgtggtcag gcccagcctc tctggctcag    7525
cccgggatcc tgatggcacc cacacagagg acctcttttgg ggcaagatcc aggtggtccc    7585
ataggtcttg tgaaaaggct ttttcaggga aaaatatttt actagtccaa tcaccccag    7645
gacctcttca gctgctgaca atcctattta gcatatgcaa atcttttaac atagagaact    7705
gtcaccctga ggtaacaggg tcaactggcg aagcctgagc aggcagggc ttggctgccc    7765
cattccagct ctcccatgga gcccctccac cgggcgcatg cctcccaggc cacctcagtc    7825
tcacctgccg gctctgggct ggctgctcct aacctacctc gccgagctgt cggagggctg    7885
gacatttgtg gcagtgctga aggggcatt gccggcgagt aaagtattat gtttcttctt    7945
gtcaccccag ttcccttggt ggcaaccca gacccaaccc atgcccctga cagatctagt    8005
tctcttctcc tgtgttccct ttgagtccag tgtgggacac ggtttaactg tcccagcgac    8065
atttctccaa gtggaaatcc tattttttgta gatctccatg ctttgctctc aaggcttgga    8125
gaggtatgtg cccctcctgg gtgctcaccg cctgctacac aggcaggaat gcggttggga    8185
ggcaggtcgg gctgccagcc cagctggccg gaaggagact gtggttttttg tgtgtgtgga    8245
cagcccggga gctttgagac aggtgcctgg ggctggctgc agacggtgtg gttggggtg    8305
ggaggtgagc tagacccaac ccttagcttt tagcctggct gtcacctttt taatttccag    8365
aactgcacaa tgaccagcag gagggaagga cagacatcaa gtgccagatg ttgtctgaac    8425
taatcgagca cttctcacca aacttcatgt ataaataaaa tacatatttt taaaacaaac    8485
caataaatgg cttacatga                                                 8504
```

<210> SEQ ID NO 7
<211> LENGTH: 2016
<212> TYPE: PRT
<213> ORGANISM: Homo sapiens

<400> SEQUENCE: 7

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125
```

-continued

```
Val His Ser Leu Phe Asn Met Leu Ile Met Cys Thr Ile Leu Thr Asn
130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
                180                 185                 190

Trp Asn Trp Leu Asp Phe Ser Val Ile Met Ala Tyr Thr Thr Glu
                195                 200                 205

Phe Val Asp Leu Gly Asn Val Ser Ala Leu Arg Thr Phe Arg Val Leu
210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
                260                 265                 270

Met Gly Asn Leu Arg His Lys Cys Val Arg Asn Phe Thr Ala Leu Asn
                275                 280                 285

Gly Thr Asn Gly Ser Val Glu Ala Asp Gly Leu Val Trp Glu Ser Leu
290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
                340                 345                 350

Thr Ser Phe Asp Ser Phe Ala Trp Ala Phe Leu Ala Leu Phe Arg Leu
                355                 360                 365

Met Thr Gln Asp Cys Trp Glu Arg Leu Tyr Gln Gln Thr Leu Arg Ser
                370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
                420                 425                 430

Arg Phe Gln Glu Ala Met Glu Met Leu Lys Lys Glu His Glu Ala Leu
                435                 440                 445

Thr Ile Arg Gly Val Asp Thr Val Ser Arg Ser Ser Leu Glu Met Ser
450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
                500                 505                 510

Arg Gly Leu Ser Arg Thr Ser Met Lys Pro Arg Ser Ser Arg Gly Ser
                515                 520                 525

Ile Phe Thr Phe Arg Arg Arg Asp Leu Gly Ser Glu Ala Asp Phe Ala
                530                 535                 540

Asp Asp Glu Asn Ser Thr Ala Gly Glu Ser Glu Ser His His Thr Ser
545                 550                 555                 560
```

```
Leu Leu Val Pro Trp Pro Leu Arg Arg Thr Ser Ala Gln Gly Gln Pro
            565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
            595                 600                 605

Pro Glu Ala Thr Ser Pro Gly Ser His Leu Leu Arg Pro Val Met Leu
            610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
            645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
            675                 680                 685

Arg Leu Ala Gln Arg Tyr Leu Ile Trp Glu Cys Cys Pro Leu Trp Met
            690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
            725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
            770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
            805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
            835                 840                 845

Ile Val Phe Ile Phe Ala Val Val Gly Met Gln Leu Phe Gly Lys Asn
            850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
            885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
            915                 920                 925

Val Val Leu Asn Leu Phe Leu Ala Leu Leu Leu Ser Ser Phe Ser Ala
            930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
            965                 970                 975

Thr Trp Asp Phe Cys Cys Gly Leu Leu Arg Gln Arg Pro Gln Lys Pro
```

```
              980             985             990
Ala Ala Leu Ala Ala Gln Gly Gln  Leu Pro Ser Cys Ile  Ala Thr Pro
                995             1000            1005
Tyr Ser Pro Pro Pro Pro Glu Thr Glu Lys Val Pro  Pro Thr Arg
    1010            1015            1020
Lys Glu Thr Arg Phe Glu Glu Gly Gln Pro Gly  Gln Gly Thr
    1025            1030            1035
Pro Gly Asp Pro Glu Pro Val Cys Val Pro Ile Ala  Val Ala Glu
    1040            1045            1050
Ser Asp Thr Asp Asp Gln Glu Asp Glu Glu Asn  Ser Leu Gly
    1055            1060            1065
Thr Glu Glu Glu Ser Ser Lys Gln Gln Glu Ser Gln  Pro Val Ser
    1070            1075            1080
Gly Gly Pro Glu Ala Pro Pro Asp Ser Arg Thr Trp  Ser Gln Val
    1085            1090            1095
Ser Ala Thr Ala Ser Ser Glu Ala Glu Ala Ser Ala  Ser Gln Ala
    1100            1105            1110
Asp Trp Arg Gln Gln Trp Lys Ala Glu Pro Gln Ala  Pro Gly Cys
    1115            1120            1125
Gly Glu Thr Pro Glu Asp Ser Cys Ser Glu Gly Ser  Thr Ala Asp
    1130            1135            1140
Met Thr Asn Thr Ala Glu Leu Leu Glu Gln Ile Pro  Asp Leu Gly
    1145            1150            1155
Gln Asp Val Lys Asp Pro Glu Asp Cys Phe Thr Glu  Gly Cys Val
    1160            1165            1170
Arg Arg Cys Pro Cys Cys Ala Val Asp Thr Thr Gln  Ala Pro Gly
    1175            1180            1185
Lys Val Trp Trp Arg Leu Arg Lys Thr Cys Tyr His  Ile Val Glu
    1190            1195            1200
His Ser Trp Phe Glu Thr Phe Ile Ile Phe Met Ile  Leu Leu Ser
    1205            1210            1215
Ser Gly Ala Leu Ala Phe Glu Asp Ile Tyr Leu Glu  Glu Arg Lys
    1220            1225            1230
Thr Ile Lys Val Leu Leu Glu Tyr Ala Asp Lys Met  Phe Thr Tyr
    1235            1240            1245
Val Phe Val Leu Glu Met Leu Leu Lys Trp Val Ala  Tyr Gly Phe
    1250            1255            1260
Lys Lys Tyr Phe Thr Asn Ala Trp Cys Trp Leu Asp  Phe Leu Ile
    1265            1270            1275
Val Asp Val Ser Leu Val Ser Leu Val Ala Asn Thr  Leu Gly Phe
    1280            1285            1290
Ala Glu Met Gly Pro Ile Lys Ser Leu Arg Thr Leu  Arg Ala Leu
    1295            1300            1305
Arg Pro Leu Arg Ala Leu Ser Arg Phe Glu Gly Met  Arg Val Val
    1310            1315            1320
Val Asn Ala Leu Val Gly Ala Ile Pro Ser Ile Met  Asn Val Leu
    1325            1330            1335
Leu Val Cys Leu Ile Phe Trp Leu Ile Phe Ser Ile  Met Gly Val
    1340            1345            1350
Asn Leu Phe Ala Gly Lys Phe Gly Arg Cys Ile Asn  Gln Thr Glu
    1355            1360            1365
Gly Asp Leu Pro Leu Asn Tyr Thr Ile Val Asn Asn  Lys Ser Gln
    1370            1375            1380
```

```
Cys Glu Ser Leu Asn Leu Thr Gly Glu Leu Tyr Trp Thr Lys Val
    1385                1390                1395

Lys Val Asn Phe Asp Asn Val Gly Ala Gly Tyr Leu Ala Leu Leu
    1400                1405                1410

Gln Val Ala Thr Phe Lys Gly Trp Met Asp Ile Met Tyr Ala Ala
    1415                1420                1425

Val Asp Ser Arg Gly Tyr Glu Glu Pro Gln Trp Glu Tyr Asn
    1430                1435                1440

Leu Tyr Met Tyr Ile Tyr Phe Val Ile Phe Ile Phe Gly Ser
    1445                1450                1455

Phe Phe Thr Leu Asn Leu Phe Ile Gly Val Ile Ile Asp Asn Phe
    1460                1465                1470

Asn Gln Gln Lys Lys Lys Leu Gly Gly Gln Asp Ile Phe Met Thr
    1475                1480                1485

Glu Glu Gln Lys Lys Tyr Tyr Asn Ala Met Lys Lys Leu Gly Ser
    1490                1495                1500

Lys Lys Pro Gln Lys Pro Ile Pro Arg Pro Leu Asn Lys Tyr Gln
    1505                1510                1515

Gly Phe Ile Phe Asp Ile Val Thr Lys Gln Ala Phe Asp Val Thr
    1520                1525                1530

Ile Met Phe Leu Ile Cys Leu Asn Met Val Thr Met Met Val Glu
    1535                1540                1545

Thr Asp Asp Gln Ser Pro Glu Lys Ile Asn Ile Leu Ala Lys Ile
    1550                1555                1560

Asn Leu Leu Phe Val Ala Ile Phe Thr Gly Glu Cys Ile Val Lys
    1565                1570                1575

Leu Ala Ala Leu Arg His Tyr Tyr Phe Thr Asn Ser Trp Asn Ile
    1580                1585                1590

Phe Asp Phe Val Val Val Ile Leu Ser Ile Val Gly Thr Val Leu
    1595                1600                1605

Ser Asp Ile Ile Gln Lys Tyr Phe Phe Ser Pro Thr Leu Phe Arg
    1610                1615                1620

Val Ile Arg Leu Ala Arg Ile Gly Arg Ile Leu Arg Leu Ile Arg
    1625                1630                1635

Gly Ala Lys Gly Ile Arg Thr Leu Leu Phe Ala Leu Met Met Ser
    1640                1645                1650

Leu Pro Ala Leu Phe Asn Ile Gly Leu Leu Leu Phe Leu Val Met
    1655                1660                1665

Phe Ile Tyr Ser Ile Phe Gly Met Ala Asn Phe Ala Tyr Val Lys
    1670                1675                1680

Trp Glu Ala Gly Ile Asp Asp Met Phe Asn Phe Gln Thr Phe Ala
    1685                1690                1695

Asn Ser Met Leu Cys Leu Phe Gln Ile Thr Thr Ser Ala Gly Trp
    1700                1705                1710

Asp Gly Leu Leu Ser Pro Ile Leu Asn Thr Gly Pro Pro Tyr Cys
    1715                1720                1725

Asp Pro Thr Leu Pro Asn Ser Asn Gly Ser Arg Gly Asp Cys Gly
    1730                1735                1740

Ser Pro Ala Val Gly Ile Leu Phe Phe Thr Thr Tyr Ile Ile Ile
    1745                1750                1755

Ser Phe Leu Ile Val Val Asn Met Tyr Ile Ala Ile Ile Leu Glu
    1760                1765                1770

Asn Phe Ser Val Ala Thr Glu Glu Ser Thr Glu Pro Leu Ser Glu
    1775                1780                1785
```

-continued

```
Asp Asp Phe Asp Met Phe Tyr Glu Ile Trp Glu Lys Phe Asp Pro
    1790            1795                1800

Glu Ala Thr Gln Phe Ile Glu Tyr Ser Val Leu Ser Asp Phe Ala
    1805            1810                1815

Asp Ala Leu Ser Glu Pro Leu Arg Ile Ala Lys Pro Asn Gln Ile
    1820            1825                1830

Ser Leu Ile Asn Met Asp Leu Pro Met Val Ser Gly Asp Arg Ile
    1835            1840                1845

His Cys Met Asp Ile Leu Phe Ala Phe Thr Lys Arg Val Leu Gly
    1850            1855                1860

Glu Ser Gly Glu Met Asp Ala Leu Lys Ile Gln Met Glu Glu Lys
    1865            1870                1875

Phe Met Ala Ala Asn Pro Ser Lys Ile Ser Tyr Glu Pro Ile Thr
    1880            1885                1890

Thr Thr Leu Arg Arg Lys His Glu Glu Val Ser Ala Met Val Ile
    1895            1900                1905

Gln Arg Ala Phe Arg Arg His Leu Leu Gln Arg Ser Leu Lys His
    1910            1915                1920

Ala Ser Phe Leu Phe Arg Gln Gln Ala Gly Ser Gly Leu Ser Glu
    1925            1930                1935

Glu Asp Ala Pro Glu Arg Glu Gly Leu Ile Ala Tyr Val Met Ser
    1940            1945                1950

Glu Asn Phe Ser Arg Pro Leu Gly Pro Pro Ser Ser Ser Ser Ile
    1955            1960                1965

Ser Ser Thr Ser Phe Pro Pro Ser Tyr Asp Ser Val Thr Arg Ala
    1970            1975                1980

Thr Ser Asp Asn Leu Gln Val Arg Gly Ser Asp Tyr Ser His Ser
    1985            1990                1995

Glu Asp Leu Ala Asp Phe Pro Pro Ser Pro Asp Arg Asp Arg Glu
    2000            2005                2010

Ser Ile Val
    2015

<210> SEQ ID NO 8
<211> LENGTH: 8501
<212> TYPE: DNA
<213> ORGANISM: Homo sapiens
<220> FEATURE:
<221> NAME/KEY: CDS
<222> LOCATION: (195)..(6242)

<400> SEQUENCE: 8
agacggcggc ggcgcccgta ggatgcaggg atcgctcccc cggggccgct gagcctgcgc      60
ccagtgcccc gagccccgcg ccgagccgag tccgcgccaa gcagcagccg cccaccccgg     120
ggcccggccg ggggaccagc agcttcccca caggcaacgt gaggagagcc tgtgcccaga     180
agcaggatga gaag atg gca aac ttc cta tta cct cgg ggc acc agc agc      230
              Met Ala Asn Phe Leu Leu Pro Arg Gly Thr Ser Ser
                1               5                  10 ttc cgc agg ttc aca cgg gag tcc ctg gca gcc atc gag aag cgc atg      278
Phe Arg Arg Phe Thr Arg Glu Ser Leu Ala Ala Ile Glu Lys Arg Met
        15                  20                  25 gca gag aag caa gcc cgc ggc tca acc acc ttg cag gag agc cga gag      326
Ala Glu Lys Gln Ala Arg Gly Ser Thr Thr Leu Gln Glu Ser Arg Glu
    30                  35                  40 ggg ctg ccc gag gag gag gct ccc cgg ccc cag ctg gac ctg cag gcc      374
Gly Leu Pro Glu Glu Glu Ala Pro Arg Pro Gln Leu Asp Leu Gln Ala
```

-continued

```
        45                  50                   55                 60
tcc aaa aag ctg cca gat ctc tat ggc aat cca ccc caa gag ctc atc        422
Ser Lys Lys Leu Pro Asp Leu Tyr Gly Asn Pro Pro Gln Glu Leu Ile
                65                   70                  75 gga gag ccc ctg gag gac ctg gac ccc ttc tat agc acc caa aag act        470
Gly Glu Pro Leu Glu Asp Leu Asp Pro Phe Tyr Ser Thr Gln Lys Thr
                     80                  85                  90 ttc atc gta ctg aat aaa ggc aag acc atc ttc cgg ttc agt gcc acc        518
Phe Ile Val Leu Asn Lys Gly Lys Thr Ile Phe Arg Phe Ser Ala Thr
                95                  100                 105 aac gcc ttg tat gtc ctc agt ccc ttc cac ccc atc cgg aga gcg gct        566
Asn Ala Leu Tyr Val Leu Ser Pro Phe His Pro Ile Arg Arg Ala Ala
        110                 115                 120 gtg aag att ctg gtt cac tcg ctc ttc aac atg ctc atc atg tgc acc        614
Val Lys Ile Leu Val His Ser Leu Phe Asn Met Leu Ile Met Cys Thr
125                 130                 135                 140 atc ctc acc aac tgc gtg ttc atg gcc cag cac gac cct cca ccc tgg        662
Ile Leu Thr Asn Cys Val Phe Met Ala Gln His Asp Pro Pro Pro Trp
                145                 150                 155 acc aag tat gtc gag tac acc ttc acc gcc att tac acc ttt gag tct        710
Thr Lys Tyr Val Glu Tyr Thr Phe Thr Ala Ile Tyr Thr Phe Glu Ser
                160                 165                 170 ctg gtc aag att ctg gct cga ggc ttc tgc ctg cac gcg ttc act ttc        758
Leu Val Lys Ile Leu Ala Arg Gly Phe Cys Leu His Ala Phe Thr Phe
        175                 180                 185 ctt cgg gac cca tgg aac tgg ctg gac ttt agt gtg att atc atg gca        806
Leu Arg Asp Pro Trp Asn Trp Leu Asp Phe Ser Val Ile Ile Met Ala
        190                 195                 200 tac aca act gaa ttt gtg gac ctg ggc aat gtc tca gcc tta cgc acc        854
Tyr Thr Thr Glu Phe Val Asp Leu Gly Asn Val Ser Ala Leu Arg Thr
205                 210                 215                 220 ttc cga gtc ctc cgg gcc ctg aaa act ata tca gtc att tca ggg ctg        902
Phe Arg Val Leu Arg Ala Leu Lys Thr Ile Ser Val Ile Ser Gly Leu
                225                 230                 235 aag acc atc gtg ggg gcc ctg atc cag tct gtg aag aag ctg gct gat        950
Lys Thr Ile Val Gly Ala Leu Ile Gln Ser Val Lys Lys Leu Ala Asp
                240                 245                 250 gtg atg gtc ctc aca gtc ttc tgc ctc agc gtc ttt gcc ctc atc ggc        998
Val Met Val Leu Thr Val Phe Cys Leu Ser Val Phe Ala Leu Ile Gly
        255                 260                 265 ctg cag ctc ttc atg ggc aac cta agg cac aag tgc gtg cgc aac ttc       1046
Leu Gln Leu Phe Met Gly Asn Leu Arg His Lys Cys Val Arg Asn Phe
        270                 275                 280 aca gcg ctc aac ggc acc aac ggc tcc gtg gag gcc gac ggc ttg gtc       1094
Thr Ala Leu Asn Gly Thr Asn Gly Ser Val Glu Ala Asp Gly Leu Val
285                 290                 295                 300 tgg gaa tcc ctg gac ctt tac ctc agt gat cca gaa aat tac ctg ctc       1142
Trp Glu Ser Leu Asp Leu Tyr Leu Ser Asp Pro Glu Asn Tyr Leu Leu
                305                 310                 315 aag aac ggc acc tct gat gtg tta ctg tgt ggg aac agc tct gac gct       1190
Lys Asn Gly Thr Ser Asp Val Leu Leu Cys Gly Asn Ser Ser Asp Ala
                320                 325                 330 ggg aca tgt ccg gag ggc tac cgg tgc cta aag gca ggc gag aac ccc       1238
Gly Thr Cys Pro Glu Gly Tyr Arg Cys Leu Lys Ala Gly Glu Asn Pro
        335                 340                 345 gac cac ggc tac acc agc ttc gat tcc ttt gcc tgg gcc ttt ctt gca       1286
Asp His Gly Tyr Thr Ser Phe Asp Ser Phe Ala Trp Ala Phe Leu Ala
350                 355                 360 ctc ttc cgc ctg atg acg cag gac tgc tgg gag cgc ctc tat cag cag       1334
Leu Phe Arg Leu Met Thr Gln Asp Cys Trp Glu Arg Leu Tyr Gln Gln
```

```
                365                 370                 375                 380
acc ctc agg tcc gca ggg aag atc tac atg atc ttc ttc atg ctt gtc          1382
Thr Leu Arg Ser Ala Gly Lys Ile Tyr Met Ile Phe Phe Met Leu Val
                    385                 390                 395 atc ttc ctg ggg tcc ttc tac ctg gtg aac ctg atc ctg gcc gtg gtc          1430
Ile Phe Leu Gly Ser Phe Tyr Leu Val Asn Leu Ile Leu Ala Val Val
            400                 405                 410 gca atg gcc tat gag gag caa aac caa gcc acc atc gct gag acc gag          1478
Ala Met Ala Tyr Glu Glu Gln Asn Gln Ala Thr Ile Ala Glu Thr Glu
        415                 420                 425 gag aag gaa aag cgc ttc cag gag gcc atg gaa atg ctc aag aaa gaa          1526
Glu Lys Glu Lys Arg Phe Gln Glu Ala Met Glu Met Leu Lys Lys Glu
    430                 435                 440 cac gag gcc ctc acc atc agg ggt gtg gat acc gtg tcc cgt agc tcc          1574
His Glu Ala Leu Thr Ile Arg Gly Val Asp Thr Val Ser Arg Ser Ser
445                 450                 455                 460 ttg gag atg tcc cct ttg gcc cca gta aac agc cat gag aga aga agc          1622
Leu Glu Met Ser Pro Leu Ala Pro Val Asn Ser His Glu Arg Arg Ser
                465                 470                 475 aag agg aga aaa cgg atg tct tca gga act gag gag tgt ggg gag gac          1670
Lys Arg Arg Lys Arg Met Ser Ser Gly Thr Glu Glu Cys Gly Glu Asp
            480                 485                 490 agg ctc ccc aag tct gac tca gaa gat ggt ccc aga gca atg aat cat          1718
Arg Leu Pro Lys Ser Asp Ser Glu Asp Gly Pro Arg Ala Met Asn His
        495                 500                 505 ctc agc ctc acc cgt ggc ctc agc agg act tct atg aag cca cgt tcc          1766
Leu Ser Leu Thr Arg Gly Leu Ser Arg Thr Ser Met Lys Pro Arg Ser
    510                 515                 520 agc cgc ggg agc att ttc acc ttt cgc agg cga gac ctg ggt tct gaa          1814
Ser Arg Gly Ser Ile Phe Thr Phe Arg Arg Arg Asp Leu Gly Ser Glu
525                 530                 535                 540 gca gat ttt gca gat gat gaa aac agc aca gcg ggg gag agc gag agc          1862
Ala Asp Phe Ala Asp Asp Glu Asn Ser Thr Ala Gly Glu Ser Glu Ser
                545                 550                 555 cac cac aca tca ctg ctg gtg ccc tgg ccc ctg cgc cgg acc agt gcc          1910
His His Thr Ser Leu Leu Val Pro Trp Pro Leu Arg Arg Thr Ser Ala
            560                 565                 570 cag gga cag ccc agt ccc gga acc tcg gct cct ggc cac gcc ctc cat          1958
Gln Gly Gln Pro Ser Pro Gly Thr Ser Ala Pro Gly His Ala Leu His
        575                 580                 585 ggc aaa aag aac agc act gtg gac tgc aat ggg gtg gtc tca tta ctg          2006
Gly Lys Lys Asn Ser Thr Val Asp Cys Asn Gly Val Val Ser Leu Leu
    590                 595                 600 ggg gca ggc gac cca gag gcc aca tcc cca gga agc cac ctc ctc cgc          2054
Gly Ala Gly Asp Pro Glu Ala Thr Ser Pro Gly Ser His Leu Leu Arg
605                 610                 615                 620 cct gtg atg cta gag cac ccg cca gac acg acc acg cca tcg gag gag          2102
Pro Val Met Leu Glu His Pro Pro Asp Thr Thr Thr Pro Ser Glu Glu
                625                 630                 635 cca ggc ggg ccc cag atg ctg acc tcc cag gct ccg tgt gta gat ggc          2150
Pro Gly Gly Pro Gln Met Leu Thr Ser Gln Ala Pro Cys Val Asp Gly
            640                 645                 650 ttc gag gag cca gga gca cgg cag cgg gcc ctc agc gca gtc agc gtc          2198
Phe Glu Glu Pro Gly Ala Arg Gln Arg Ala Leu Ser Ala Val Ser Val
        655                 660                 665 ctc acc agc gca ctg gaa gag tta gag gag tct cgc cac aag tgt cca          2246
Leu Thr Ser Ala Leu Glu Glu Leu Glu Glu Ser Arg His Lys Cys Pro
    670                 675                 680 cca tgc tgg aac cgt ctc gcc cag cgc tac ctg atc tgg gag tgc tgc          2294
Pro Cys Trp Asn Arg Leu Ala Gln Arg Tyr Leu Ile Trp Glu Cys Cys
```

```
                685                 690                 695                 700
ccg  ctg  tgg  atg  tcc  atc  aag  cag  gga  gtg  aag  ttg  gtg  gtc  atg  gac        2342
Pro  Leu  Trp  Met  Ser  Ile  Lys  Gln  Gly  Val  Lys  Leu  Val  Val  Met  Asp
                    705                 710                 715 ccg  ttt  act  gac  ctc  acc  atc  act  atg  tgc  atc  gta  ctc  aac  aca  ctc        2390
Pro  Phe  Thr  Asp  Leu  Thr  Ile  Thr  Met  Cys  Ile  Val  Leu  Asn  Thr  Leu
          720                 725                 730 ttc  atg  gcg  ctg  gag  cac  tac  aac  atg  aca  agt  gaa  ttc  gag  gag  atg        2438
Phe  Met  Ala  Leu  Glu  His  Tyr  Asn  Met  Thr  Ser  Glu  Phe  Glu  Glu  Met
               735                 740                 745 ctg  cag  gtc  gga  aac  ctg  gtc  ttc  aca  ggg  att  ttc  aca  gca  gag  atg        2486
Leu  Gln  Val  Gly  Asn  Leu  Val  Phe  Thr  Gly  Ile  Phe  Thr  Ala  Glu  Met
          750                 755                 760 acc  ttc  aag  atc  att  gcc  ctc  gac  ccc  tac  tac  tac  ttc  caa  cag  ggc        2534
Thr  Phe  Lys  Ile  Ile  Ala  Leu  Asp  Pro  Tyr  Tyr  Tyr  Phe  Gln  Gln  Gly
765                 770                 775                 780 tgg  aac  atc  ttc  gac  agc  atc  atc  gtc  atc  ctt  agc  ctc  atg  gag  ctg        2582
Trp  Asn  Ile  Phe  Asp  Ser  Ile  Ile  Val  Ile  Leu  Ser  Leu  Met  Glu  Leu
               785                 790                 795 ggc  ctg  tcc  cgc  atg  agc  aac  ttg  tcg  gtg  ctg  cgc  tcc  ttc  cgc  ctg        2630
Gly  Leu  Ser  Arg  Met  Ser  Asn  Leu  Ser  Val  Leu  Arg  Ser  Phe  Arg  Leu
          800                 805                 810 ctg  cgg  gtc  ttc  aag  ctg  gcc  aaa  tca  tgg  ccc  acc  ctg  aac  aca  ctc        2678
Leu  Arg  Val  Phe  Lys  Leu  Ala  Lys  Ser  Trp  Pro  Thr  Leu  Asn  Thr  Leu
          815                 820                 825 atc  aag  atc  atc  ggg  aac  tca  gtg  ggg  gca  ctg  ggg  aac  ctg  aca  ctc        2726
Ile  Lys  Ile  Ile  Gly  Asn  Ser  Val  Gly  Ala  Leu  Gly  Asn  Leu  Thr  Leu
     830                 835                 840 gtg  cta  gcc  atc  atc  gtg  ttc  atc  ttt  gct  gtg  gtg  ggc  atg  cag  ctc        2774
Val  Leu  Ala  Ile  Ile  Val  Phe  Ile  Phe  Ala  Val  Val  Gly  Met  Gln  Leu
845                 850                 855                 860 ttt  ggc  aag  aac  tac  tcg  gag  ctg  agg  gac  agc  gac  tca  ggc  ctg  ctg        2822
Phe  Gly  Lys  Asn  Tyr  Ser  Glu  Leu  Arg  Asp  Ser  Asp  Ser  Gly  Leu  Leu
               865                 870                 875 cct  cgc  tgg  cac  atg  atg  gac  ttc  ttt  cat  gcc  ttc  ctc  atc  atc  ttc        2870
Pro  Arg  Trp  His  Met  Met  Asp  Phe  Phe  His  Ala  Phe  Leu  Ile  Ile  Phe
          880                 885                 890 cgc  atc  ctc  tgt  gga  gag  tgg  atc  gag  acc  atg  tgg  gac  tgc  atg  gag        2918
Arg  Ile  Leu  Cys  Gly  Glu  Trp  Ile  Glu  Thr  Met  Trp  Asp  Cys  Met  Glu
     895                 900                 905 gtg  tcg  ggg  cag  tca  tta  tgc  ctg  ctg  gtc  ttc  ttg  ctt  gtt  atg  gtc        2966
Val  Ser  Gly  Gln  Ser  Leu  Cys  Leu  Leu  Val  Phe  Leu  Leu  Val  Met  Val
910                 915                 920 att  ggc  aac  ctt  gtg  gtc  ctg  aat  ctc  ttc  ctg  gcc  ttg  ctg  ctc  agc        3014
Ile  Gly  Asn  Leu  Val  Val  Leu  Asn  Leu  Phe  Leu  Ala  Leu  Leu  Leu  Ser
925                 930                 935                 940 tcc  ttc  agt  gca  gac  aac  ctc  aca  gcc  cct  gat  gag  gac  aga  gag  atg        3062
Ser  Phe  Ser  Ala  Asp  Asn  Leu  Thr  Ala  Pro  Asp  Glu  Asp  Arg  Glu  Met
               945                 950                 955 aac  aac  ctc  cag  ctg  gcc  ctg  gcc  cgc  atc  cag  agg  ggc  ctg  cgc  ttt        3110
Asn  Asn  Leu  Gln  Leu  Ala  Leu  Ala  Arg  Ile  Gln  Arg  Gly  Leu  Arg  Phe
          960                 965                 970 gtc  aag  cgg  acc  acc  tgg  gat  ttc  tgc  tgt  ggt  ctc  ctg  cgg  cag  cgg        3158
Val  Lys  Arg  Thr  Thr  Trp  Asp  Phe  Cys  Cys  Gly  Leu  Leu  Arg  Gln  Arg
          975                 980                 985 cct  cag  aag  ccc  gca  gcc  ctt  gcc  gcc  cag  ggc  cag    ctg  ccc  agc  tgc      3206
Pro  Gln  Lys  Pro  Ala  Ala  Leu  Ala  Ala  Gln  Gly  Gln    Leu  Pro  Ser  Cys
          990                 995                      1000 att  gcc  acc  ccc  tac  tcc    ccg  cca  ccc  cca  gag     acg  gag  aag  gtg        3251
Ile  Ala  Thr  Pro  Tyr  Ser    Pro  Pro  Pro  Pro  Glu     Thr  Glu  Lys  Val
```

| | | | | | | | | | | | | | |
|---|---|---|---|---|---|---|---|---|---|---|---|---|---|
| | | 1005 | | | | 1010 | | | | | 1015 | | |
| cct | ccc | acc | cgc | aag | gaa | aca | cgg | ttt | gag | gaa | ggc | gag | caa | cca | 3296 |
| Pro | Pro | Thr | Arg | Lys | Glu | Thr | Arg | Phe | Glu | Glu | Gly | Glu | Gln | Pro |
| 1020 | | | | | 1025 | | | | | 1030 | | | | |
| ggc | cag | ggc | acc | ccc | ggg | gat | cca | gag | ccc | gtg | tgt | gtg | ccc | atc | 3341 |
| Gly | Gln | Gly | Thr | Pro | Gly | Asp | Pro | Glu | Pro | Val | Cys | Val | Pro | Ile |
| 1035 | | | | | 1040 | | | | | 1045 | | | | |
| gct | gtg | gcc | gag | tca | gac | aca | gat | gac | caa | gaa | gaa | gat | gag | gag | 3386 |
| Ala | Val | Ala | Glu | Ser | Asp | Thr | Asp | Asp | Gln | Glu | Glu | Asp | Glu | Glu |
| 1050 | | | | | 1055 | | | | | 1060 | | | | |
| aac | agc | ctg | ggc | acg | gag | gag | gag | tcc | agc | aag | cag | gaa | tcc | cag | 3431 |
| Asn | Ser | Leu | Gly | Thr | Glu | Glu | Glu | Ser | Ser | Lys | Gln | Glu | Ser | Gln |
| 1065 | | | | | 1070 | | | | | 1075 | | | | |
| cct | gtg | tcc | ggt | ggc | cca | gag | gcc | cct | ccg | gat | tcc | agg | acc | tgg | 3476 |
| Pro | Val | Ser | Gly | Gly | Pro | Glu | Ala | Pro | Pro | Asp | Ser | Arg | Thr | Trp |
| 1080 | | | | | 1085 | | | | | 1090 | | | | |
| agc | cag | gtg | tca | gcg | act | gcc | tcc | tct | gag | gcc | gag | gcc | agt | gca | 3521 |
| Ser | Gln | Val | Ser | Ala | Thr | Ala | Ser | Ser | Glu | Ala | Glu | Ala | Ser | Ala |
| 1095 | | | | | 1100 | | | | | 1105 | | | | |
| tct | cag | gcc | gac | tgg | cgg | cag | cag | tgg | aaa | gcg | gaa | ccc | cag | gcc | 3566 |
| Ser | Gln | Ala | Asp | Trp | Arg | Gln | Gln | Trp | Lys | Ala | Glu | Pro | Gln | Ala |
| 1110 | | | | | 1115 | | | | | 1120 | | | | |
| cca | ggg | tgc | ggt | gag | acc | cca | gag | gac | agt | tgc | tcc | gag | ggc | agc | 3611 |
| Pro | Gly | Cys | Gly | Glu | Thr | Pro | Glu | Asp | Ser | Cys | Ser | Glu | Gly | Ser |
| 1125 | | | | | 1130 | | | | | 1135 | | | | |
| aca | gca | gac | atg | acc | aac | acc | gct | gag | ctc | ctg | gag | cag | atc | cct | 3656 |
| Thr | Ala | Asp | Met | Thr | Asn | Thr | Ala | Glu | Leu | Leu | Glu | Gln | Ile | Pro |
| 1140 | | | | | 1145 | | | | | 1150 | | | | |
| gac | ctc | ggc | cag | gat | gtc | aag | gac | cca | gag | gac | tgc | ttc | act | gaa | 3701 |
| Asp | Leu | Gly | Gln | Asp | Val | Lys | Asp | Pro | Glu | Asp | Cys | Phe | Thr | Glu |
| 1155 | | | | | 1160 | | | | | 1165 | | | | |
| ggc | tgt | gtc | cgg | cgc | tgt | ccc | tgc | tgt | gcg | gtg | gac | acc | aca | cag | 3746 |
| Gly | Cys | Val | Arg | Arg | Cys | Pro | Cys | Cys | Ala | Val | Asp | Thr | Thr | Gln |
| 1170 | | | | | 1175 | | | | | 1180 | | | | |
| gcc | cca | ggg | aag | gtc | tgg | tgg | cgg | ttg | cgc | aag | acc | tgc | tac | cac | 3791 |
| Ala | Pro | Gly | Lys | Val | Trp | Trp | Arg | Leu | Arg | Lys | Thr | Cys | Tyr | His |
| 1185 | | | | | 1190 | | | | | 1195 | | | | |
| atc | gtg | gag | cac | agc | tgg | ttc | gag | aca | ttc | atc | atc | ttc | atg | atc | 3836 |
| Ile | Val | Glu | His | Ser | Trp | Phe | Glu | Thr | Phe | Ile | Ile | Phe | Met | Ile |
| 1200 | | | | | 1205 | | | | | 1210 | | | | |
| cta | ctc | agc | agt | gga | gcg | ctg | gcc | ttc | gag | gac | atc | tac | cta | gag | 3881 |
| Leu | Leu | Ser | Ser | Gly | Ala | Leu | Ala | Phe | Glu | Asp | Ile | Tyr | Leu | Glu |
| 1215 | | | | | 1220 | | | | | 1225 | | | | |
| gag | cgg | aag | acc | atc | aag | gtt | ctg | ctt | gag | tat | gcc | gac | aag | atg | 3926 |
| Glu | Arg | Lys | Thr | Ile | Lys | Val | Leu | Leu | Glu | Tyr | Ala | Asp | Lys | Met |
| 1230 | | | | | 1235 | | | | | 1240 | | | | |
| ttc | aca | tat | gtc | ttc | gtg | ctg | gag | atg | ctg | ctc | aag | tgg | gtg | gcc | 3971 |
| Phe | Thr | Tyr | Val | Phe | Val | Leu | Glu | Met | Leu | Leu | Lys | Trp | Val | Ala |
| 1245 | | | | | 1250 | | | | | 1255 | | | | |
| tac | ggc | ttc | aag | aag | tac | ttc | acc | aat | gcc | tgg | tgc | tgg | ctc | gac | 4016 |
| Tyr | Gly | Phe | Lys | Lys | Tyr | Phe | Thr | Asn | Ala | Trp | Cys | Trp | Leu | Asp |
| 1260 | | | | | 1265 | | | | | 1270 | | | | |
| ttc | ctc | atc | gta | gac | gtc | tct | ctg | gtc | agc | ctg | gtg | gcc | aac | acc | 4061 |
| Phe | Leu | Ile | Val | Asp | Val | Ser | Leu | Val | Ser | Leu | Val | Ala | Asn | Thr |
| 1275 | | | | | 1280 | | | | | 1285 | | | | |
| ctg | ggc | ttt | gcc | gag | atg | ggc | ccc | atc | aag | tca | ctg | cgg | acg | ctg | 4106 |
| Leu | Gly | Phe | Ala | Glu | Met | Gly | Pro | Ile | Lys | Ser | Leu | Arg | Thr | Leu |
| 1290 | | | | | 1295 | | | | | 1300 | | | | |
| cgt | gca | ctc | cgt | cct | ctg | aga | gct | ctg | tca | cga | ttt | gag | ggc | atg | 4151 |
| Arg | Ala | Leu | Arg | Pro | Leu | Arg | Ala | Leu | Ser | Arg | Phe | Glu | Gly | Met |

```
                                        -continued
  1305                1310                1315
agg gtg gtg gtc aat gcc ctg gtg ggc gcc atc ccg tcc atc atg    4196
Arg Val Val Val Asn Ala Leu Val Gly Ala Ile Pro Ser Ile Met
1320                1325                1330 aac gtc ctc ctc gtc tgc ctc atc ttc tgg ctc atc ttc agc atc    4241
Asn Val Leu Leu Val Cys Leu Ile Phe Trp Leu Ile Phe Ser Ile
1335                1340                1345 atg ggc gtg aac ctc ttt gcg ggg aag ttt ggg agg tgc atc aac    4286
Met Gly Val Asn Leu Phe Ala Gly Lys Phe Gly Arg Cys Ile Asn
1350                1355                1360 cag aca gag gga gac ttg cct ttg aac tac acc atc gtg aac aac    4331
Gln Thr Glu Gly Asp Leu Pro Leu Asn Tyr Thr Ile Val Asn Asn
1365                1370                1375 aag agc cag tgt gag tcc ttg aac ttg acc gga gaa ttg tac tgg    4376
Lys Ser Gln Cys Glu Ser Leu Asn Leu Thr Gly Glu Leu Tyr Trp
1380                1385                1390 acc aag gtg aaa gtc aac ttt gac aac gtg ggg gcc ggg tac ctg    4421
Thr Lys Val Lys Val Asn Phe Asp Asn Val Gly Ala Gly Tyr Leu
1395                1400                1405 gcc ctt ctg cag gtg gca aca ttt aaa ggc tgg atg gac att atg    4466
Ala Leu Leu Gln Val Ala Thr Phe Lys Gly Trp Met Asp Ile Met
1410                1415                1420 tat gca gct gtg gac tcc agg ggg tat gaa gag cag cct cag tgg    4511
Tyr Ala Ala Val Asp Ser Arg Gly Tyr Glu Glu Gln Pro Gln Trp
1425                1430                1435 gaa tac aac ctc tac atg tac atc tat ttt gtc att ttc atc atc    4556
Glu Tyr Asn Leu Tyr Met Tyr Ile Tyr Phe Val Ile Phe Ile Ile
1440                1445                1450 ttt ggg tct ttc ttc acc ctg aac ctc ttt att ggt gtc atc att    4601
Phe Gly Ser Phe Phe Thr Leu Asn Leu Phe Ile Gly Val Ile Ile
1455                1460                1465 gac aac ttc aac caa cag aag aaa aag tta ggg ggc cag gac atc    4646
Asp Asn Phe Asn Gln Gln Lys Lys Lys Leu Gly Gly Gln Asp Ile
1470                1475                1480 ttc atg aca gag gag cag aag aag tac tac aat gcc atg aag aag    4691
Phe Met Thr Glu Glu Gln Lys Lys Tyr Tyr Asn Ala Met Lys Lys
1485                1490                1495 ctg ggc tcc aag aag ccc cag aag ccc atc cca cgg ccc ctg aac    4736
Leu Gly Ser Lys Lys Pro Gln Lys Pro Ile Pro Arg Pro Leu Asn
1500                1505                1510 aag tac cag ggc ttc ata ttc gac att gtg acc aag cag gcc ttt    4781
Lys Tyr Gln Gly Phe Ile Phe Asp Ile Val Thr Lys Gln Ala Phe
1515                1520                1525 gac gtc acc atc atg ttt ctg atc tgc ttg aat atg gtg acc atg    4826
Asp Val Thr Ile Met Phe Leu Ile Cys Leu Asn Met Val Thr Met
1530                1535                1540 atg gtg gag aca gat gac caa agt cct gag aaa atc aac atc ttg    4871
Met Val Glu Thr Asp Asp Gln Ser Pro Glu Lys Ile Asn Ile Leu
1545                1550                1555 gcc aag atc aac ctg ctc ttt gtg gcc atc ttc aca ggc gag tgt    4916
Ala Lys Ile Asn Leu Leu Phe Val Ala Ile Phe Thr Gly Glu Cys
1560                1565                1570 att gtc aag ctg gct gcc ctg cgc cac tac tac ttc acc aac agc    4961
Ile Val Lys Leu Ala Ala Leu Arg His Tyr Tyr Phe Thr Asn Ser
1575                1580                1585 tgg aat atc ttc gac ttc gtg gtt gtc atc ctc tcc atc gtg ggc    5006
Trp Asn Ile Phe Asp Phe Val Val Val Ile Leu Ser Ile Val Gly
1590                1595                1600 act gtg ctc tcg gac atc atc cag aag tac ttc ttc tcc ccg acg    5051
Thr Val Leu Ser Asp Ile Ile Gln Lys Tyr Phe Phe Ser Pro Thr
```

-continued

| | | | | | | | | | | |
|---|---|---|---|---|---|---|---|---|---|---|
| | | | 1605 | | | 1610 | | | 1615 | |
| ctc | ttc | cga | gtc | atc | cgc | ctg | gcc | cga | ata | ggc | cgc | atc | ctc | aga | 5096 |
| Leu | Phe | Arg | Val | Ile | Arg | Leu | Ala | Arg | Ile | Gly | Arg | Ile | Leu | Arg | |
| 1620 | | | | 1625 | | | | 1630 | | | |
| ctg | atc | cga | ggg | gcc | aag | ggg | atc | cgc | acg | ctc | ctc | ttt | gcc | ctc | 5141 |
| Leu | Ile | Arg | Gly | Ala | Lys | Gly | Ile | Arg | Thr | Leu | Leu | Phe | Ala | Leu | |
| 1635 | | | | 1640 | | | | 1645 | | | |
| atg | atg | tcc | ctg | cct | gcc | ctc | ttc | aac | atc | ggg | ctg | ctc | ctc | ttc | 5186 |
| Met | Met | Ser | Leu | Pro | Ala | Leu | Phe | Asn | Ile | Gly | Leu | Leu | Leu | Phe | |
| 1650 | | | | 1655 | | | | 1660 | | | |
| ctc | gtc | atg | ttc | atc | tac | tcc | atc | ttt | ggc | atg | gcc | aac | ttc | gct | 5231 |
| Leu | Val | Met | Phe | Ile | Tyr | Ser | Ile | Phe | Gly | Met | Ala | Asn | Phe | Ala | |
| 1665 | | | | 1670 | | | | 1675 | | | |
| tat | gtc | aag | tgg | gag | gct | ggc | atc | gac | gac | atg | ttc | aac | ttc | cag | 5276 |
| Tyr | Val | Lys | Trp | Glu | Ala | Gly | Ile | Asp | Asp | Met | Phe | Asn | Phe | Gln | |
| 1680 | | | | 1685 | | | | 1690 | | | |
| acc | ttc | gcc | aac | agc | atg | ctg | tgc | ctc | ttc | cag | atc | acc | acg | tcg | 5321 |
| Thr | Phe | Ala | Asn | Ser | Met | Leu | Cys | Leu | Phe | Gln | Ile | Thr | Thr | Ser | |
| 1695 | | | | 1700 | | | | 1705 | | | |
| gcc | ggc | tgg | gat | ggc | ctc | ctc | agc | ccc | atc | ctc | aac | act | ggg | ccg | 5366 |
| Ala | Gly | Trp | Asp | Gly | Leu | Leu | Ser | Pro | Ile | Leu | Asn | Thr | Gly | Pro | |
| 1710 | | | | 1715 | | | | 1720 | | | |
| ccc | tac | tgc | gac | ccc | act | ctg | ccc | aac | agc | aat | ggc | tct | cgg | ggc | 5411 |
| Pro | Tyr | Cys | Asp | Pro | Thr | Leu | Pro | Asn | Ser | Asn | Gly | Ser | Arg | Gly | |
| 1725 | | | | 1730 | | | | 1735 | | | |
| gac | tgc | ggg | agc | cca | gcc | gtg | ggc | atc | ctc | ttc | ttc | acc | acc | tac | 5456 |
| Asp | Cys | Gly | Ser | Pro | Ala | Val | Gly | Ile | Leu | Phe | Phe | Thr | Thr | Tyr | |
| 1740 | | | | 1745 | | | | 1750 | | | |
| atc | atc | atc | tcc | ttc | ctc | atc | gtg | gtc | aac | atg | tac | att | gcc | atc | 5501 |
| Ile | Ile | Ile | Ser | Phe | Leu | Ile | Val | Val | Asn | Met | Tyr | Ile | Ala | Ile | |
| 1755 | | | | 1760 | | | | 1765 | | | |
| atc | ctg | gag | aac | ttc | agc | gtg | gcc | acg | gag | gag | agc | acc | gag | ccc | 5546 |
| Ile | Leu | Glu | Asn | Phe | Ser | Val | Ala | Thr | Glu | Glu | Ser | Thr | Glu | Pro | |
| 1770 | | | | 1775 | | | | 1780 | | | |
| ctg | agt | gag | gac | gac | ttc | gat | atg | ttc | tat | gag | atc | tgg | gag | aaa | 5591 |
| Leu | Ser | Glu | Asp | Asp | Phe | Asp | Met | Phe | Tyr | Glu | Ile | Trp | Glu | Lys | |
| 1785 | | | | 1790 | | | | 1795 | | | |
| ttt | gac | cca | gag | gcc | act | cag | ttt | att | gag | tat | tcg | gtc | ctg | tct | 5636 |
| Phe | Asp | Pro | Glu | Ala | Thr | Gln | Phe | Ile | Glu | Tyr | Ser | Val | Leu | Ser | |
| 1800 | | | | 1805 | | | | 1810 | | | |
| gac | ttt | gcc | gat | gcc | ctg | tct | gag | cca | ctc | cgt | atc | gcc | aag | ccc | 5681 |
| Asp | Phe | Ala | Asp | Ala | Leu | Ser | Glu | Pro | Leu | Arg | Ile | Ala | Lys | Pro | |
| 1815 | | | | 1820 | | | | 1825 | | | |
| aac | cag | ata | agc | ctc | atc | aac | atg | gac | ctg | ccc | atg | gtg | agt | ggg | 5726 |
| Asn | Gln | Ile | Ser | Leu | Ile | Asn | Met | Asp | Leu | Pro | Met | Val | Ser | Gly | |
| 1830 | | | | 1835 | | | | 1840 | | | |
| gac | cgc | atc | cat | tgc | atg | gac | att | ctc | ttt | gcc | ttc | acc | aaa | agg | 5771 |
| Asp | Arg | Ile | His | Cys | Met | Asp | Ile | Leu | Phe | Ala | Phe | Thr | Lys | Arg | |
| 1845 | | | | 1850 | | | | 1855 | | | |
| gtc | ctg | ggg | gag | tct | ggg | gag | atg | gac | gcc | ctg | aag | atc | cag | atg | 5816 |
| Val | Leu | Gly | Glu | Ser | Gly | Glu | Met | Asp | Ala | Leu | Lys | Ile | Gln | Met | |
| 1860 | | | | 1865 | | | | 1870 | | | |
| gag | gag | aag | ttc | atg | gca | gcc | aac | cca | tcc | aag | atc | tcc | tac | gag | 5861 |
| Glu | Glu | Lys | Phe | Met | Ala | Ala | Asn | Pro | Ser | Lys | Ile | Ser | Tyr | Glu | |
| 1875 | | | | 1880 | | | | 1885 | | | |
| ccc | atc | acc | acc | aca | ctc | cgg | cgc | aag | cac | gaa | gag | gtg | tcg | gcc | 5906 |
| Pro | Ile | Thr | Thr | Thr | Leu | Arg | Arg | Lys | His | Glu | Glu | Val | Ser | Ala | |
| 1890 | | | | 1895 | | | | 1900 | | | |
| atg | gtt | atc | cag | aga | gcc | ttc | cgc | agg | cac | ctg | ctg | caa | cgc | tct | 5951 |
| Met | Val | Ile | Gln | Arg | Ala | Phe | Arg | Arg | His | Leu | Leu | Gln | Arg | Ser | |

| | | | | | | | | | | | | |
|---|---|---|---|---|---|---|---|---|---|---|---|---|
| | | | | 1905 | | | | 1910 | | | 1915 | |
| ttg | aag | cat | gcc | tcc | ttc | ctc | ttc | cgt | cag | cag | gcg | ggc | agc | ggc | 5996 |
| Leu | Lys | His | Ala | Ser | Phe | Leu | Phe | Arg | Gln | Gln | Ala | Gly | Ser | Gly | |
| 1920 | | | | | 1925 | | | | | 1930 | | | | | |
| ctc | tcc | gaa | gag | gat | gcc | cct | gag | cga | gag | ggc | ctc | atc | gcc | tac | 6041 |
| Leu | Ser | Glu | Glu | Asp | Ala | Pro | Glu | Arg | Glu | Gly | Leu | Ile | Ala | Tyr | |
| 1935 | | | | | 1940 | | | | | 1945 | | | | | |
| gtg | atg | agt | gag | aac | ttc | tcc | cga | ccc | ctt | ggc | cca | ccc | tcc | agc | 6086 |
| Val | Met | Ser | Glu | Asn | Phe | Ser | Arg | Pro | Leu | Gly | Pro | Pro | Ser | Ser | |
| 1950 | | | | | 1955 | | | | | 1960 | | | | | |
| tcc | tcc | atc | tcc | tcc | act | tcc | ttc | cca | ccc | tcc | tat | gac | agt | gtc | 6131 |
| Ser | Ser | Ile | Ser | Ser | Thr | Ser | Phe | Pro | Pro | Ser | Tyr | Asp | Ser | Val | |
| 1965 | | | | | 1970 | | | | | 1975 | | | | | |
| act | aga | gcc | acc | agc | gat | aac | ctc | cag | gtg | cgg | ggg | tct | gac | tac | 6176 |
| Thr | Arg | Ala | Thr | Ser | Asp | Asn | Leu | Gln | Val | Arg | Gly | Ser | Asp | Tyr | |
| 1980 | | | | | 1985 | | | | | 1990 | | | | | |
| agc | cac | agt | gaa | gat | ctc | gcc | gac | ttc | ccc | cct | tct | ccg | gac | agg | 6221 |
| Ser | His | Ser | Glu | Asp | Leu | Ala | Asp | Phe | Pro | Pro | Ser | Pro | Asp | Arg | |
| 1995 | | | | | 2000 | | | | | 2005 | | | | | |
| gac | cgt | gag | tcc | atc | gtg | tga | gcctcggcct | | | ggctggccag | | gacacactga | | | 6272 |
| Asp | Arg | Glu | Ser | Ile | Val | | | | | | | | | | |
| 2010 | | | | | 2015 | | | | | | | | | | |

```
aaagcagcct ttttcaccat ggcaaaccta aatgcagtca gtcacaaacc agcctggggc    6332
cttcctggct ttgggagtaa gaaatgggcc tcagccccgc ggatcaacca ggcagagttc    6392
tgtggcgccg cgtggacagc cggagcagtt ggcctgtgct tggaggcctc agatagacct    6452
gtgacctggt ctggtcaggc aatgccctgc ggctctggaa agcaacttca tcccagctgc    6512
tgaggcgaaa tataaaactg agactgtata tgttgtgaat gggctttcat aaatttatta    6572
tatttgatat ttttttactt gagcaaagaa ctaaggattt ttccatggac atgggcagca    6632
attcacgctg tctcttctta accctgaaca agagtgtcta tggagcagcc ggaagtctgt    6692
tctcaaagca gaagtggaat ccagtgtggc tcccacaggt cttcactgcc cagggggtcga    6752 atggggtccc cctcccactt gacctgagat gctgggaggg ctgaaccccc actcacacaa    6812
gcacacacac acagtcctca cacacggagg ccagacacag gccgtgggac ccaggctccc    6872
agcctaaggg agacaggcct ttccctgccg gccccccaag gatggggttc ttgtccacgg    6932
ggctcactct ggcccctat tgtctccaag gtcccatttt cccctgtgt tttcacgcag    6992 gtcatattgt cagtcctaca aaaataaaag gcttccagag gagagtggcc tgggtcccag    7052
ggctggccct aggcactgat agttgccttt tcttcccctc ctgtaagagt attaacaaaa    7112
ccaaaggaca caagggtgca agccccattc acggcctggc atgcagcttg tccttgctcc    7172
tggaacctgg caggccctgc ccagccagcc atcggaagag agggctgagc catgggggtt    7232
tggggctaag aagttcacca gccctgagcc atggcggccc ctcagcctgc ctgaagagag    7292
gaaactggcg atctcccagg gctctctgga ccatacgcgg aggagttttc tgtgtggtct    7352
ccagctcctc tccagacaca gagacatggg agtggggagc ggagcttggc cctgcgccct    7412
gtgcagggaa agggatggtc aggcccagtt ctcgtgccct tagaggggaa tgaaccatgg    7472 caccctttgag agaggggggca ctgtggtcag gcccagcctc tctggctcag cccgggatcc    7532
tgatggcacc cacacagagg acctctttgg ggcaagatcc aggtggtccc ataggtcttg    7592
tgaaaaggct ttttcaggga aaaatatttt actagtccaa tcaccccag gacctcttca    7652 gctgctgaca atcctattta gcatatgcaa atcttttaac atagagaact gtcaccctga    7712
ggtaacaggg tcaactggcg aagcctgagc aggcaggggc ttggctgccc cattccagct    7772
```

```
ctcccatgga gcccctccac cgggcgcatg cctcccaggc cacctcagtc tcacctgccg   7832
gctctgggct ggctgctcct aacctacctc gccgagctgt cggagggctg gacatttgtg   7892
gcagtgctga aggggcattg ccggcgagt aaagtattat gtttcttctt gtcaccccag    7952
ttcccttggt ggcaacccca gacccaaccc atgcccctga cagatctagt tctcttctcc   8012
tgtgttccct ttgagtccag tgtgggacac ggtttaactg tcccagcgac atttctccaa   8072
gtggaaatcc tattttttgta gatctccatg ctttgctctc aaggcttgga gaggtatgtg  8132
cccctcctgg gtgctcaccg cctgctacac aggcaggaat gcggttggga ggcaggtcgg   8192
gctgccagcc cagctggccg gaaggagact gtggttttttg tgtgtgtgga cagcccggga  8252
gctttgagac aggtgcctgg ggctggctgc agacggtgtg gttggggtg ggaggtgagc    8312 tagacccaac ccttagcttt tagcctggct gtcacctttt taatttccag aactgcacaa   8372
tgaccagcag gagggaagga cagacatcaa gtgccagatg ttgtctgaac taatcgagca   8432
cttctcacca aacttcatgt ataaataaaa tacatatttt taaaacaaac caataaatgg   8492
cttacatga                                                          8501
```

<210> SEQ ID NO 9
<211> LENGTH: 2015
<212> TYPE: PRT
<213> ORGANISM: Homo sapiens

<400> SEQUENCE: 9

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
```

```
                245                 250                 255
Thr Val Phe Cys Leu Ser Val Phe Ala Leu Ile Gly Leu Gln Leu Phe
                260                 265                 270

Met Gly Asn Leu Arg His Lys Cys Val Arg Asn Phe Thr Ala Leu Asn
            275                 280                 285

Gly Thr Asn Gly Ser Val Glu Ala Asp Gly Leu Val Trp Glu Ser Leu
        290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
    370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
            420                 425                 430

Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
    450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Arg Asp Leu Gly Ser Glu Ala Asp Phe Ala
    530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
    610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670
```

```
Leu Glu Glu Leu Glu Glu Ser Arg His Lys Cys Pro Pro Cys Trp Asn
            675                 680                 685

Arg Leu Ala Gln Arg Tyr Leu Ile Trp Glu Cys Cys Pro Leu Trp Met
            690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
            725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
            805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
            835                 840                 845

Ile Val Phe Ile Phe Ala Val Val Gly Met Gln Leu Phe Gly Lys Asn
850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
            885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
            915                 920                 925

Val Val Leu Asn Leu Phe Leu Ala Leu Leu Leu Ser Ser Phe Ser Ala
930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
            965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln Leu Pro Ser Cys Ile Ala Thr Pro
            995                 1000                1005

Tyr Ser Pro Pro Pro Pro Glu Thr Glu Lys Val Pro Pro Thr Arg
        1010                1015                1020

Lys Glu Thr Arg Phe Glu Glu Gly Glu Gln Pro Gly Gln Gly Thr
        1025                1030                1035

Pro Gly Asp Pro Glu Pro Val Cys Val Pro Ile Ala Val Ala Glu
        1040                1045                1050

Ser Asp Thr Asp Asp Gln Glu Asp Glu Glu Asn Ser Leu Gly
        1055                1060                1065

Thr Glu Glu Glu Ser Ser Lys Gln Glu Ser Gln Pro Val Ser Gly
        1070                1075                1080

Gly Pro Glu Ala Pro Pro Asp Ser Arg Thr Trp Ser Gln Val Ser
        1085                1090                1095
```

```
Ala Thr Ala Ser Ser Glu Glu Ala Ser Ala Ser Gln Ala Asp
    1100                1105                1110

Trp Arg Gln Gln Trp Lys Ala Glu Pro Gln Ala Pro Gly Cys Gly
    1115                1120                1125

Glu Thr Pro Glu Asp Ser Cys Ser Glu Gly Ser Thr Ala Asp Met
    1130                1135                1140

Thr Asn Thr Ala Glu Leu Leu Glu Gln Ile Pro Asp Leu Gly Gln
    1145                1150                1155

Asp Val Lys Asp Pro Glu Asp Cys Phe Thr Glu Gly Cys Val Arg
    1160                1165                1170

Arg Cys Pro Cys Cys Ala Val Asp Thr Thr Gln Ala Pro Gly Lys
    1175                1180                1185

Val Trp Trp Arg Leu Arg Lys Thr Cys Tyr His Ile Val Glu His
    1190                1195                1200

Ser Trp Phe Glu Thr Phe Ile Ile Phe Met Ile Leu Leu Ser Ser
    1205                1210                1215

Gly Ala Leu Ala Phe Glu Asp Ile Tyr Leu Glu Glu Arg Lys Thr
    1220                1225                1230

Ile Lys Val Leu Leu Glu Tyr Ala Asp Lys Met Phe Thr Tyr Val
    1235                1240                1245

Phe Val Leu Glu Met Leu Leu Lys Trp Val Ala Tyr Gly Phe Lys
    1250                1255                1260

Lys Tyr Phe Thr Asn Ala Trp Cys Trp Leu Asp Phe Leu Ile Val
    1265                1270                1275

Asp Val Ser Leu Val Ser Leu Val Ala Asn Thr Leu Gly Phe Ala
    1280                1285                1290

Glu Met Gly Pro Ile Lys Ser Leu Arg Thr Leu Arg Ala Leu Arg
    1295                1300                1305

Pro Leu Arg Ala Leu Ser Arg Phe Glu Gly Met Arg Val Val Val
    1310                1315                1320

Asn Ala Leu Val Gly Ala Ile Pro Ser Ile Met Asn Val Leu Leu
    1325                1330                1335

Val Cys Leu Ile Phe Trp Leu Ile Phe Ser Ile Met Gly Val Asn
    1340                1345                1350

Leu Phe Ala Gly Lys Phe Gly Arg Cys Ile Asn Gln Thr Glu Gly
    1355                1360                1365

Asp Leu Pro Leu Asn Tyr Thr Ile Val Asn Asn Lys Ser Gln Cys
    1370                1375                1380

Glu Ser Leu Asn Leu Thr Gly Glu Leu Tyr Trp Thr Lys Val Lys
    1385                1390                1395

Val Asn Phe Asp Asn Val Gly Ala Gly Tyr Leu Ala Leu Leu Gln
    1400                1405                1410

Val Ala Thr Phe Lys Gly Trp Met Asp Ile Met Tyr Ala Ala Val
    1415                1420                1425

Asp Ser Arg Gly Tyr Glu Glu Gln Pro Gln Trp Glu Tyr Asn Leu
    1430                1435                1440

Tyr Met Tyr Ile Tyr Phe Val Ile Phe Ile Ile Phe Gly Ser Phe
    1445                1450                1455

Phe Thr Leu Asn Leu Phe Ile Gly Val Ile Ile Asp Asn Phe Asn
    1460                1465                1470

Gln Gln Lys Lys Lys Leu Gly Gly Gln Asp Ile Phe Met Thr Glu
    1475                1480                1485

Glu Gln Lys Lys Tyr Tyr Asn Ala Met Lys Lys Leu Gly Ser Lys
```

-continued

```
              1490                1495                1500

Lys Pro Gln Lys Pro Ile Pro Arg Pro Leu Asn Lys Tyr Gln Gly
    1505                1510                1515

Phe Ile Phe Asp Ile Val Thr Lys Gln Ala Phe Asp Val Thr Ile
    1520                1525                1530

Met Phe Leu Ile Cys Leu Asn Met Val Thr Met Val Glu Thr
    1535                1540                1545

Asp Asp Gln Ser Pro Glu Lys Ile Asn Ile Leu Ala Lys Ile Asn
    1550                1555                1560

Leu Leu Phe Val Ala Ile Phe Thr Gly Glu Cys Ile Val Lys Leu
    1565                1570                1575

Ala Ala Leu Arg His Tyr Tyr Phe Thr Asn Ser Trp Asn Ile Phe
    1580                1585                1590

Asp Phe Val Val Val Ile Leu Ser Ile Val Gly Thr Val Leu Ser
    1595                1600                1605

Asp Ile Ile Gln Lys Tyr Phe Phe Ser Pro Thr Leu Phe Arg Val
    1610                1615                1620

Ile Arg Leu Ala Arg Ile Gly Arg Ile Leu Arg Leu Ile Arg Gly
    1625                1630                1635

Ala Lys Gly Ile Arg Thr Leu Leu Phe Ala Leu Met Met Ser Leu
    1640                1645                1650

Pro Ala Leu Phe Asn Ile Gly Leu Leu Leu Phe Leu Val Met Phe
    1655                1660                1665

Ile Tyr Ser Ile Phe Gly Met Ala Asn Phe Ala Tyr Val Lys Trp
    1670                1675                1680

Glu Ala Gly Ile Asp Asp Met Phe Asn Phe Gln Thr Phe Ala Asn
    1685                1690                1695

Ser Met Leu Cys Leu Phe Gln Ile Thr Thr Ser Ala Gly Trp Asp
    1700                1705                1710

Gly Leu Leu Ser Pro Ile Leu Asn Thr Gly Pro Pro Tyr Cys Asp
    1715                1720                1725

Pro Thr Leu Pro Asn Ser Asn Gly Ser Arg Gly Asp Cys Gly Ser
    1730                1735                1740

Pro Ala Val Gly Ile Leu Phe Phe Thr Thr Tyr Ile Ile Ile Ser
    1745                1750                1755

Phe Leu Ile Val Val Asn Met Tyr Ile Ala Ile Ile Leu Glu Asn
    1760                1765                1770

Phe Ser Val Ala Thr Glu Glu Ser Thr Glu Pro Leu Ser Glu Asp
    1775                1780                1785

Asp Phe Asp Met Phe Tyr Glu Ile Trp Glu Lys Phe Asp Pro Glu
    1790                1795                1800

Ala Thr Gln Phe Ile Glu Tyr Ser Val Leu Ser Asp Phe Ala Asp
    1805                1810                1815

Ala Leu Ser Glu Pro Leu Arg Ile Ala Lys Pro Asn Gln Ile Ser
    1820                1825                1830

Leu Ile Asn Met Asp Leu Pro Met Val Ser Gly Asp Arg Ile His
    1835                1840                1845

Cys Met Asp Ile Leu Phe Ala Phe Thr Lys Arg Val Leu Gly Glu
    1850                1855                1860

Ser Gly Glu Met Asp Ala Leu Lys Ile Gln Met Glu Glu Lys Phe
    1865                1870                1875

Met Ala Ala Asn Pro Ser Lys Ile Ser Tyr Glu Pro Ile Thr Thr
    1880                1885                1890
```

```
Thr Leu Arg Arg Lys His Glu Glu Val Ser Ala Met Val Ile Gln
    1895                1900                1905

Arg Ala Phe Arg Arg His Leu Leu Gln Arg Ser Leu Lys His Ala
    1910                1915                1920

Ser Phe Leu Phe Arg Gln Gln Ala Gly Ser Gly Leu Ser Glu Glu
    1925                1930                1935

Asp Ala Pro Glu Arg Glu Gly Leu Ile Ala Tyr Val Met Ser Glu
    1940                1945                1950

Asn Phe Ser Arg Pro Leu Gly Pro Pro Ser Ser Ser Ile Ser
    1955                1960                1965

Ser Thr Ser Phe Pro Pro Ser Tyr Asp Ser Val Thr Arg Ala Thr
    1970                1975                1980

Ser Asp Asn Leu Gln Val Arg Gly Ser Asp Tyr Ser His Ser Glu
    1985                1990                1995

Asp Leu Ala Asp Phe Pro Pro Ser Pro Asp Arg Asp Arg Glu Ser
    2000                2005                2010

Ile Val
    2015

<210> SEQ ID NO 10
<211> LENGTH: 8504
<212> TYPE: DNA
<213> ORGANISM: Homo sapiens
<220> FEATURE:
<221> NAME/KEY: CDS
<222> LOCATION: (195)..(6245)

<400> SEQUENCE: 10
agacggcggc ggcgcccgta ggatgcaggg atcgctcccc cggggccgct gagcctgcgc      60
ccagtgcccc gagcccgcg ccgagccgag tccgcgccaa gcagcagccg cccacccgg      120 ggcccggccg gggaccagc agcttcccca caggcaacgt gaggagagcc tgtgcccaga     180
agcaggatga gaag atg gca aac ttc cta tta cct cgg ggc acc agc agc      230
              Met Ala Asn Phe Leu Leu Pro Arg Gly Thr Ser Ser
                1               5                  10 ttc cgc agg ttc aca cgg gag tcc ctg gca gcc atc gag aag cgc atg      278
Phe Arg Arg Phe Thr Arg Glu Ser Leu Ala Ala Ile Glu Lys Arg Met
    15                  20                  25 gca gag aag caa gcc cgc ggc tca acc acc ttg cag gag agc cga gag      326
Ala Glu Lys Gln Ala Arg Gly Ser Thr Thr Leu Gln Glu Ser Arg Glu
30                  35                  40 ggg ctg ccc gag gag gag gct ccc cgg ccc cag ctg gac ctg cag gcc      374
Gly Leu Pro Glu Glu Glu Ala Pro Arg Pro Gln Leu Asp Leu Gln Ala
45                  50                  55                  60 tcc aaa aag ctg cca gat ctc tat ggc aat cca ccc caa gag ctc atc      422
Ser Lys Lys Leu Pro Asp Leu Tyr Gly Asn Pro Pro Gln Glu Leu Ile
                65                  70                  75 gga gag ccc ctg gag gac ctg gac ccc ttc tat agc acc caa aag act      470
Gly Glu Pro Leu Glu Asp Leu Asp Pro Phe Tyr Ser Thr Gln Lys Thr
            80                  85                  90 ttc atc gta ctg aat aaa ggc aag acc atc ttc cgg ttc agt gcc acc      518
Phe Ile Val Leu Asn Lys Gly Lys Thr Ile Phe Arg Phe Ser Ala Thr
        95                  100                 105 aac gcc ttg tat gtc ctc agt ccc ttc cac ccc atc cgg aga gcg gct      566
Asn Ala Leu Tyr Val Leu Ser Pro Phe His Pro Ile Arg Arg Ala Ala
    110                 115                 120 gtg aag att ctg gtt cac tcg ctc ttc aac atg ctc atc atg tgc acc      614
Val Lys Ile Leu Val His Ser Leu Phe Asn Met Leu Ile Met Cys Thr
125                 130                 135                 140
```

```
atc ctc acc aac tgc gtg ttc atg gcc cag cac gac cct cca ccc tgg      662
Ile Leu Thr Asn Cys Val Phe Met Ala Gln His Asp Pro Pro Pro Trp
            145                 150                 155 acc aag tat gtc gag tac acc ttc acc gcc att tac acc ttt gag tct      710
Thr Lys Tyr Val Glu Tyr Thr Phe Thr Ala Ile Tyr Thr Phe Glu Ser
            160                 165                 170 ctg gtc aag att ctg gct cga ggc ttc tgc ctg cac gcg ttc act ttc      758
Leu Val Lys Ile Leu Ala Arg Gly Phe Cys Leu His Ala Phe Thr Phe
            175                 180                 185 ctt cgg gac cca tgg aac tgg ctg gac ttt agt gtg att atc atg gcg      806
Leu Arg Asp Pro Trp Asn Trp Leu Asp Phe Ser Val Ile Ile Met Ala
        190                 195                 200 tat gta tca gaa aat ata aaa cta ggc aat ttg tcg gct ctt cga act      854
Tyr Val Ser Glu Asn Ile Lys Leu Gly Asn Leu Ser Ala Leu Arg Thr
205                 210                 215                 220 ttc aga gtc ctg aga gct cta aaa act att tca gtt atc cca ggg ctg      902
Phe Arg Val Leu Arg Ala Leu Lys Thr Ile Ser Val Ile Pro Gly Leu
                225                 230                 235 aag acc atc gtg ggg gcc ctg atc cag tct gtg aag aag ctg gct gat      950
Lys Thr Ile Val Gly Ala Leu Ile Gln Ser Val Lys Lys Leu Ala Asp
                240                 245                 250 gtg atg gtc ctc aca gtc ttc tgc ctc agc gtc ttt gcc ctc atc ggc      998
Val Met Val Leu Thr Val Phe Cys Leu Ser Val Phe Ala Leu Ile Gly
            255                 260                 265 ctg cag ctc ttc atg ggc aac cta agg cac aag tgc gtg cgc aac ttc     1046
Leu Gln Leu Phe Met Gly Asn Leu Arg His Lys Cys Val Arg Asn Phe
        270                 275                 280 aca gcg ctc aac ggc acc aac ggc tcc gtg gag gcc gac ggc ttg gtc     1094
Thr Ala Leu Asn Gly Thr Asn Gly Ser Val Glu Ala Asp Gly Leu Val
285                 290                 295                 300 tgg gaa tcc ctg gac ctt tac ctc agt gat cca gaa aat tac ctg ctc     1142
Trp Glu Ser Leu Asp Leu Tyr Leu Ser Asp Pro Glu Asn Tyr Leu Leu
                305                 310                 315 aag aac ggc acc tct gat gtg tta ctg tgt ggg aac agc tct gac gct     1190
Lys Asn Gly Thr Ser Asp Val Leu Leu Cys Gly Asn Ser Ser Asp Ala
                320                 325                 330 ggg aca tgt ccg gag ggc tac cgg tgc cta aag gca ggc gag aac ccc     1238
Gly Thr Cys Pro Glu Gly Tyr Arg Cys Leu Lys Ala Gly Glu Asn Pro
            335                 340                 345 gac cac ggc tac acc agc ttc gat tcc ttt gcc tgg gcc ttt ctt gca     1286
Asp His Gly Tyr Thr Ser Phe Asp Ser Phe Ala Trp Ala Phe Leu Ala
        350                 355                 360 ctc ttc cgc ctg atg acg cag gac tgc tgg gag cgc ctc tat cag cag     1334
Leu Phe Arg Leu Met Thr Gln Asp Cys Trp Glu Arg Leu Tyr Gln Gln
365                 370                 375                 380 acc ctc agg tcc gca ggg aag atc tac atg atc ttc ttc atg ctt gtc     1382
Thr Leu Arg Ser Ala Gly Lys Ile Tyr Met Ile Phe Phe Met Leu Val
                385                 390                 395 atc ttc ctg ggg tcc ttc tac ctg gtg aac ctg atc ctg gcc gtg gtc     1430
Ile Phe Leu Gly Ser Phe Tyr Leu Val Asn Leu Ile Leu Ala Val Val
                400                 405                 410 gca atg gcc tat gag gag caa aac caa gcc acc atc gct gag acc gag     1478
Ala Met Ala Tyr Glu Glu Gln Asn Gln Ala Thr Ile Ala Glu Thr Glu
            415                 420                 425 gag aag gaa aag cgc ttc cag gag gcc atg gaa atg ctc aag aaa gaa     1526
Glu Lys Glu Lys Arg Phe Gln Glu Ala Met Glu Met Leu Lys Lys Glu
        430                 435                 440 cac gag gcc ctc acc atc agg ggt gtg gat acc gtg tcc cgt agc tcc     1574
His Glu Ala Leu Thr Ile Arg Gly Val Asp Thr Val Ser Arg Ser Ser
445                 450                 455                 460
```

```
ttg gag atg tcc cct ttg gcc cca gta aac agc cat gag aga aga agc    1622
Leu Glu Met Ser Pro Leu Ala Pro Val Asn Ser His Glu Arg Arg Ser
            465             470             475 aag agg aga aaa cgg atg tct tca gga act gag gag tgt ggg gag gac    1670
Lys Arg Arg Lys Arg Met Ser Ser Gly Thr Glu Glu Cys Gly Glu Asp
        480             485             490 agg ctc ccc aag tct gac tca gaa gat ggt ccc aga gca atg aat cat    1718
Arg Leu Pro Lys Ser Asp Ser Glu Asp Gly Pro Arg Ala Met Asn His
            495             500             505 ctc agc ctc acc cgt ggc ctc agc agg act tct atg aag cca cgt tcc    1766
Leu Ser Leu Thr Arg Gly Leu Ser Arg Thr Ser Met Lys Pro Arg Ser
        510             515             520 agc cgc ggg agc att ttc acc ttt cgc agg cga gac ctg ggt tct gaa    1814
Ser Arg Gly Ser Ile Phe Thr Phe Arg Arg Arg Asp Leu Gly Ser Glu
525             530             535             540 gca gat ttt gca gat gat gaa aac agc aca gcg ggg gag agc gag agc    1862
Ala Asp Phe Ala Asp Asp Glu Asn Ser Thr Ala Gly Glu Ser Glu Ser
            545             550             555 cac cac aca tca ctg ctg gtg ccc tgg ccc ctg cgc cgg acc agt gcc    1910
His His Thr Ser Leu Leu Val Pro Trp Pro Leu Arg Arg Thr Ser Ala
        560             565             570 cag gga cag ccc agt ccc gga acc tcg gct cct ggc cac gcc ctc cat    1958
Gln Gly Gln Pro Ser Pro Gly Thr Ser Ala Pro Gly His Ala Leu His
            575             580             585 ggc aaa aag aac agc act gtg gac tgc aat ggg gtg gtc tca tta ctg    2006
Gly Lys Lys Asn Ser Thr Val Asp Cys Asn Gly Val Val Ser Leu Leu
        590             595             600 ggg gca ggc gac cca gag gcc aca tcc cca gga agc cac ctc ctc cgc    2054
Gly Ala Gly Asp Pro Glu Ala Thr Ser Pro Gly Ser His Leu Leu Arg
605             610             615             620 cct gtg atg cta gag cac ccg cca gac acg acc acg cca tcg gag gag    2102
Pro Val Met Leu Glu His Pro Pro Asp Thr Thr Thr Pro Ser Glu Glu
            625             630             635 cca ggc ggg ccc cag atg ctg acc tcc cag gct ccg tgt gta gat ggc    2150
Pro Gly Gly Pro Gln Met Leu Thr Ser Gln Ala Pro Cys Val Asp Gly
        640             645             650 ttc gag gag cca gga gca cgg cag cgg gcc ctc agc gca gtc agc gtc    2198
Phe Glu Glu Pro Gly Ala Arg Gln Arg Ala Leu Ser Ala Val Ser Val
            655             660             665 ctc acc agc gca ctg gaa gag tta gag gag tct cgc cac aag tgt cca    2246
Leu Thr Ser Ala Leu Glu Glu Leu Glu Glu Ser Arg His Lys Cys Pro
        670             675             680 cca tgc tgg aac cgt ctc gcc cag cgc tac ctg atc tgg gag tgc tgc    2294
Pro Cys Trp Asn Arg Leu Ala Gln Arg Tyr Leu Ile Trp Glu Cys Cys
685             690             695             700 ccg ctg tgg atg tcc atc aag cag gga gtg aag ttg gtg gtc atg gac    2342
Pro Leu Trp Met Ser Ile Lys Gln Gly Val Lys Leu Val Val Met Asp
            705             710             715 ccg ttt act gac ctc acc atc act atg tgc atc gta ctc aac aca ctc    2390
Pro Phe Thr Asp Leu Thr Ile Thr Met Cys Ile Val Leu Asn Thr Leu
        720             725             730 ttc atg gcg ctg gag cac tac aac atg aca agt gaa ttc gag gag atg    2438
Phe Met Ala Leu Glu His Tyr Asn Met Thr Ser Glu Phe Glu Glu Met
            735             740             745 ctg cag gtc gga aac ctg gtc ttc aca ggg att ttc aca gca gag atg    2486
Leu Gln Val Gly Asn Leu Val Phe Thr Gly Ile Phe Thr Ala Glu Met
        750             755             760 acc ttc aag atc att gcc ctc gac ccc tac tac tac ttc caa cag ggc    2534
Thr Phe Lys Ile Ile Ala Leu Asp Pro Tyr Tyr Tyr Phe Gln Gln Gly
765             770             775             780
```

```
                                                        -continued
tgg aac atc ttc gac agc atc atc gtc atc ctt agc ctc atg gag ctg         2582
Trp Asn Ile Phe Asp Ser Ile Ile Val Ile Leu Ser Leu Met Glu Leu
            785                 790                 795 ggc ctg tcc cgc atg agc aac ttg tcg gtg ctg cgc tcc ttc cgc ctg         2630
Gly Leu Ser Arg Met Ser Asn Leu Ser Val Leu Arg Ser Phe Arg Leu
        800                 805                 810 ctg cgg gtc ttc aag ctg gcc aaa tca tgg ccc acc ctg aac aca ctc         2678
Leu Arg Val Phe Lys Leu Ala Lys Ser Trp Pro Thr Leu Asn Thr Leu
        815                 820                 825 atc aag atc atc ggg aac tca gtg ggg gca ctg ggg aac ctg aca ctg         2726
Ile Lys Ile Ile Gly Asn Ser Val Gly Ala Leu Gly Asn Leu Thr Leu
        830                 835                 840 gtg cta gcc atc atc gtg ttc atc ttt gct gtg gtg ggc atg cag ctc         2774
Val Leu Ala Ile Ile Val Phe Ile Phe Ala Val Val Gly Met Gln Leu
845                 850                 855                 860 ttt ggc aag aac tac tcg gag ctg agg gac agc gac tca ggc ctg ctg         2822
Phe Gly Lys Asn Tyr Ser Glu Leu Arg Asp Ser Asp Ser Gly Leu Leu
            865                 870                 875 cct cgc tgg cac atg atg gac ttc ttt cat gcc ttc ctc atc atc ttc         2870
Pro Arg Trp His Met Met Asp Phe Phe His Ala Phe Leu Ile Ile Phe
            880                 885                 890 cgc atc ctc tgt gga gag tgg atc gag acc atg tgg gac tgc atg gag         2918
Arg Ile Leu Cys Gly Glu Trp Ile Glu Thr Met Trp Asp Cys Met Glu
            895                 900                 905 gtg tcg ggg cag tca tta tgc ctg ctg gtc ttc ttg ctt gtt atg gtc         2966
Val Ser Gly Gln Ser Leu Cys Leu Leu Val Phe Leu Leu Val Met Val
            910                 915                 920 att ggc aac ctt gtg gtc ctg aat ctc ttc ctg gcc ttg ctg ctc agc         3014
Ile Gly Asn Leu Val Val Leu Asn Leu Phe Leu Ala Leu Leu Leu Ser
925                 930                 935                 940 tcc ttc agt gca gac aac ctc aca gcc cct gat gag gac aga gag atg         3062
Ser Phe Ser Ala Asp Asn Leu Thr Ala Pro Asp Glu Asp Arg Glu Met
            945                 950                 955 aac aac ctc cag ctg gcc ctg gcc cgc atc cag agg ggc ctg cgc ttc         3110
Asn Asn Leu Gln Leu Ala Leu Ala Arg Ile Gln Arg Gly Leu Arg Phe
            960                 965                 970 gtc aag cgg acc acc tgg gat ttc tgc tgt ggt ctc ctg cgg cag cgg         3158
Val Lys Arg Thr Thr Trp Asp Phe Cys Cys Gly Leu Leu Arg Gln Arg
            975                 980                 985 cct cag aag ccc gca gcc ctt gcc gcc cag ggc cag ctg ccc agc tgc         3206
Pro Gln Lys Pro Ala Ala Leu Ala Ala Gln Gly Gln Leu Pro Ser Cys
            990                 995                 1000 att gcc acc ccc tac tcc ccg cca ccc cca gag acg gag aag gtg              3251
Ile Ala Thr Pro Tyr Ser Pro Pro Pro Pro Glu Thr Glu Lys Val
1005                1010                1015 cct ccc acc cgc aag gaa aca cgg ttt gag gaa ggc gag caa cca              3296
Pro Pro Thr Arg Lys Glu Thr Arg Phe Glu Glu Gly Glu Gln Pro
1020                1025                1030 ggc cag ggc acc ccc ggg gat cca gag ccc gtg tgt gtg ccc atc              3341
Gly Gln Gly Thr Pro Gly Asp Pro Glu Pro Val Cys Val Pro Ile
1035                1040                1045 gct gtg gcc gag tca gac aca gat gac caa gaa gaa gat gag gag              3386
Ala Val Ala Glu Ser Asp Thr Asp Asp Gln Glu Glu Asp Glu Glu
1050                1055                1060 aac agc ctg ggc acg gag gag gag tcc agc aag cag cag gaa tcc              3431
Asn Ser Leu Gly Thr Glu Glu Glu Ser Ser Lys Gln Gln Glu Ser
1065                1070                1075 cag cct gtg tcc ggt ggc cca gag gcc cct ccg gat tcc agg acc              3476
Gln Pro Val Ser Gly Gly Pro Glu Ala Pro Pro Asp Ser Arg Thr
1080                1085                1090
```

```
                                          -continued
tgg agc cag gtg tca gcg act gcc tcc tct gag gcc gag gcc agt      3521
Trp Ser Gln Val Ser Ala Thr Ala Ser Ser Glu Ala Glu Ala Ser
1095                1100                1105 gca tct cag gcc gac tgg cgg cag cag tgg aaa gcg gaa ccc cag      3566
Ala Ser Gln Ala Asp Trp Arg Gln Gln Trp Lys Ala Glu Pro Gln
1110                1115                1120 gcc cca ggg tgc ggt gag acc cca gag gac agt tgc tcc gag ggc      3611
Ala Pro Gly Cys Gly Glu Thr Pro Glu Asp Ser Cys Ser Glu Gly
1125                1130                1135 agc aca gca gac atg acc aac acc gct gag ctc ctg gag cag atc      3656
Ser Thr Ala Asp Met Thr Asn Thr Ala Glu Leu Leu Glu Gln Ile
1140                1145                1150 cct gac ctc ggc cag gat gtc aag gac cca gag gac tgc ttc act      3701
Pro Asp Leu Gly Gln Asp Val Lys Asp Pro Glu Asp Cys Phe Thr
1155                1160                1165 gaa ggc tgt gtc cgg cgc tgt ccc tgc tgt gcg gtg gac acc aca      3746
Glu Gly Cys Val Arg Arg Cys Pro Cys Cys Ala Val Asp Thr Thr
1170                1175                1180 cag gcc cca ggg aag gtc tgg tgg cgg ttg cgc aag acc tgc tac      3791
Gln Ala Pro Gly Lys Val Trp Trp Arg Leu Arg Lys Thr Cys Tyr
1185                1190                1195 cac atc gtg gag cac agc tgg ttc gag aca ttc atc atc ttc atg      3836
His Ile Val Glu His Ser Trp Phe Glu Thr Phe Ile Ile Phe Met
1200                1205                1210 atc cta ctc agc agt gga gcg ctg gcc ttc gag gac atc tac cta      3881
Ile Leu Leu Ser Ser Gly Ala Leu Ala Phe Glu Asp Ile Tyr Leu
1215                1220                1225 gag gag cgg aag acc atc aag gtt ctg ctt gag tat gcc gac aag      3926
Glu Glu Arg Lys Thr Ile Lys Val Leu Leu Glu Tyr Ala Asp Lys
1230                1235                1240 atg ttc aca tat gtc ttc gtg ctg gag atg ctg ctc aag tgg gtg      3971
Met Phe Thr Tyr Val Phe Val Leu Glu Met Leu Leu Lys Trp Val
1245                1250                1255 gcc tac ggc ttc aag aag tac ttc acc aat gcc tgg tgc tgg ctc      4016
Ala Tyr Gly Phe Lys Lys Tyr Phe Thr Asn Ala Trp Cys Trp Leu
1260                1265                1270 gac ttc ctc atc gta gac gtc tct ctg gtc agc ctg gtg gcc aac      4061
Asp Phe Leu Ile Val Asp Val Ser Leu Val Ser Leu Val Ala Asn
1275                1280                1285 acc ctg ggc ttt gcc gag atg ggc ccc atc aag tca ctg cgg acg      4106
Thr Leu Gly Phe Ala Glu Met Gly Pro Ile Lys Ser Leu Arg Thr
1290                1295                1300 ctg cgt gca ctc cgt cct ctg aga gct ctg tca cga ttt gag ggc      4151
Leu Arg Ala Leu Arg Pro Leu Arg Ala Leu Ser Arg Phe Glu Gly
1305                1310                1315 atg agg gtg gtg gtc aat gcc ctg gtg ggc gcc atc ccg tcc atc      4196
Met Arg Val Val Val Asn Ala Leu Val Gly Ala Ile Pro Ser Ile
1320                1325                1330 atg aac gtc ctc ctc gtc tgc ctc atc ttc tgg ctc atc ttc agc      4241
Met Asn Val Leu Leu Val Cys Leu Ile Phe Trp Leu Ile Phe Ser
1335                1340                1345 atc atg ggc gtg aac ctc ttt gcg ggg aag ttt ggg agg tgc atc      4286
Ile Met Gly Val Asn Leu Phe Ala Gly Lys Phe Gly Arg Cys Ile
1350                1355                1360 aac cag aca gag gga gac ttg cct ttg aac tac acc atc gtg aac      4331
Asn Gln Thr Glu Gly Asp Leu Pro Leu Asn Tyr Thr Ile Val Asn
1365                1370                1375 aac aag agc cag tgt gag tcc ttg aac ttg acc gga gaa ttg tac      4376
Asn Lys Ser Gln Cys Glu Ser Leu Asn Leu Thr Gly Glu Leu Tyr
1380                1385                1390
```

```
tgg acc aag gtg aaa gtc aac ttt gac aac gtg ggg gcc ggg tac        4421
Trp Thr Lys Val Lys Val Asn Phe Asp Asn Val Gly Ala Gly Tyr
1395            1400                1405 ctg gcc ctt ctg cag gtg gca aca ttt aaa ggc tgg atg gac att        4466
Leu Ala Leu Leu Gln Val Ala Thr Phe Lys Gly Trp Met Asp Ile
1410            1415                1420 atg tat gca gct gtg gac tcc agg ggg tat gaa gag cag cct cag        4511
Met Tyr Ala Ala Val Asp Ser Arg Gly Tyr Glu Glu Gln Pro Gln
1425            1430                1435 tgg gaa tac aac ctc tac atg tac atc tat ttt gtc att ttc atc        4556
Trp Glu Tyr Asn Leu Tyr Met Tyr Ile Tyr Phe Val Ile Phe Ile
1440            1445                1450 atc ttt ggg tct ttc ttc acc ctg aac ctc ttt att ggt gtc atc        4601
Ile Phe Gly Ser Phe Phe Thr Leu Asn Leu Phe Ile Gly Val Ile
1455            1460                1465 att gac aac ttc aac caa cag aag aaa aag tta ggg ggc cag gac        4646
Ile Asp Asn Phe Asn Gln Gln Lys Lys Lys Leu Gly Gly Gln Asp
1470            1475                1480 atc ttc atg aca gag gag cag aag aag tac tac aat gcc atg aag        4691
Ile Phe Met Thr Glu Glu Gln Lys Lys Tyr Tyr Asn Ala Met Lys
1485            1490                1495 aag ctg ggc tcc aag aag ccc cag aag ccc atc cca cgg ccc ctg        4736
Lys Leu Gly Ser Lys Lys Pro Gln Lys Pro Ile Pro Arg Pro Leu
1500            1505                1510 aac aag tac cag ggc ttc ata ttc gac att gtg acc aag cag gcc        4781
Asn Lys Tyr Gln Gly Phe Ile Phe Asp Ile Val Thr Lys Gln Ala
1515            1520                1525 ttt gac gtc acc atc atg ttt ctg atc tgc ttg aat atg gtg acc        4826
Phe Asp Val Thr Ile Met Phe Leu Ile Cys Leu Asn Met Val Thr
1530            1535                1540 atg atg gtg gag aca gat gac caa agt cct gag aaa atc aac atc        4871
Met Met Val Glu Thr Asp Asp Gln Ser Pro Glu Lys Ile Asn Ile
1545            1550                1555 ttg gcc aag atc aac ctg ctc ttt gtg gcc atc ttc aca ggc gag        4916
Leu Ala Lys Ile Asn Leu Leu Phe Val Ala Ile Phe Thr Gly Glu
1560            1565                1570 tgt att gtc aag ctg gct gcc ctg cgc cac tac tac ttc acc aac        4961
Cys Ile Val Lys Leu Ala Ala Leu Arg His Tyr Tyr Phe Thr Asn
1575            1580                1585 agc tgg aat atc ttc gac ttc gtg gtt gtc atc ctc tcc atc gtg        5006
Ser Trp Asn Ile Phe Asp Phe Val Val Val Ile Leu Ser Ile Val
1590            1595                1600 ggc act gtg ctc tcg gac atc atc cag aag tac ttc ttc tcc ccg        5051
Gly Thr Val Leu Ser Asp Ile Ile Gln Lys Tyr Phe Phe Ser Pro
1605            1610                1615 acg ctc ttc cga gtc atc cgc ctg gcc cga ata ggc cgc atc ctc        5096
Thr Leu Phe Arg Val Ile Arg Leu Ala Arg Ile Gly Arg Ile Leu
1620            1625                1630 aga ctg atc cga ggg gcc aag ggg atc cgc acg ctc ctc ttt gcc        5141
Arg Leu Ile Arg Gly Ala Lys Gly Ile Arg Thr Leu Leu Phe Ala
1635            1640                1645 ctc atg atg tcc ctg cct gcc ctc ttc aac atc ggg ctg ctg ctc        5186
Leu Met Met Ser Leu Pro Ala Leu Phe Asn Ile Gly Leu Leu Leu
1650            1655                1660 ttc ctc gtc atg ttc atc tac tcc atc ttt ggc atg gcc aac ttc        5231
Phe Leu Val Met Phe Ile Tyr Ser Ile Phe Gly Met Ala Asn Phe
1665            1670                1675 gct tat gtc aag tgg gag gct ggc atc gac gac atg ttc aac ttc        5276
Ala Tyr Val Lys Trp Glu Ala Gly Ile Asp Asp Met Phe Asn Phe
1680            1685                1690
```

```
cag  acc  ttc  gcc  aac  agc  atg  ctg  tgc  ctc  ttc  cag  atc  acc  acg        5321
Gln  Thr  Phe  Ala  Asn  Ser  Met  Leu  Cys  Leu  Phe  Gln  Ile  Thr  Thr
1695                 1700                      1705 tcg  gcc  ggc  tgg  gat  ggc  ctc  ctc  agc  ccc  atc  ctc  aac  act  ggg        5366
Ser  Ala  Gly  Trp  Asp  Gly  Leu  Leu  Ser  Pro  Ile  Leu  Asn  Thr  Gly
1710                 1715                      1720 ccg  ccc  tac  tgc  gac  ccc  act  ctg  ccc  aac  agc  aat  ggc  tct  cgg        5411
Pro  Pro  Tyr  Cys  Asp  Pro  Thr  Leu  Pro  Asn  Ser  Asn  Gly  Ser  Arg
1725                 1730                      1735 ggg  gac  tgc  ggg  agc  cca  gcc  gtg  ggc  atc  ctc  ttc  ttc  acc  acc        5456
Gly  Asp  Cys  Gly  Ser  Pro  Ala  Val  Gly  Ile  Leu  Phe  Phe  Thr  Thr
1740                 1745                      1750 tac  atc  atc  atc  tcc  ttc  ctc  atc  gtg  gtc  aac  atg  tac  att  gcc        5501
Tyr  Ile  Ile  Ile  Ser  Phe  Leu  Ile  Val  Val  Asn  Met  Tyr  Ile  Ala
1755                 1760                      1765 atc  atc  ctg  gag  aac  ttc  agc  gtg  gcc  acg  gag  gag  agc  acc  gag        5546
Ile  Ile  Leu  Glu  Asn  Phe  Ser  Val  Ala  Thr  Glu  Glu  Ser  Thr  Glu
1770                 1775                      1780 ccc  ctg  agt  gag  gac  gac  ttc  gat  atg  ttc  tat  gag  atc  tgg  gag        5591
Pro  Leu  Ser  Glu  Asp  Asp  Phe  Asp  Met  Phe  Tyr  Glu  Ile  Trp  Glu
1785                 1790                      1795 aaa  ttt  gac  cca  gag  gcc  act  cag  ttt  att  gag  tat  tcg  gtc  ctg        5636
Lys  Phe  Asp  Pro  Glu  Ala  Thr  Gln  Phe  Ile  Glu  Tyr  Ser  Val  Leu
1800                 1805                      1810 tct  gac  ttt  gcc  gat  gcc  ctg  tct  gag  cca  ctc  cgt  atc  gcc  aag        5681
Ser  Asp  Phe  Ala  Asp  Ala  Leu  Ser  Glu  Pro  Leu  Arg  Ile  Ala  Lys
1815                 1820                      1825 ccc  aac  cag  ata  agc  ctc  atc  aac  atg  gac  ctg  ccc  atg  gtg  agt        5726
Pro  Asn  Gln  Ile  Ser  Leu  Ile  Asn  Met  Asp  Leu  Pro  Met  Val  Ser
1830                 1835                      1840 ggg  gac  cgc  atc  cat  tgc  atg  gac  att  ctc  ttt  gcc  ttc  acc  aaa        5771
Gly  Asp  Arg  Ile  His  Cys  Met  Asp  Ile  Leu  Phe  Ala  Phe  Thr  Lys
1845                 1850                      1855 agg  gtc  ctg  ggg  gag  tct  ggg  gag  atg  gac  gcc  ctg  aag  atc  cag        5816
Arg  Val  Leu  Gly  Glu  Ser  Gly  Glu  Met  Asp  Ala  Leu  Lys  Ile  Gln
1860                 1865                      1870 atg  gag  gag  aag  ttc  atg  gca  gcc  aac  cca  tcc  aag  atc  tcc  tac        5861
Met  Glu  Glu  Lys  Phe  Met  Ala  Ala  Asn  Pro  Ser  Lys  Ile  Ser  Tyr
1875                 1880                      1885 gag  ccc  atc  acc  acc  aca  ctc  cgg  cgc  aag  cac  gaa  gag  gtg  tcg        5906
Glu  Pro  Ile  Thr  Thr  Thr  Leu  Arg  Arg  Lys  His  Glu  Glu  Val  Ser
1890                 1895                      1900 gcc  atg  gtt  atc  cag  aga  gcc  ttc  cgc  agg  cac  ctg  ctg  caa  cgc        5951
Ala  Met  Val  Ile  Gln  Arg  Ala  Phe  Arg  Arg  His  Leu  Leu  Gln  Arg
1905                 1910                      1915 tct  ttg  aag  cat  gcc  tcc  ttc  ctc  ttc  cgt  cag  cag  gcg  ggc  agc        5996
Ser  Leu  Lys  His  Ala  Ser  Phe  Leu  Phe  Arg  Gln  Gln  Ala  Gly  Ser
1920                 1925                      1930 ggc  ctc  tcc  gaa  gag  gat  gcc  cct  gag  cga  gag  ggc  ctc  atc  gcc        6041
Gly  Leu  Ser  Glu  Glu  Asp  Ala  Pro  Glu  Arg  Glu  Gly  Leu  Ile  Ala
1935                 1940                      1945 tac  gtg  atg  agt  gag  aac  ttc  tcc  cga  ccc  ctt  ggc  cca  ccc  tcc        6086
Tyr  Val  Met  Ser  Glu  Asn  Phe  Ser  Arg  Pro  Leu  Gly  Pro  Pro  Ser
1950                 1955                      1960 agc  tcc  tcc  atc  tcc  tcc  act  tcc  ttc  cca  ccc  tcc  tat  gac  agt        6131
Ser  Ser  Ser  Ile  Ser  Ser  Thr  Ser  Phe  Pro  Pro  Ser  Tyr  Asp  Ser
1965                 1970                      1975 gtc  act  aga  gcc  acc  agc  gat  aac  ctc  cag  gtg  cgg  ggg  tct  gac        6176
Val  Thr  Arg  Ala  Thr  Ser  Asp  Asn  Leu  Gln  Val  Arg  Gly  Ser  Asp
1980                 1985                      1990
```

```
tac agc cac agt gaa gat ctc gcc gac ttc ccc cct tct ccg gac    6221
Tyr Ser His Ser Glu Asp Leu Ala Asp Phe Pro Pro Ser Pro Asp
1995                2000                2005 agg gac cgt gag tcc atc gtg tga gcctcggcct ggctggccag           6265
Arg Asp Arg Glu Ser Ile Val
2010                2015 gacacactga aaagcagcct ttttcaccat ggcaaaccta atgcagtca gtcacaaacc    6325
agcctggggc cttcctggct ttgggagtaa gaaatgggcc tcagccccgc ggatcaacca    6385
ggcagagttc tgtggcgccg cgtggacagc cggagcagtt ggcctgtgct ggaggcctc    6445
agatagacct gtgacctggt ctggtcaggc aatgccctgc ggctctggaa agcaacttca    6505
tcccagctgc tgaggcgaaa tataaaactg agactgtata tgttgtgaat gggctttcat    6565
aaatttatta tatttgatat ttttttactt gagcaaagaa ctaaggattt ttccatggac    6625
atgggcagca attcacgctg tctcttctta accctgaaca agagtgtcta tggagcagcc    6685
ggaagtctgt tctcaaagca gaagtggaat ccagtgtggc tcccacaggt cttcactgcc    6745
caggggtcga atggggtccc cctcccactt gacctgagat gctgggaggg ctgaaccccc    6805
actcacacaa gcacacacac acagtcctca cacacggagg ccagacacag gccgtgggac    6865
ccaggctccc agcctaaggg agacaggcct ttccctgccg gcccccaag gatggggttc     6925
ttgtccacgg ggctcactct ggcccccat tgtctccaag gtcccatttt ccccctgtgt     6985
tttcacgcag gtcatattgt cagtcctaca aaaataaaag gcttccagag gagagtggcc    7045
tgggtcccag ggctggccct aggcactgat agttgccttt cttcccctc ctgtaagagt     7105
attaacaaaa ccaaaggaca caagggtgca agccccattc acggcctggc atgcagcttg    7165
tccttgctcc tggaacctgg caggccctgc ccagccagcc atcggaagag agggctgagc    7225
catgggggtt tggggctaag aagttcacca gccctgagcc atgcggcccc ctcagcctgc    7285
ctgaagagag gaaactggcg atctcccagg gctctctgga ccatacgcgg aggagttttc    7345
tgtgtggtct ccagctcctc tccagacaca gagacatggg agtggggagc ggagcttggc    7405
cctgcgccct gtgcagggaa agggatggtc aggcccagtt ctcgtgccct tagaggggaa    7465
tgaaccatgg cacctttgag agaggggca ctgtggtcag gcccagcctc tctggctcag    7525
cccgggatcc tgatggcacc cacacagagg acctctttgg ggcaagatcc aggtggtccc    7585
ataggtcttg tgaaaaggct ttttcaggga aaaatatttt actagtccaa tcaccccag    7645
gacctcttca gctgctgaca atcctattta gcatatgcaa atcttttaac atagagaact    7705
gtcaccctga ggtaacaggg tcaactgcg aagcctgagc aggcaggggc ttggctgccc    7765
cattccagct ctcccatgga gccctccac cgggcgcatg cctcccaggc cacctcagtc    7825
tcacctgccg gctctgggct ggctgctcct aacctacctc gccgagctgt cggagggctg    7885
gacatttgtg gcagtgctga agggggcatt gccggcgagt aaagtattat gtttcttctt    7945
gtcaccccag ttcccttggt ggcaacccca gacccaaccc atgcccctga cagatctagt    8005
tctcttctcc tgtgttccct ttgagtccag tgtgggacac ggtttaactg tcccagcgac    8065
atttctccaa gtgaaaatcc tatttttgta gatctccatg ctttgctctc aaggcttgga    8125
gaggtatgtg cccctcctgg gtgctcaccg cctgctacac aggcaggaat gcggttggga    8185
ggcaggtcgg gctgccagcc cagctggccg gaaggagact gtggttttg tgtgtgtgga    8245
cagcccggga gctttgagac aggtgcctgg ggctggctgc agacggtgtg gttggggtg    8305
ggaggtgagc tagacccaac ccttagcttt tagcctggct gtcacctttt taatttccag    8365
aactgcacaa tgaccagcag gagggaagga cagacatcaa gtgccagatg ttgtctgaac    8425
```
taatcgagca cttctcacca aacttcatgt ataaataaaa tacatatttt taaaacaaac    8485
caataaatgg cttacatga    8504

<210> SEQ ID NO 11
<211> LENGTH: 2016
<212> TYPE: PRT
<213> ORGANISM: Homo sapiens

<400> SEQUENCE: 11

Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Val Ser Glu
        195                 200                 205

Asn Ile Lys Leu Gly Asn Leu Ser Ala Leu Arg Thr Phe Arg Val Leu
    210                 215                 220

Arg Ala Leu Lys Thr Ile Ser Val Ile Pro Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

-continued

```
Met Thr Gln Asp Cys Trp Glu Arg Leu Tyr Gln Gln Thr Leu Arg Ser
    370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
            420                 425                 430

Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
    450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Arg Asp Leu Gly Ser Glu Ala Asp Phe Ala
    530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
    610                 615                 620

Glu His Pro Pro Asp Thr Thr Thr Pro Ser Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
```

-continued

```
            785                 790                 795                 800
Met Ser Asn Leu Ser Val Leu Arg Ser Phe Arg Leu Leu Arg Val Phe
                    805                 810                 815
Lys Leu Ala Lys Ser Trp Pro Thr Leu Asn Thr Leu Ile Lys Ile Ile
                    820                 825                 830
Gly Asn Ser Val Gly Ala Leu Gly Asn Leu Thr Leu Val Leu Ala Ile
                    835                 840                 845
Ile Val Phe Ile Phe Ala Val Val Gly Met Gln Leu Phe Gly Lys Asn
        850                 855                 860
Tyr Ser Glu Leu Arg Asp Ser Asp Ser Gly Leu Leu Pro Arg Trp His
865                 870                 875                 880
Met Met Asp Phe Phe His Ala Phe Leu Ile Ile Phe Arg Ile Leu Cys
                    885                 890                 895
Gly Glu Trp Ile Glu Thr Met Trp Asp Cys Met Glu Val Ser Gly Gln
                    900                 905                 910
Ser Leu Cys Leu Leu Val Phe Leu Leu Val Met Val Ile Gly Asn Leu
                    915                 920                 925
Val Val Leu Asn Leu Phe Leu Ala Leu Leu Ser Ser Phe Ser Ala
        930                 935                 940
Asp Asn Leu Thr Ala Pro Asp Glu Asp Arg Glu Met Asn Asn Leu Gln
945                 950                 955                 960
Leu Ala Leu Ala Arg Ile Gln Arg Gly Leu Arg Phe Val Lys Arg Thr
                    965                 970                 975
Thr Trp Asp Phe Cys Cys Gly Leu Leu Arg Gln Arg Pro Gln Lys Pro
                    980                 985                 990
Ala Ala Leu Ala Ala Gln Gly Gln Leu Pro Ser Cys Ile Ala Thr Pro
                    995                 1000                1005
Tyr Ser Pro Pro Pro Pro Glu Thr Glu Lys Val Pro Pro Thr Arg
    1010                1015                1020
Lys Glu Thr Arg Phe Glu Glu Gly Glu Gln Pro Gly Gln Gly Thr
    1025                1030                1035
Pro Gly Asp Pro Glu Pro Val Cys Val Pro Ile Ala Val Ala Glu
    1040                1045                1050
Ser Asp Thr Asp Asp Gln Glu Glu Asp Glu Glu Asn Ser Leu Gly
    1055                1060                1065
Thr Glu Glu Glu Ser Ser Lys Gln Gln Glu Ser Gln Pro Val Ser
    1070                1075                1080
Gly Gly Pro Glu Ala Pro Pro Asp Ser Arg Thr Trp Ser Gln Val
    1085                1090                1095
Ser Ala Thr Ala Ser Ser Glu Ala Glu Ala Ser Ala Ser Gln Ala
    1100                1105                1110
Asp Trp Arg Gln Gln Trp Lys Ala Glu Pro Gln Ala Pro Gly Cys
    1115                1120                1125
Gly Glu Thr Pro Glu Asp Ser Cys Ser Glu Gly Ser Thr Ala Asp
    1130                1135                1140
Met Thr Asn Thr Ala Glu Leu Leu Glu Gln Ile Pro Asp Leu Gly
    1145                1150                1155
Gln Asp Val Lys Asp Pro Glu Asp Cys Phe Thr Glu Gly Cys Val
    1160                1165                1170
Arg Arg Cys Pro Cys Cys Ala Val Asp Thr Thr Gln Ala Pro Gly
    1175                1180                1185
Lys Val Trp Trp Arg Leu Arg Lys Thr Cys Tyr His Ile Val Glu
    1190                1195                1200
```

```
-continued

His Ser Trp Phe Glu Thr Phe Ile Ile Phe Met Ile Leu Leu Ser
1205                    1210                1215

Ser Gly Ala Leu Ala Phe Glu Asp Ile Tyr Leu Glu Arg Lys
1220                    1225                1230

Thr Ile Lys Val Leu Leu Glu Tyr Ala Asp Lys Met Phe Thr Tyr
1235                    1240                1245

Val Phe Val Leu Glu Met Leu Leu Lys Trp Val Ala Tyr Gly Phe
1250                    1255                1260

Lys Lys Tyr Phe Thr Asn Ala Trp Cys Trp Leu Asp Phe Leu Ile
1265                    1270                1275

Val Asp Val Ser Leu Val Ser Leu Val Ala Asn Thr Leu Gly Phe
1280                    1285                1290

Ala Glu Met Gly Pro Ile Lys Ser Leu Arg Thr Leu Arg Ala Leu
1295                    1300                1305

Arg Pro Leu Arg Ala Leu Ser Arg Phe Glu Gly Met Arg Val Val
1310                    1315                1320

Val Asn Ala Leu Val Gly Ala Ile Pro Ser Ile Met Asn Val Leu
1325                    1330                1335

Leu Val Cys Leu Ile Phe Trp Leu Ile Phe Ser Ile Met Gly Val
1340                    1345                1350

Asn Leu Phe Ala Gly Lys Phe Gly Arg Cys Ile Asn Gln Thr Glu
1355                    1360                1365

Gly Asp Leu Pro Leu Asn Tyr Thr Ile Val Asn Asn Lys Ser Gln
1370                    1375                1380

Cys Glu Ser Leu Asn Leu Thr Gly Glu Leu Tyr Trp Thr Lys Val
1385                    1390                1395

Lys Val Asn Phe Asp Asn Val Gly Ala Gly Tyr Leu Ala Leu Leu
1400                    1405                1410

Gln Val Ala Thr Phe Lys Gly Trp Met Asp Ile Met Tyr Ala Ala
1415                    1420                1425

Val Asp Ser Arg Gly Tyr Glu Glu Gln Pro Gln Trp Glu Tyr Asn
1430                    1435                1440

Leu Tyr Met Tyr Ile Tyr Phe Val Ile Phe Ile Ile Phe Gly Ser
1445                    1450                1455

Phe Phe Thr Leu Asn Leu Phe Ile Gly Val Ile Ile Asp Asn Phe
1460                    1465                1470

Asn Gln Gln Lys Lys Lys Leu Gly Gly Gln Asp Ile Phe Met Thr
1475                    1480                1485

Glu Glu Gln Lys Lys Tyr Tyr Asn Ala Met Lys Lys Leu Gly Ser
1490                    1495                1500

Lys Lys Pro Gln Lys Pro Ile Pro Arg Pro Leu Asn Lys Tyr Gln
1505                    1510                1515

Gly Phe Ile Phe Asp Ile Val Thr Lys Gln Ala Phe Asp Val Thr
1520                    1525                1530

Ile Met Phe Leu Ile Cys Leu Asn Met Val Thr Met Met Val Glu
1535                    1540                1545

Thr Asp Asp Gln Ser Pro Glu Lys Ile Asn Ile Leu Ala Lys Ile
1550                    1555                1560

Asn Leu Leu Phe Val Ala Ile Phe Thr Gly Glu Cys Ile Val Lys
1565                    1570                1575

Leu Ala Ala Leu Arg His Tyr Tyr Phe Thr Asn Ser Trp Asn Ile
1580                    1585                1590

Phe Asp Phe Val Val Val Ile Leu Ser Ile Val Gly Thr Val Leu
1595                    1600                1605
```

```
Ser Asp Ile Ile Gln Lys Tyr Phe Phe Ser Pro Thr Leu Phe Arg
    1610            1615                1620

Val Ile Arg Leu Ala Arg Ile Gly Arg Ile Leu Arg Leu Ile Arg
    1625            1630                1635

Gly Ala Lys Gly Ile Arg Thr Leu Leu Phe Ala Leu Met Met Ser
    1640            1645                1650

Leu Pro Ala Leu Phe Asn Ile Gly Leu Leu Leu Phe Leu Val Met
    1655            1660                1665

Phe Ile Tyr Ser Ile Phe Gly Met Ala Asn Phe Ala Tyr Val Lys
    1670            1675                1680

Trp Glu Ala Gly Ile Asp Asp Met Phe Asn Phe Gln Thr Phe Ala
    1685            1690                1695

Asn Ser Met Leu Cys Leu Phe Gln Ile Thr Thr Ser Ala Gly Trp
    1700            1705                1710

Asp Gly Leu Leu Ser Pro Ile Leu Asn Thr Gly Pro Pro Tyr Cys
    1715            1720                1725

Asp Pro Thr Leu Pro Asn Ser Asn Gly Ser Arg Gly Asp Cys Gly
    1730            1735                1740

Ser Pro Ala Val Gly Ile Leu Phe Phe Thr Thr Tyr Ile Ile Ile
    1745            1750                1755

Ser Phe Leu Ile Val Val Asn Met Tyr Ile Ala Ile Ile Leu Glu
    1760            1765                1770

Asn Phe Ser Val Ala Thr Glu Glu Ser Thr Glu Pro Leu Ser Glu
    1775            1780                1785

Asp Asp Phe Asp Met Phe Tyr Glu Ile Trp Glu Lys Phe Asp Pro
    1790            1795                1800

Glu Ala Thr Gln Phe Ile Glu Tyr Ser Val Leu Ser Asp Phe Ala
    1805            1810                1815

Asp Ala Leu Ser Glu Pro Leu Arg Ile Ala Lys Pro Asn Gln Ile
    1820            1825                1830

Ser Leu Ile Asn Met Asp Leu Pro Met Val Ser Gly Asp Arg Ile
    1835            1840                1845

His Cys Met Asp Ile Leu Phe Ala Phe Thr Lys Arg Val Leu Gly
    1850            1855                1860

Glu Ser Gly Glu Met Asp Ala Leu Lys Ile Gln Met Glu Glu Lys
    1865            1870                1875

Phe Met Ala Ala Asn Pro Ser Lys Ile Ser Tyr Glu Pro Ile Thr
    1880            1885                1890

Thr Thr Leu Arg Arg Lys His Glu Glu Val Ser Ala Met Val Ile
    1895            1900                1905

Gln Arg Ala Phe Arg Arg His Leu Leu Gln Arg Ser Leu Lys His
    1910            1915                1920

Ala Ser Phe Leu Phe Arg Gln Gln Ala Gly Ser Gly Leu Ser Glu
    1925            1930                1935

Glu Asp Ala Pro Glu Arg Glu Gly Leu Ile Ala Tyr Val Met Ser
    1940            1945                1950

Glu Asn Phe Ser Arg Pro Leu Gly Pro Pro Ser Ser Ser Ser Ile
    1955            1960                1965

Ser Ser Thr Ser Phe Pro Pro Ser Tyr Asp Ser Val Thr Arg Ala
    1970            1975                1980

Thr Ser Asp Asn Leu Gln Val Arg Gly Ser Asp Tyr Ser His Ser
    1985            1990                1995

Glu Asp Leu Ala Asp Phe Pro Pro Ser Pro Asp Arg Asp Arg Glu
```

```
                     2000            2005            2010
Ser Ile Val
    2015

<210> SEQ ID NO 12
<211> LENGTH: 8450
<212> TYPE: DNA
<213> ORGANISM: Homo sapiens
<220> FEATURE:
<221> NAME/KEY: CDS
<222> LOCATION: (195)..(6191)

<400> SEQUENCE: 12
agacggcggc ggcgcccgta ggatgcaggg atcgctcccc cggggccgct gagcctgcgc      60
ccagtgcccc gagcccgcg ccgagccgag tccgcgccaa gcagcagccg cccacccccgg    120 ggcccggccg ggggaccagc agcttcccca caggcaacgt gaggagagcc tgtgcccaga    180
agcaggatga gaag atg gca aac ttc cta tta cct cgg ggc acc agc agc      230
              Met Ala Asn Phe Leu Leu Pro Arg Gly Thr Ser Ser
                1               5                  10 ttc cgc agg ttc aca cgg gag tcc ctg gca gcc atc gag aag cgc atg      278
Phe Arg Arg Phe Thr Arg Glu Ser Leu Ala Ala Ile Glu Lys Arg Met
         15                  20                  25 gca gag aag caa gcc cgc ggc tca acc acc ttg cag gag agc cga gag      326
Ala Glu Lys Gln Ala Arg Gly Ser Thr Thr Leu Gln Glu Ser Arg Glu
 30                  35                  40 ggg ctg ccc gag gag gag gct ccc cgg ccc cag ctg gac ctg cag gcc      374
Gly Leu Pro Glu Glu Glu Ala Pro Arg Pro Gln Leu Asp Leu Gln Ala
 45                  50                  55                  60 tcc aaa aag ctg cca gat ctc tat ggc aat cca ccc caa gag ctc atc      422
Ser Lys Lys Leu Pro Asp Leu Tyr Gly Asn Pro Pro Gln Glu Leu Ile
                 65                  70                  75 gga gag ccc ctg gag gac ctg gac ccc ttc tat agc acc caa aag act      470
Gly Glu Pro Leu Glu Asp Leu Asp Pro Phe Tyr Ser Thr Gln Lys Thr
             80                  85                  90 ttc atc gta ctg aat aaa ggc aag acc atc ttc cgg ttc agt gcc acc      518
Phe Ile Val Leu Asn Lys Gly Lys Thr Ile Phe Arg Phe Ser Ala Thr
         95                 100                 105 aac gcc ttg tat gtc ctc agt ccc ttc cac ccc atc cgg aga gcg gct      566
Asn Ala Leu Tyr Val Leu Ser Pro Phe His Pro Ile Arg Arg Ala Ala
110                 115                 120 gtg aag att ctg gtt cac tcg ctc ttc aac atg ctc atc atg tgc acc      614
Val Lys Ile Leu Val His Ser Leu Phe Asn Met Leu Ile Met Cys Thr
125                 130                 135                 140 atc ctc acc aac tgc gtg ttc atg gcc cag cac gac cct cca ccc tgg      662
Ile Leu Thr Asn Cys Val Phe Met Ala Gln His Asp Pro Pro Pro Trp
                145                 150                 155 acc aag tat gtc gag tac acc ttc acc gcc att tac acc ttt gag tct      710
Thr Lys Tyr Val Glu Tyr Thr Phe Thr Ala Ile Tyr Thr Phe Glu Ser
            160                 165                 170 ctg gtc aag att ctg gct cga ggc ttc tgc ctg cac gcg ttc act ttc      758
Leu Val Lys Ile Leu Ala Arg Gly Phe Cys Leu His Ala Phe Thr Phe
        175                 180                 185 ctt cgg gac cca tgg aac tgg ctg gac ttt agt gtg att atc atg gcg      806
Leu Arg Asp Pro Trp Asn Trp Leu Asp Phe Ser Val Ile Ile Met Ala
    190                 195                 200 tat gta tca gaa aat ata aaa cta ggc aat ttg tcg gct ctt cga act      854
Tyr Val Ser Glu Asn Ile Lys Leu Gly Asn Leu Ser Ala Leu Arg Thr
205                 210                 215                 220 ttc aga gtc ctg aga gct cta aaa act att tca gtt atc cca ggg ctg      902
Phe Arg Val Leu Arg Ala Leu Lys Thr Ile Ser Val Ile Pro Gly Leu
```

-continued

```
                  225                 230                 235
aag acc atc gtg ggg gcc ctg atc cag tct gtg aag aag ctg gct gat    950
Lys Thr Ile Val Gly Ala Leu Ile Gln Ser Val Lys Lys Leu Ala Asp
            240                 245                 250 gtg atg gtc ctc aca gtc ttc tgc ctc agc gtc ttt gcc ctc atc ggc    998
Val Met Val Leu Thr Val Phe Cys Leu Ser Val Phe Ala Leu Ile Gly
        255                 260                 265 ctg cag ctc ttc atg ggc aac cta agg cac aag tgc gtg cgc aac ttc   1046
Leu Gln Leu Phe Met Gly Asn Leu Arg His Lys Cys Val Arg Asn Phe
    270                 275                 280 aca gcg ctc aac ggc acc aac ggc tcc gtg gag gcc gac ggc ttg gtc   1094
Thr Ala Leu Asn Gly Thr Asn Gly Ser Val Glu Ala Asp Gly Leu Val
285                 290                 295                 300 tgg gaa tcc ctg gac ctt tac ctc agt gat cca gaa aat tac ctg ctc   1142
Trp Glu Ser Leu Asp Leu Tyr Leu Ser Asp Pro Glu Asn Tyr Leu Leu
                305                 310                 315 aag aac ggc acc tct gat gtg tta ctg tgt ggg aac agc tct gac gct   1190
Lys Asn Gly Thr Ser Asp Val Leu Leu Cys Gly Asn Ser Ser Asp Ala
            320                 325                 330 ggg aca tgt ccg gag ggc tac cgg tgc cta aag gca ggc gag aac ccc   1238
Gly Thr Cys Pro Glu Gly Tyr Arg Cys Leu Lys Ala Gly Glu Asn Pro
        335                 340                 345 gac cac ggc tac acc agc ttc gat tcc ttt gcc tgg gcc ttt ctt gca   1286
Asp His Gly Tyr Thr Ser Phe Asp Ser Phe Ala Trp Ala Phe Leu Ala
    350                 355                 360 ctc ttc cgc ctg atg acg cag gac tgc tgg gag cgc ctc tat cag cag   1334
Leu Phe Arg Leu Met Thr Gln Asp Cys Trp Glu Arg Leu Tyr Gln Gln
365                 370                 375                 380 acc ctc agg tcc gca ggg aag atc tac atg atc ttc ttc atg ctt gtc   1382
Thr Leu Arg Ser Ala Gly Lys Ile Tyr Met Ile Phe Phe Met Leu Val
                385                 390                 395 atc ttc ctg ggg tcc ttc tac ctg gtg aac ctg atc ctg gcc gtg gtc   1430
Ile Phe Leu Gly Ser Phe Tyr Leu Val Asn Leu Ile Leu Ala Val Val
            400                 405                 410 gca atg gcc tat gag gag caa aac caa gcc acc atc gct gag acc gag   1478
Ala Met Ala Tyr Glu Glu Gln Asn Gln Ala Thr Ile Ala Glu Thr Glu
        415                 420                 425 gag aag gaa aag cgc ttc cag gag gcc atg gaa atg ctc aaa aaa gaa   1526
Glu Lys Glu Lys Arg Phe Gln Glu Ala Met Glu Met Leu Lys Lys Glu
    430                 435                 440 cac gag gcc ctc acc atc agg ggt gtg gat acc gtg tcc cgt agc tcc   1574
His Glu Ala Leu Thr Ile Arg Gly Val Asp Thr Val Ser Arg Ser Ser
445                 450                 455                 460 ttg gag atg tcc cct ttg gcc cca gta aac agc cat gag aga aga agc   1622
Leu Glu Met Ser Pro Leu Ala Pro Val Asn Ser His Glu Arg Arg Ser
                465                 470                 475 aag agg aga aaa cgg atg tct tca gga act gag gag tgt ggg gag gac   1670
Lys Arg Arg Lys Arg Met Ser Ser Gly Thr Glu Glu Cys Gly Glu Asp
            480                 485                 490 agg ctc ccc aag tct gac tca gaa gat ggt ccc aga gca atg aat cat   1718
Arg Leu Pro Lys Ser Asp Ser Glu Asp Gly Pro Arg Ala Met Asn His
        495                 500                 505 ctc agc ctc acc cgt ggc ctc agc agg act tct atg aag cca cgt tcc   1766
Leu Ser Leu Thr Arg Gly Leu Ser Arg Thr Ser Met Lys Pro Arg Ser
    510                 515                 520 agc cgc ggg agc att ttc acc ttt cgc agg cga gac ctg ggt tct gaa   1814
Ser Arg Gly Ser Ile Phe Thr Phe Arg Arg Arg Asp Leu Gly Ser Glu
525                 530                 535                 540 gca gat ttt gca gat gat gaa aac agc aca gcg ggg gag agc gag agc   1862
Ala Asp Phe Ala Asp Asp Glu Asn Ser Thr Ala Gly Glu Ser Glu Ser
```

|     |     |     |     |     |     |     |     |     |     |     |     |     |     |     |     |      |
|---|---|---|---|---|---|---|---|---|---|---|---|---|---|---|---|---|
|     |     |     | 545 |     |     |     | 550 |     |     |     | 555 |     |     |     |     |      |
| cac | cac | aca | tca | ctg | ctg | gtg | ccc | tgg | ccc | ctg | cgc | cgg | acc | agt | gcc | 1910 |
| His | His | Thr | Ser | Leu | Leu | Val | Pro | Trp | Pro | Leu | Arg | Arg | Thr | Ser | Ala |      |
|     |     |     | 560 |     |     |     | 565 |     |     |     | 570 |     |     |     |     |      |
| cag | gga | cag | ccc | agt | ccc | gga | acc | tcg | gct | cct | ggc | cac | gcc | ctc | cat | 1958 |
| Gln | Gly | Gln | Pro | Ser | Pro | Gly | Thr | Ser | Ala | Pro | Gly | His | Ala | Leu | His |      |
|     |     |     | 575 |     |     |     | 580 |     |     |     | 585 |     |     |     |     |      |
| ggc | aaa | aag | aac | agc | act | gtg | gac | tgc | aat | ggg | gtg | gtc | tca | tta | ctg | 2006 |
| Gly | Lys | Lys | Asn | Ser | Thr | Val | Asp | Cys | Asn | Gly | Val | Val | Ser | Leu | Leu |      |
|     |     |     | 590 |     |     |     | 595 |     |     |     | 600 |     |     |     |     |      |
| ggg | gca | ggc | gac | cca | gag | gcc | aca | tcc | cca | gga | agc | cac | ctc | ctc | cgc | 2054 |
| Gly | Ala | Gly | Asp | Pro | Glu | Ala | Thr | Ser | Pro | Gly | Ser | His | Leu | Leu | Arg |      |
| 605 |     |     |     |     | 610 |     |     |     |     | 615 |     |     |     |     | 620 |      |
| cct | gtg | atg | cta | gag | cac | ccg | cca | gac | acg | acc | acg | cca | tcg | gag | gag | 2102 |
| Pro | Val | Met | Leu | Glu | His | Pro | Pro | Asp | Thr | Thr | Thr | Pro | Ser | Glu | Glu |      |
|     |     |     |     |     | 625 |     |     |     |     | 630 |     |     |     |     | 635 |      |
| cca | ggc | ggg | ccc | cag | atg | ctg | acc | tcc | cag | gct | ccg | tgt | gta | gat | ggc | 2150 |
| Pro | Gly | Gly | Pro | Gln | Met | Leu | Thr | Ser | Gln | Ala | Pro | Cys | Val | Asp | Gly |      |
|     |     |     | 640 |     |     |     | 645 |     |     |     | 650 |     |     |     |     |      |
| ttc | gag | gag | cca | gga | gca | cgg | cag | cgg | gcc | ctc | agc | gca | gtc | agc | gtc | 2198 |
| Phe | Glu | Glu | Pro | Gly | Ala | Arg | Gln | Arg | Ala | Leu | Ser | Ala | Val | Ser | Val |      |
|     |     |     | 655 |     |     |     | 660 |     |     |     | 665 |     |     |     |     |      |
| ctc | acc | agc | gca | ctg | gaa | gag | tta | gag | gag | tct | cgc | cac | aag | tgt | cca | 2246 |
| Leu | Thr | Ser | Ala | Leu | Glu | Glu | Leu | Glu | Glu | Ser | Arg | His | Lys | Cys | Pro |      |
|     |     |     | 670 |     |     |     | 675 |     |     |     | 680 |     |     |     |     |      |
| cca | tgc | tgg | aac | cgt | ctc | gcc | cag | cgc | tac | ctg | atc | tgg | gag | tgc | tgc | 2294 |
| Pro | Cys | Trp | Asn | Arg | Leu | Ala | Gln | Arg | Tyr | Leu | Ile | Trp | Glu | Cys | Cys |      |
| 685 |     |     |     |     | 690 |     |     |     |     | 695 |     |     |     |     | 700 |      |
| ccg | ctg | tgg | atg | tcc | atc | aag | cag | gga | gtg | aag | ttg | gtg | gtc | atg | gac | 2342 |
| Pro | Leu | Trp | Met | Ser | Ile | Lys | Gln | Gly | Val | Lys | Leu | Val | Val | Met | Asp |      |
|     |     |     |     |     | 705 |     |     |     |     | 710 |     |     |     |     | 715 |      |
| ccg | ttt | act | gac | ctc | acc | atc | act | atg | tgc | atc | gta | ctc | aac | aca | ctc | 2390 |
| Pro | Phe | Thr | Asp | Leu | Thr | Ile | Thr | Met | Cys | Ile | Val | Leu | Asn | Thr | Leu |      |
|     |     |     | 720 |     |     |     | 725 |     |     |     | 730 |     |     |     |     |      |
| ttc | atg | gcg | ctg | gag | cac | tac | aac | atg | aca | agt | gaa | ttc | gag | gag | atg | 2438 |
| Phe | Met | Ala | Leu | Glu | His | Tyr | Asn | Met | Thr | Ser | Glu | Phe | Glu | Glu | Met |      |
|     |     |     | 735 |     |     |     | 740 |     |     |     | 745 |     |     |     |     |      |
| ctg | cag | gtc | gga | aac | ctg | gtc | ttc | aca | ggg | att | ttc | aca | gca | gag | atg | 2486 |
| Leu | Gln | Val | Gly | Asn | Leu | Val | Phe | Thr | Gly | Ile | Phe | Thr | Ala | Glu | Met |      |
|     |     |     | 750 |     |     |     | 755 |     |     |     | 760 |     |     |     |     |      |
| acc | ttc | aag | atc | att | gcc | ctc | gac | ccc | tac | tac | tac | ttc | caa | cag | ggc | 2534 |
| Thr | Phe | Lys | Ile | Ile | Ala | Leu | Asp | Pro | Tyr | Tyr | Tyr | Phe | Gln | Gln | Gly |      |
| 765 |     |     |     |     | 770 |     |     |     |     | 775 |     |     |     |     | 780 |      |
| tgg | aac | atc | ttc | gac | agc | atc | atc | gtc | atc | ctt | agc | ctc | atg | gag | ctg | 2582 |
| Trp | Asn | Ile | Phe | Asp | Ser | Ile | Ile | Val | Ile | Leu | Ser | Leu | Met | Glu | Leu |      |
|     |     |     |     |     | 785 |     |     |     |     | 790 |     |     |     |     | 795 |      |
| ggc | ctg | tcc | cgc | atg | agc | aac | ttg | tcg | gtg | ctg | cgc | tcc | ttc | cgc | ctg | 2630 |
| Gly | Leu | Ser | Arg | Met | Ser | Asn | Leu | Ser | Val | Leu | Arg | Ser | Phe | Arg | Leu |      |
|     |     |     | 800 |     |     |     | 805 |     |     |     | 810 |     |     |     |     |      |
| ctg | cgg | gtc | ttc | aag | ctg | gcc | aaa | tca | tgg | ccc | acc | ctg | aac | aca | ctc | 2678 |
| Leu | Arg | Val | Phe | Lys | Leu | Ala | Lys | Ser | Trp | Pro | Thr | Leu | Asn | Thr | Leu |      |
|     |     |     | 815 |     |     |     | 820 |     |     |     | 825 |     |     |     |     |      |
| atc | aag | atc | atc | ggg | aac | tca | gtg | ggg | gca | ctg | ggg | aac | ctg | aca | ctg | 2726 |
| Ile | Lys | Ile | Ile | Gly | Asn | Ser | Val | Gly | Ala | Leu | Gly | Asn | Leu | Thr | Leu |      |
|     |     |     | 830 |     |     |     | 835 |     |     |     | 840 |     |     |     |     |      |
| gtg | cta | gcc | atc | atc | gtg | ttc | atc | ttt | gct | gtg | gtg | ggc | atg | cag | ctc | 2774 |
| Val | Leu | Ala | Ile | Ile | Val | Phe | Ile | Phe | Ala | Val | Val | Gly | Met | Gln | Leu |      |
| 845 |     |     |     |     | 850 |     |     |     |     | 855 |     |     |     |     | 860 |      |
| ttt | ggc | aag | aac | tac | tcg | gag | ctg | agg | gac | agc | gac | tca | ggc | ctg | ctg | 2822 |
| Phe | Gly | Lys | Asn | Tyr | Ser | Glu | Leu | Arg | Asp | Ser | Asp | Ser | Gly | Leu | Leu |      |

-continued

```
                865                 870                 875
cct cgc tgg cac atg atg gac ttc ttt cat gcc ttc ctc atc atc ttc    2870
Pro Arg Trp His Met Met Asp Phe Phe His Ala Phe Leu Ile Ile Phe
            880                 885                 890 cgc atc ctc tgt gga gag tgg atc gag acc atg tgg gac tgc atg gag    2918
Arg Ile Leu Cys Gly Glu Trp Ile Glu Thr Met Trp Asp Cys Met Glu
                895                 900                 905 gtg tcg ggg cag tca tta tgc ctg ctg gtc ttc ttg ctt gtt atg gtc    2966
Val Ser Gly Gln Ser Leu Cys Leu Leu Val Phe Leu Leu Val Met Val
            910                 915                 920 att ggc aac ctt gtg gtc ctg aat ctc ttc ctg gcc ttg ctc ctc agc    3014
Ile Gly Asn Leu Val Val Leu Asn Leu Phe Leu Ala Leu Leu Leu Ser
925                 930                 935                 940 tcc ttc agt gca gac aac ctc aca gcc cct gat gag gac aga gag atg    3062
Ser Phe Ser Ala Asp Asn Leu Thr Ala Pro Asp Glu Asp Arg Glu Met
                945                 950                 955 aac aac ctc cag ctg gcc ctg gcc cgc atc cag agg ggc ctg cgc ttt    3110
Asn Asn Leu Gln Leu Ala Leu Ala Arg Ile Gln Arg Gly Leu Arg Phe
            960                 965                 970 gtc aag cgg acc acc tgg gat ttc tgc tgt ggt ctc ctg cgg cag cgg    3158
Val Lys Arg Thr Thr Trp Asp Phe Cys Cys Gly Leu Leu Arg Gln Arg
                975                 980                 985 cct cag aag ccc gca gcc ctt gcc gcc cag ggc cag ctg ccc agc tgc    3206
Pro Gln Lys Pro Ala Ala Leu Ala Ala Gln Gly Gln Leu Pro Ser Cys
            990                 995                 1000 att gcc acc ccc tac tcc ccg cca ccc cca gag acg gag aag gtg        3251
Ile Ala Thr Pro Tyr Ser Pro Pro Pro Pro Glu Thr Glu Lys Val
1005                1010                1015 cct ccc acc cgc aag gaa aca cgg ttt gag gaa ggc gag caa cca        3296
Pro Pro Thr Arg Lys Glu Thr Arg Phe Glu Glu Gly Glu Gln Pro
1020                1025                1030 ggc cag ggc acc ccc ggg gat cca gag ccc gtg tgt gtg ccc atc        3341
Gly Gln Gly Thr Pro Gly Asp Pro Glu Pro Val Cys Val Pro Ile
1035                1040                1045 gct gtg gcc gag tca gac aca gat gac caa gaa gaa gat gag gag        3386
Ala Val Ala Glu Ser Asp Thr Asp Asp Gln Glu Glu Asp Glu Glu
1050                1055                1060 aac agc ctg ggc acg gag gag gag tcc agc aag cag cag gaa tcc        3431
Asn Ser Leu Gly Thr Glu Glu Glu Ser Ser Lys Gln Gln Glu Ser
1065                1070                1075 cag cct gtg tcc ggt ggc cca gag gcc cct ccg gat tcc agg acc        3476
Gln Pro Val Ser Gly Gly Pro Glu Ala Pro Pro Asp Ser Arg Thr
1080                1085                1090 tgg agc cag gtg tca gcg act gcc tcc tct gag gcc gag gcc agt        3521
Trp Ser Gln Val Ser Ala Thr Ala Ser Ser Glu Ala Glu Ala Ser
1095                1100                1105 gca tct cag gcc gac tgg cgg cag cag tgg aaa gcg gaa ccc cag        3566
Ala Ser Gln Ala Asp Trp Arg Gln Gln Trp Lys Ala Glu Pro Gln
1110                1115                1120 gcc cca ggg tgc ggt gag acc cca gag gac agt tgc tcc gag ggc        3611
Ala Pro Gly Cys Gly Glu Thr Pro Glu Asp Ser Cys Ser Glu Gly
1125                1130                1135 agc aca gca gac atg acc aac acc gct gag ctc ctg gag cag atc        3656
Ser Thr Ala Asp Met Thr Asn Thr Ala Glu Leu Leu Glu Gln Ile
1140                1145                1150 cct gac ctc ggc cag gat gtc aag gac cca gag gac tgc ttc act        3701
Pro Asp Leu Gly Gln Asp Val Lys Asp Pro Glu Asp Cys Phe Thr
1155                1160                1165 gaa ggc tgt gtc cgg cgc tgt ccc tgc tgt gcg gtg gac acc aca        3746
Glu Gly Cys Val Arg Arg Cys Pro Cys Cys Ala Val Asp Thr Thr
```

-continued

| | | |
|---|---|---|
| 1170 | 1175 | 1180 |

| cag | gcc | cca | ggg | aag | gtc | tgg | tgg | cgg | ttg | cgc | aag | acc | tgc | tac | 3791 |
|---|---|---|---|---|---|---|---|---|---|---|---|---|---|---|---|
| Gln | Ala | Pro | Gly | Lys | Val | Trp | Trp | Arg | Leu | Arg | Lys | Thr | Cys | Tyr | |
| 1185 | | | 1190 | | | | | 1195 | | | | | | | |

| cac | atc | gtg | gag | cac | agc | tgg | ttc | gag | aca | ttc | atc | atc | ttc | atg | 3836 |
|---|---|---|---|---|---|---|---|---|---|---|---|---|---|---|---|
| His | Ile | Val | Glu | His | Ser | Trp | Phe | Glu | Thr | Phe | Ile | Ile | Phe | Met | |
| 1200 | | | | 1205 | | | | | 1210 | | | | | | |

| atc | cta | ctc | agc | agt | gga | gcg | ctg | gcc | ttc | gag | gac | atc | tac | cta | 3881 |
|---|---|---|---|---|---|---|---|---|---|---|---|---|---|---|---|
| Ile | Leu | Leu | Ser | Ser | Gly | Ala | Leu | Ala | Phe | Glu | Asp | Ile | Tyr | Leu | |
| 1215 | | | | | 1220 | | | | | 1225 | | | | | |

| gag | gag | cgg | aag | acc | atc | aag | gtt | ctg | ctt | gag | tat | gcc | gac | aag | 3926 |
|---|---|---|---|---|---|---|---|---|---|---|---|---|---|---|---|
| Glu | Glu | Arg | Lys | Thr | Ile | Lys | Val | Leu | Leu | Glu | Tyr | Ala | Asp | Lys | |
| 1230 | | | | | 1235 | | | | | 1240 | | | | | |

| atg | ttc | aca | tat | gtc | ttc | gtg | ctg | gag | atg | ctg | ctc | aag | tgg | gtg | 3971 |
|---|---|---|---|---|---|---|---|---|---|---|---|---|---|---|---|
| Met | Phe | Thr | Tyr | Val | Phe | Val | Leu | Glu | Met | Leu | Leu | Lys | Trp | Val | |
| 1245 | | | | | 1250 | | | | | 1255 | | | | | |

| gcc | tac | ggc | ttc | aag | aag | tac | ttc | acc | aat | gcc | tgg | tgc | tgg | ctc | 4016 |
|---|---|---|---|---|---|---|---|---|---|---|---|---|---|---|---|
| Ala | Tyr | Gly | Phe | Lys | Lys | Tyr | Phe | Thr | Asn | Ala | Trp | Cys | Trp | Leu | |
| 1260 | | | | | 1265 | | | | | 1270 | | | | | |

| gac | ttc | ctc | atc | gta | gac | gtc | tct | ctg | gtc | agc | ctg | gtg | gcc | aac | 4061 |
|---|---|---|---|---|---|---|---|---|---|---|---|---|---|---|---|
| Asp | Phe | Leu | Ile | Val | Asp | Val | Ser | Leu | Val | Ser | Leu | Val | Ala | Asn | |
| 1275 | | | | | 1280 | | | | | 1285 | | | | | |

| acc | ctg | ggc | ttt | gcc | gag | atg | ggc | ccc | atc | aag | tca | ctg | cgg | acg | 4106 |
|---|---|---|---|---|---|---|---|---|---|---|---|---|---|---|---|
| Thr | Leu | Gly | Phe | Ala | Glu | Met | Gly | Pro | Ile | Lys | Ser | Leu | Arg | Thr | |
| 1290 | | | | | 1295 | | | | | 1300 | | | | | |

| ctg | cgt | gca | ctc | cgt | cct | ctg | aga | gct | ctg | tca | cga | ttt | gag | ggc | 4151 |
|---|---|---|---|---|---|---|---|---|---|---|---|---|---|---|---|
| Leu | Arg | Ala | Leu | Arg | Pro | Leu | Arg | Ala | Leu | Ser | Arg | Phe | Glu | Gly | |
| 1305 | | | | | 1310 | | | | | 1315 | | | | | |

| atg | agg | gtg | gtg | gtc | aat | gcc | ctg | gtg | ggc | gcc | atc | ccg | tcc | atc | 4196 |
|---|---|---|---|---|---|---|---|---|---|---|---|---|---|---|---|
| Met | Arg | Val | Val | Val | Asn | Ala | Leu | Val | Gly | Ala | Ile | Pro | Ser | Ile | |
| 1320 | | | | | 1325 | | | | | 1330 | | | | | |

| atg | aac | gtc | ctc | ctc | gtc | tgc | ctc | atc | ttc | tgg | ctc | atc | ttc | agc | 4241 |
|---|---|---|---|---|---|---|---|---|---|---|---|---|---|---|---|
| Met | Asn | Val | Leu | Leu | Val | Cys | Leu | Ile | Phe | Trp | Leu | Ile | Phe | Ser | |
| 1335 | | | | | 1340 | | | | | 1345 | | | | | |

| atc | atg | ggc | gtg | aac | ctc | ttt | gcg | ggg | aag | ttt | ggg | agg | tgc | atc | 4286 |
|---|---|---|---|---|---|---|---|---|---|---|---|---|---|---|---|
| Ile | Met | Gly | Val | Asn | Leu | Phe | Ala | Gly | Lys | Phe | Gly | Arg | Cys | Ile | |
| 1350 | | | | | 1355 | | | | | 1360 | | | | | |

| aac | cag | aca | gag | gga | gac | ttg | cct | ttg | aac | tac | acc | atc | gtg | aac | 4331 |
|---|---|---|---|---|---|---|---|---|---|---|---|---|---|---|---|
| Asn | Gln | Thr | Glu | Gly | Asp | Leu | Pro | Leu | Asn | Tyr | Thr | Ile | Val | Asn | |
| 1365 | | | | | 1370 | | | | | 1375 | | | | | |

| aac | aag | agc | cag | tgt | gag | tcc | ttg | aac | ttg | acc | gga | gaa | ttg | tac | 4376 |
|---|---|---|---|---|---|---|---|---|---|---|---|---|---|---|---|
| Asn | Lys | Ser | Gln | Cys | Glu | Ser | Leu | Asn | Leu | Thr | Gly | Glu | Leu | Tyr | |
| 1380 | | | | | 1385 | | | | | 1390 | | | | | |

| tgg | acc | aag | gtg | aaa | gtc | aac | ttt | gac | aac | gtg | ggg | gcc | ggg | tac | 4421 |
|---|---|---|---|---|---|---|---|---|---|---|---|---|---|---|---|
| Trp | Thr | Lys | Val | Lys | Val | Asn | Phe | Asp | Asn | Val | Gly | Ala | Gly | Tyr | |
| 1395 | | | | | 1400 | | | | | 1405 | | | | | |

| ctg | gcc | ctt | ctg | cag | gtg | tat | gaa | gag | cag | cct | cag | tgg | gaa | tac | 4466 |
|---|---|---|---|---|---|---|---|---|---|---|---|---|---|---|---|
| Leu | Ala | Leu | Leu | Gln | Val | Tyr | Glu | Glu | Gln | Pro | Gln | Trp | Glu | Tyr | |
| 1410 | | | | | 1415 | | | | | 1420 | | | | | |

| aac | ctc | tac | atg | tac | atc | tat | ttt | gtc | att | ttc | atc | atc | ttt | ggg | 4511 |
|---|---|---|---|---|---|---|---|---|---|---|---|---|---|---|---|
| Asn | Leu | Tyr | Met | Tyr | Ile | Tyr | Phe | Val | Ile | Phe | Ile | Ile | Phe | Gly | |
| 1425 | | | | | 1430 | | | | | 1435 | | | | | |

| tct | ttc | ttc | acc | ctg | aac | ctc | ttt | att | ggt | gtc | atc | att | gac | aac | 4556 |
|---|---|---|---|---|---|---|---|---|---|---|---|---|---|---|---|
| Ser | Phe | Phe | Thr | Leu | Asn | Leu | Phe | Ile | Gly | Val | Ile | Ile | Asp | Asn | |
| 1440 | | | | | 1445 | | | | | 1450 | | | | | |

| ttc | aac | caa | cag | aag | aaa | aag | tta | ggg | ggc | cag | gac | atc | ttc | atg | 4601 |
|---|---|---|---|---|---|---|---|---|---|---|---|---|---|---|---|
| Phe | Asn | Gln | Gln | Lys | Lys | Lys | Leu | Gly | Gly | Gln | Asp | Ile | Phe | Met | |
| 1455 | | | | | 1460 | | | | | 1465 | | | | | |

| aca | gag | gag | cag | aag | aag | tac | tac | aat | gcc | atg | aag | aag | ctg | ggc | 4646 |
|---|---|---|---|---|---|---|---|---|---|---|---|---|---|---|---|
| Thr | Glu | Glu | Gln | Lys | Lys | Tyr | Tyr | Asn | Ala | Met | Lys | Lys | Leu | Gly | |

-continued

| | | | | | | | | | | |
|---|---|---|---|---|---|---|---|---|---|---|
| | | 1470 | | | 1475 | | | 1480 | | |
| tcc | aag | aag | ccc | cag | aag | ccc | atc | cca | cgg | ccc | ctg | aac | aag | tac | 4691 |
| Ser | Lys | Lys | Pro | Gln | Lys | Pro | Ile | Pro | Arg | Pro | Leu | Asn | Lys | Tyr | |
| 1485 | | | | 1490 | | | | 1495 | | | | | | | |
| cag | ggc | ttc | ata | ttc | gac | att | gtg | acc | aag | cag | gcc | ttt | gac | gtc | 4736 |
| Gln | Gly | Phe | Ile | Phe | Asp | Ile | Val | Thr | Lys | Gln | Ala | Phe | Asp | Val | |
| 1500 | | | | 1505 | | | | 1510 | | | | | | | |
| acc | atc | atg | ttt | ctg | atc | tgc | ttg | aat | atg | gtg | acc | atg | atg | gtg | 4781 |
| Thr | Ile | Met | Phe | Leu | Ile | Cys | Leu | Asn | Met | Val | Thr | Met | Met | Val | |
| 1515 | | | | 1520 | | | | 1525 | | | | | | | |
| gag | aca | gat | gac | caa | agt | cct | gag | aaa | atc | aac | atc | ttg | gcc | aag | 4826 |
| Glu | Thr | Asp | Asp | Gln | Ser | Pro | Glu | Lys | Ile | Asn | Ile | Leu | Ala | Lys | |
| 1530 | | | | 1535 | | | | 1540 | | | | | | | |
| atc | aac | ctg | ctc | ttt | gtg | gcc | atc | ttc | aca | ggc | gag | tgt | att | gtc | 4871 |
| Ile | Asn | Leu | Leu | Phe | Val | Ala | Ile | Phe | Thr | Gly | Glu | Cys | Ile | Val | |
| 1545 | | | | 1550 | | | | 1555 | | | | | | | |
| aag | ctg | gct | gcc | ctg | cgc | cac | tac | tac | ttc | acc | aac | agc | tgg | aat | 4916 |
| Lys | Leu | Ala | Ala | Leu | Arg | His | Tyr | Tyr | Phe | Thr | Asn | Ser | Trp | Asn | |
| 1560 | | | | 1565 | | | | 1570 | | | | | | | |
| atc | ttc | gac | ttc | gtg | gtt | gtc | atc | ctc | tcc | atc | gtg | ggc | act | gtg | 4961 |
| Ile | Phe | Asp | Phe | Val | Val | Val | Ile | Leu | Ser | Ile | Val | Gly | Thr | Val | |
| 1575 | | | | 1580 | | | | 1585 | | | | | | | |
| ctc | tcg | gac | atc | atc | cag | aag | tac | ttc | ttc | tcc | ccg | acg | ctc | ttc | 5006 |
| Leu | Ser | Asp | Ile | Ile | Gln | Lys | Tyr | Phe | Phe | Ser | Pro | Thr | Leu | Phe | |
| 1590 | | | | 1595 | | | | 1600 | | | | | | | |
| cga | gtc | atc | cgc | ctg | gcc | cga | ata | ggc | cgc | atc | ctc | aga | ctg | atc | 5051 |
| Arg | Val | Ile | Arg | Leu | Ala | Arg | Ile | Gly | Arg | Ile | Leu | Arg | Leu | Ile | |
| 1605 | | | | 1610 | | | | 1615 | | | | | | | |
| cga | ggg | gcc | aag | ggg | atc | cgc | acg | ctg | ctc | ttt | gcc | ctc | atg | atg | 5096 |
| Arg | Gly | Ala | Lys | Gly | Ile | Arg | Thr | Leu | Leu | Phe | Ala | Leu | Met | Met | |
| 1620 | | | | 1625 | | | | 1630 | | | | | | | |
| tcc | ctg | cct | gcc | ctc | ttc | aac | atc | ggg | ctg | ctg | ctc | ttc | ctc | gtc | 5141 |
| Ser | Leu | Pro | Ala | Leu | Phe | Asn | Ile | Gly | Leu | Leu | Leu | Phe | Leu | Val | |
| 1635 | | | | 1640 | | | | 1645 | | | | | | | |
| atg | ttc | atc | tac | tcc | atc | ttt | ggc | atg | gcc | aac | ttc | gct | tat | gtc | 5186 |
| Met | Phe | Ile | Tyr | Ser | Ile | Phe | Gly | Met | Ala | Asn | Phe | Ala | Tyr | Val | |
| 1650 | | | | 1655 | | | | 1660 | | | | | | | |
| aag | tgg | gag | gct | ggc | atc | gac | gac | atg | ttc | aac | ttc | cag | acc | ttc | 5231 |
| Lys | Trp | Glu | Ala | Gly | Ile | Asp | Asp | Met | Phe | Asn | Phe | Gln | Thr | Phe | |
| 1665 | | | | 1670 | | | | 1675 | | | | | | | |
| gcc | aac | agc | atg | ctg | tgc | ctc | ttc | cag | atc | acc | acg | tcg | gcc | ggc | 5276 |
| Ala | Asn | Ser | Met | Leu | Cys | Leu | Phe | Gln | Ile | Thr | Thr | Ser | Ala | Gly | |
| 1680 | | | | 1685 | | | | 1690 | | | | | | | |
| tgg | gat | ggc | ctc | ctc | agc | ccc | atc | ctc | aac | act | ggg | ccg | ccc | tac | 5321 |
| Trp | Asp | Gly | Leu | Leu | Ser | Pro | Ile | Leu | Asn | Thr | Gly | Pro | Pro | Tyr | |
| 1695 | | | | 1700 | | | | 1705 | | | | | | | |
| tgc | gac | ccc | act | ctg | ccc | aac | agc | aat | ggc | tct | cgg | ggg | gac | tgc | 5366 |
| Cys | Asp | Pro | Thr | Leu | Pro | Asn | Ser | Asn | Gly | Ser | Arg | Gly | Asp | Cys | |
| 1710 | | | | 1715 | | | | 1720 | | | | | | | |
| ggg | agc | cca | gcc | gtg | ggc | atc | ctc | ttc | ttc | acc | acc | tac | atc | atc | 5411 |
| Gly | Ser | Pro | Ala | Val | Gly | Ile | Leu | Phe | Phe | Thr | Thr | Tyr | Ile | Ile | |
| 1725 | | | | 1730 | | | | 1735 | | | | | | | |
| atc | tcc | ttc | ctc | atc | gtg | gtc | aac | atg | tac | att | gcc | atc | atc | ctg | 5456 |
| Ile | Ser | Phe | Leu | Ile | Val | Val | Asn | Met | Tyr | Ile | Ala | Ile | Ile | Leu | |
| 1740 | | | | 1745 | | | | 1750 | | | | | | | |
| gag | aac | ttc | agc | gtg | gcc | acg | gag | gag | agc | acc | gag | ccc | ctg | agt | 5501 |
| Glu | Asn | Phe | Ser | Val | Ala | Thr | Glu | Glu | Ser | Thr | Glu | Pro | Leu | Ser | |
| 1755 | | | | 1760 | | | | 1765 | | | | | | | |
| gag | gac | gac | ttc | gat | atg | ttc | tat | gag | atc | tgg | gag | aaa | ttt | gac | 5546 |
| Glu | Asp | Asp | Phe | Asp | Met | Phe | Tyr | Glu | Ile | Trp | Glu | Lys | Phe | Asp | |

-continued

| | | | | | | | | | | | | | | |
|---|---|---|---|---|---|---|---|---|---|---|---|---|---|---|
| | | | | 1770 | | | | | 1775 | | | | | 1780 |

```
cca gag gcc act cag ttt att gag tat tcg gtc ctg tct gac ttt       5591
Pro Glu Ala Thr Gln Phe Ile Glu Tyr Ser Val Leu Ser Asp Phe
1785                1790                1795 gcc gat gcc ctg tct gag cca ctc cgt atc gcc aag ccc aac cag       5636
Ala Asp Ala Leu Ser Glu Pro Leu Arg Ile Ala Lys Pro Asn Gln
1800                1805                1810 ata agc ctc atc aac atg gac ctg ccc atg gtg agt ggg gac cgc       5681
Ile Ser Leu Ile Asn Met Asp Leu Pro Met Val Ser Gly Asp Arg
1815                1820                1825 atc cat tgc atg gac att ctc ttt gcc ttc acc aaa agg gtc ctg       5726
Ile His Cys Met Asp Ile Leu Phe Ala Phe Thr Lys Arg Val Leu
1830                1835                1840 ggg gag tct ggg gag atg gac gcc ctg aag atc cag atg gag gag       5771
Gly Glu Ser Gly Glu Met Asp Ala Leu Lys Ile Gln Met Glu Glu
1845                1850                1855 aag ttc atg gca gcc aac cca tcc aag atc tcc tac gag ccc atc       5816
Lys Phe Met Ala Ala Asn Pro Ser Lys Ile Ser Tyr Glu Pro Ile
1860                1865                1870 acc acc aca ctc cgg cgc aag cac gaa gag gtg tcg gcc atg gtt       5861
Thr Thr Thr Leu Arg Arg Lys His Glu Glu Val Ser Ala Met Val
1875                1880                1885 atc cag aga gcc ttc cgc agg cac ctg ctg caa cgc tct ttg aag       5906
Ile Gln Arg Ala Phe Arg Arg His Leu Leu Gln Arg Ser Leu Lys
1890                1895                1900 cat gcc tcc ttc ctc ttc cgt cag cag gcg ggc agc ggc ctc tcc       5951
His Ala Ser Phe Leu Phe Arg Gln Gln Ala Gly Ser Gly Leu Ser
1905                1910                1915 gaa gag gat gcc cct gag cga gag ggc ctc atc gcc tac gtg atg       5996
Glu Glu Asp Ala Pro Glu Arg Glu Gly Leu Ile Ala Tyr Val Met
1920                1925                1930 agt gag aac ttc tcc cga ccc ctt ggc cca ccc tcc agc tcc tcc       6041
Ser Glu Asn Phe Ser Arg Pro Leu Gly Pro Pro Ser Ser Ser Ser
1935                1940                1945 atc tcc tcc act tcc ttc cca ccc tcc tat gac agt gtc act aga       6086
Ile Ser Ser Thr Ser Phe Pro Pro Ser Tyr Asp Ser Val Thr Arg
1950                1955                1960 gcc acc agc gat aac ctc cag gtg cgg ggg tct gac tac agc cac       6131
Ala Thr Ser Asp Asn Leu Gln Val Arg Gly Ser Asp Tyr Ser His
1965                1970                1975 agt gaa gat ctc gcc gac ttc ccc cct tct ccg gac agg gac cgt       6176
Ser Glu Asp Leu Ala Asp Phe Pro Pro Ser Pro Asp Arg Asp Arg
1980                1985                1990 gag tcc atc gtg tga gcctcggcct ggctggccag acacactga aaagcagcct   6231
Glu Ser Ile Val
1995 ttttcaccat ggcaaaccta aatgcagtca gtcacaaacc agcctggggc cttcctggct   6291 ttgggagtaa gaaatgggcc tcagccccgc ggatcaacca ggcagagttc tgtggcgccg   6351 cgtggacagc cggagcagtt ggcctgtgct tggaggcctc agatagacct gtgacctggt   6411 ctggtcaggc aatgccctgc ggctctggaa agcaacttca tcccagctgc tgaggcgaaa   6471 tataaaactg agactgtata tgttgtgaat gggctttcat aaatttatta tatttgatat   6531 tttttttactt gagcaaagaa ctaaggattt ttccatggac atgggcagca attcacgctg   6591 tctcttctta accctgaaca agagtgtcta tggagcagcc ggaagtctgt tctcaaagca   6651 gaagtggaat ccagtgtggc tcccacaggt cttcactgcc cagggtcga atggggtccc      6711 cctcccactt gacctgagat gctgggaggg ctgaacccc actcacacaa gcacacacac    6771
```

```
acagtcctca cacacggagg ccagacacag gccgtgggac ccaggctccc agcctaaggg   6831
agacaggcct ttccctgccg gccccccaag gatgggttc ttgtccacgg ggctcactct   6891
ggccccctat tgtctccaag gtcccatttt ccccctgtgt tttcacgcag gtcatattgt   6951
cagtcctaca aaaataaaag gcttccagag gagagtggcc tgggtccag ggctggccct   7011
aggcactgat agttgccttt tcttcccctc ctgtaagagt attaacaaaa ccaaaggaca   7071
caagggtgca agccccattc acggcctggc atgcagcttg tccttgctcc tggaacctgg   7131
caggccctgc ccagccagcc atcggaagag agggctgagc catgggggtt tggggctaag   7191
aagttcacca gccctgagcc atggcggccc ctcagcctgc ctgaagagag gaaactggcg   7251
atctcccagg gctctctgga ccatacgcgg aggagttttc tgtgtggtct ccagctcctc   7311
tccagacaca gagacatggg agtggggagc ggagcttggc cctgcgccct gtgcagggaa   7371
agggatggtc aggcccagtt ctcgtgccct tagaggggaa tgaaccatgg cacctttgag   7431
agaggggca ctgtggtcag gcccagcctc tctggctcag cccgggatcc tgatggcacc   7491
cacacagagg acctctttgg ggcaagatcc aggtggtccc ataggtcttg tgaaaaggct   7551
ttttcaggga aaaatatttt actagtccaa tcaccccag gacctcttca gctgctgaca   7611
atcctattta gcatatgcaa atcttttaac atagagaact gtcaccctga ggtaacaggg   7671
tcaactggcg aagcctgagc aggcagggc ttggctgccc cattccagct ctcccatgga   7731
gccctccac cgggcgcatg cctcccaggc cacctcagtc tcacctgccg gctctgggct   7791
ggctgctcct aacctacctc gccgagctgt cggagggctg gacatttgtg gcagtgctga   7851
agggggcatt gccggcgagt aaagtattat gtttcttctt gtcaccccag ttcccttggt   7911
ggcaaccca gacccaaccc atgccctga cagatctagt tctcttctcc tgtgttccct   7971
ttgagtccag tgtgggacac ggtttaactg tcccagcgac atttctccaa gtggaaatcc   8031
tattttgta gatctccatg ctttgctctc aaggcttgga gaggtatgtg ccctcctgg   8091
gtgctcaccg cctgctacac aggcaggaat gcggttggga ggcaggtcgg gctgccagcc   8151
cagctggccg gaaggagact gtggttttg tgtgtgtgga cagcccggga gctttgagac   8211
aggtgcctgg ggctggctgc agacggtgtg gttggggtg ggaggtgagc tagacccaac   8271
ccttagcttt tagcctggct gtcacctttt taatttccag aactgcacaa tgaccagcag   8331
gagggaagga cagacatcaa gtgccagatg ttgtctgaac taatcgagca cttctcacca   8391
aacttcatgt ataaataaaa tacatatttt taaaacaaac caataaatgg cttacatga   8450
```

<210> SEQ ID NO 13
<211> LENGTH: 1998
<212> TYPE: PRT
<213> ORGANISM: Homo sapiens

<400> SEQUENCE: 13

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
```

```
                    85                  90                  95
Asn Lys Gly Lys Thr Ile Phe Arg Phe Ser Ala Thr Asn Ala Leu Tyr
                100                 105                 110

Val Leu Ser Pro Phe His Pro Ile Arg Arg Ala Ala Val Lys Ile Leu
                115                 120                 125

Val His Ser Leu Phe Asn Met Leu Ile Met Cys Thr Ile Leu Thr Asn
                130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
                180                 185                 190

Trp Asn Trp Leu Asp Phe Ser Val Ile Met Ala Tyr Val Ser Glu
                195                 200                 205

Asn Ile Lys Leu Gly Asn Leu Ser Ala Leu Arg Thr Phe Arg Val Leu
                210                 215                 220

Arg Ala Leu Lys Thr Ile Ser Val Ile Pro Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
                260                 265                 270

Met Gly Asn Leu Arg His Lys Cys Val Arg Asn Phe Thr Ala Leu Asn
                275                 280                 285

Gly Thr Asn Gly Ser Val Glu Ala Asp Gly Leu Val Trp Glu Ser Leu
                290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
                340                 345                 350

Thr Ser Phe Asp Ser Phe Ala Trp Ala Phe Leu Ala Leu Phe Arg Leu
                355                 360                 365

Met Thr Gln Asp Cys Trp Glu Arg Leu Tyr Gln Gln Thr Leu Arg Ser
                370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
                420                 425                 430

Arg Phe Gln Glu Ala Met Glu Met Leu Lys Lys Glu His Glu Ala Leu
                435                 440                 445

Thr Ile Arg Gly Val Asp Thr Val Ser Arg Ser Ser Leu Glu Met Ser
450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
                500                 505                 510
```

-continued

```
Arg Gly Leu Ser Arg Thr Ser Met Lys Pro Arg Ser Ser Arg Gly Ser
            515                 520                 525

Ile Phe Thr Phe Arg Arg Asp Leu Gly Ser Glu Ala Asp Phe Ala
        530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
    610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
        835                 840                 845

Ile Val Phe Ile Phe Ala Val Val Gly Met Gln Leu Phe Gly Lys Asn
    850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
        915                 920                 925

Val Val Leu Asn Leu Phe Leu Ala Leu Leu Leu Ser Ser Phe Ser Ala
    930                 935                 940
```

```
Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
            965                 970                 975

Thr Trp Asp Phe Cys Cys Gly Leu Leu Arg Gln Arg Pro Gln Lys Pro
        980                 985                 990

Ala Ala Leu Ala Ala Gln Gly Gln Leu Pro Ser Cys Ile Ala Thr Pro
    995                 1000                1005

Tyr Ser Pro Pro Pro Glu Thr Glu Lys Val Pro Pro Thr Arg
1010                1015                1020

Lys Glu Thr Arg Phe Glu Glu Gly Gln Pro Gly Gln Gly Thr
1025                1030                1035

Pro Gly Asp Pro Glu Pro Val Cys Val Pro Ile Ala Val Ala Glu
1040                1045                1050

Ser Asp Thr Asp Asp Gln Glu Asp Glu Glu Asn Ser Leu Gly
1055                1060                1065

Thr Glu Glu Glu Ser Ser Lys Gln Gln Glu Ser Gln Pro Val Ser
1070                1075                1080

Gly Gly Pro Glu Ala Pro Pro Asp Ser Arg Thr Trp Ser Gln Val
1085                1090                1095

Ser Ala Thr Ala Ser Ser Glu Ala Glu Ala Ser Ala Ser Gln Ala
1100                1105                1110

Asp Trp Arg Gln Gln Trp Lys Ala Glu Pro Gln Ala Pro Gly Cys
1115                1120                1125

Gly Glu Thr Pro Glu Asp Ser Cys Ser Glu Gly Ser Thr Ala Asp
1130                1135                1140

Met Thr Asn Thr Ala Glu Leu Leu Glu Gln Ile Pro Asp Leu Gly
1145                1150                1155

Gln Asp Val Lys Asp Pro Glu Asp Cys Phe Thr Glu Gly Cys Val
1160                1165                1170

Arg Arg Cys Pro Cys Cys Ala Val Asp Thr Thr Gln Ala Pro Gly
1175                1180                1185

Lys Val Trp Trp Arg Leu Arg Lys Thr Cys Tyr His Ile Val Glu
1190                1195                1200

His Ser Trp Phe Glu Thr Phe Ile Ile Phe Met Ile Leu Leu Ser
1205                1210                1215

Ser Gly Ala Leu Ala Phe Glu Asp Ile Tyr Leu Glu Glu Arg Lys
1220                1225                1230

Thr Ile Lys Val Leu Leu Glu Tyr Ala Asp Lys Met Phe Thr Tyr
1235                1240                1245

Val Phe Val Leu Glu Met Leu Leu Lys Trp Val Ala Tyr Gly Phe
1250                1255                1260

Lys Lys Tyr Phe Thr Asn Ala Trp Cys Trp Leu Asp Phe Leu Ile
1265                1270                1275

Val Asp Val Ser Leu Val Ser Leu Val Ala Asn Thr Leu Gly Phe
1280                1285                1290

Ala Glu Met Gly Pro Ile Lys Ser Leu Arg Thr Leu Arg Ala Leu
1295                1300                1305

Arg Pro Leu Arg Ala Leu Ser Arg Phe Glu Gly Met Arg Val Val
1310                1315                1320

Val Asn Ala Leu Val Gly Ala Ile Pro Ser Ile Met Asn Val Leu
1325                1330                1335

Leu Val Cys Leu Ile Phe Trp Leu Ile Phe Ser Ile Met Gly Val
```

-continued

```
              1340                1345                1350

Asn Leu Phe Ala Gly Lys Phe Gly Arg Cys Ile Asn Gln Thr Glu
        1355                1360                1365

Gly Asp Leu Pro Leu Asn Tyr Thr Ile Val Asn Asn Lys Ser Gln
        1370                1375                1380

Cys Glu Ser Leu Asn Leu Thr Gly Glu Leu Tyr Trp Thr Lys Val
        1385                1390                1395

Lys Val Asn Phe Asp Asn Val Gly Ala Gly Tyr Leu Ala Leu Leu
        1400                1405                1410

Gln Val Tyr Glu Glu Gln Pro Gln Trp Glu Tyr Asn Leu Tyr Met
        1415                1420                1425

Tyr Ile Tyr Phe Val Ile Phe Ile Ile Phe Gly Ser Phe Phe Thr
        1430                1435                1440

Leu Asn Leu Phe Ile Gly Val Ile Ile Asp Asn Phe Asn Gln Gln
        1445                1450                1455

Lys Lys Lys Leu Gly Gly Gln Asp Ile Phe Met Thr Glu Glu Gln
        1460                1465                1470

Lys Lys Tyr Tyr Asn Ala Met Lys Lys Leu Gly Ser Lys Lys Pro
        1475                1480                1485

Gln Lys Pro Ile Pro Arg Pro Leu Asn Lys Tyr Gln Gly Phe Ile
        1490                1495                1500

Phe Asp Ile Val Thr Lys Gln Ala Phe Asp Val Thr Ile Met Phe
        1505                1510                1515

Leu Ile Cys Leu Asn Met Val Thr Met Met Val Glu Thr Asp Asp
        1520                1525                1530

Gln Ser Pro Glu Lys Ile Asn Ile Leu Ala Lys Ile Asn Leu Leu
        1535                1540                1545

Phe Val Ala Ile Phe Thr Gly Glu Cys Ile Val Lys Leu Ala Ala
        1550                1555                1560

Leu Arg His Tyr Tyr Phe Thr Asn Ser Trp Asn Ile Phe Asp Phe
        1565                1570                1575

Val Val Val Ile Leu Ser Ile Val Gly Thr Val Leu Ser Asp Ile
        1580                1585                1590

Ile Gln Lys Tyr Phe Phe Ser Pro Thr Leu Phe Arg Val Ile Arg
        1595                1600                1605

Leu Ala Arg Ile Gly Arg Ile Leu Arg Leu Ile Arg Gly Ala Lys
        1610                1615                1620

Gly Ile Arg Thr Leu Leu Phe Ala Leu Met Met Ser Leu Pro Ala
        1625                1630                1635

Leu Phe Asn Ile Gly Leu Leu Leu Phe Leu Val Met Phe Ile Tyr
        1640                1645                1650

Ser Ile Phe Gly Met Ala Asn Phe Ala Tyr Val Lys Trp Glu Ala
        1655                1660                1665

Gly Ile Asp Asp Met Phe Asn Phe Gln Thr Phe Ala Asn Ser Met
        1670                1675                1680

Leu Cys Leu Phe Gln Ile Thr Thr Ser Ala Gly Trp Asp Gly Leu
        1685                1690                1695

Leu Ser Pro Ile Leu Asn Thr Gly Pro Pro Tyr Cys Asp Pro Thr
        1700                1705                1710
```

```
Leu Pro Asn Ser Asn Gly Ser Arg Gly Asp Cys Gly Ser Pro Ala
    1715                1720                1725

Val Gly Ile Leu Phe Phe Thr Thr Tyr Ile Ile Ile Ser Phe Leu
    1730                1735                1740

Ile Val Val Asn Met Tyr Ile Ala Ile Ile Leu Glu Asn Phe Ser
    1745                1750                1755

Val Ala Thr Glu Glu Ser Thr Glu Pro Leu Ser Glu Asp Asp Phe
    1760                1765                1770

Asp Met Phe Tyr Glu Ile Trp Glu Lys Phe Asp Pro Glu Ala Thr
    1775                1780                1785

Gln Phe Ile Glu Tyr Ser Val Leu Ser Asp Phe Ala Asp Ala Leu
    1790                1795                1800

Ser Glu Pro Leu Arg Ile Ala Lys Pro Asn Gln Ile Ser Leu Ile
    1805                1810                1815

Asn Met Asp Leu Pro Met Val Ser Gly Asp Arg Ile His Cys Met
    1820                1825                1830

Asp Ile Leu Phe Ala Phe Thr Lys Arg Val Leu Gly Glu Ser Gly
    1835                1840                1845

Glu Met Asp Ala Leu Lys Ile Gln Met Glu Glu Lys Phe Met Ala
    1850                1855                1860

Ala Asn Pro Ser Lys Ile Ser Tyr Glu Pro Ile Thr Thr Thr Leu
    1865                1870                1875

Arg Arg Lys His Glu Glu Val Ser Ala Met Val Ile Gln Arg Ala
    1880                1885                1890

Phe Arg Arg His Leu Leu Gln Arg Ser Leu Lys His Ala Ser Phe
    1895                1900                1905

Leu Phe Arg Gln Gln Ala Gly Ser Gly Leu Ser Glu Glu Asp Ala
    1910                1915                1920

Pro Glu Arg Glu Gly Leu Ile Ala Tyr Val Met Ser Glu Asn Phe
    1925                1930                1935

Ser Arg Pro Leu Gly Pro Pro Ser Ser Ser Ser Ile Ser Ser Thr
    1940                1945                1950

Ser Phe Pro Pro Ser Tyr Asp Ser Val Thr Arg Ala Thr Ser Asp
    1955                1960                1965

Asn Leu Gln Val Arg Gly Ser Asp Tyr Ser His Ser Glu Asp Leu
    1970                1975                1980

Ala Asp Phe Pro Pro Ser Pro Asp Arg Asp Arg Glu Ser Ile Val
    1985                1990                1995

<210> SEQ ID NO 14
<211> LENGTH: 26
<212> TYPE: PRT
<213> ORGANISM: Oryctolagus cuniculus

<400> SEQUENCE: 14

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
                20                  25
```